United States Patent
Smith et al.

(10) Patent No.: US 7,078,208 B2
(45) Date of Patent: Jul. 18, 2006

(54) THERMOSTABLE REVERSE TRANSCRIPTASES AND USES THEREOF

(75) Inventors: Michael D. Smith, Rockville, MD (US); Robert Jason Potter, Frederick, MD (US); Gulshan Dhariwal, Potomac, MD (US); Gary F. Gerard, Frederick, MD (US); Kim Rosenthal, Laytonsville, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/845,157

(22) Filed: May 1, 2001

(65) Prior Publication Data

US 2002/0090618 A1   Jul. 11, 2002

Related U.S. Application Data

(60) Provisional application No. 60/207,196, filed on May 26, 2000.

(51) Int. Cl.
    C12N 9/12 (2006.01)
(52) U.S. Cl. ............... 435/194; 435/91.1; 435/91.2
(58) Field of Classification Search ........ 536/22.1, 536/23.1, 24.3, 24.31; 435/6, 91.2, 91.21
    See application file for complete search history.

(56) References Cited

U.S. PATENT DOCUMENTS

| 5,244,797 A | 9/1993 | Kotewicz et al. ............ 435/194 |
| 5,405,776 A | 4/1995 | Kotewicz et al. ...... 435/252.33 |
| 5,405,776 A | 10/1996 | Kotewicz et al. ............ 435/194 |
| 5,668,005 A | 9/1997 | Kotewicz et al. ............ 435/194 |
| 5,244,797 A | 8/1998 | Kotewicz et al. ............ 435/194 |
| 6,063,608 A | 5/2000 | Kotewicz et al. ............ 435/194 |
| 6,136,582 A | 10/2000 | Gao et al. .................. 435/194 |

FOREIGN PATENT DOCUMENTS

| JP | 2000-139457 | * | 5/2000 |
| WO | WO 98/47912 | | 10/1998 |
| WO | WO 99/10366 | | 3/1999 |
| WO | WO 01/68895 A1 | | 9/2001 |
| WO | WO 01/092500 | | 12/2001 |

OTHER PUBLICATIONS

Blain et al, "Nuclease activities of Moloney Murine Leukemia Virus Reverse Transcriptase", J. Biol. Chem. (1993) 268(31):23585-23592.*

Lawyer et al, "Isolation, characterization and expression in *Escherichia coli* of the DNA polymerase gene from *Thermus aquaticus*", J. BIol. Chem. (1989) 264(11):6427-6437.*

Halvas, E.K., et al., "Development of an In Vivo Assay To Identify Structural Determinants in Murine Leukemia Virus Reverse Transcriptase Important for Fidelity," *J. Virol.* 74:312-319, American Society for Microbiology (Jan. 2000).

Kaushik, N., et al., "Valine of the YVDD Motif of Moloney Murine Leukemia Virus Reverse Transcriptase: Role in the Fidelity of DNA Synthesis," *Biochemistry* 39:5155-5165, American Chemical Society (May 2000), published on the Web Apr. 7, 2000.

Unverified English language translation of JP 2000-139457, Ralph McElroy Translation Company.

Arion, D., et al., "The K65R Mutation Confers Increased DNA Polymerase Processivity to HIV-1 Reverse Transcriptase," *J. Biol. Chem.* 271:19860-19864, American Society for Biochemistry and Molecular Biology (1996).

Bakhanashvili, M., and Hizi, A., "The fidelity of the reverse tanscriptases of human immunodeficiency viruses and murine leukemia virus, exhibited by the mispair extension frequencies, is sequence dependent and enzyme related," *FEBS* 319:201-205, Elsevier Science Publishers B.V. (1993).

Bakhanashvili, M., and Hizi, A., "A possible role for cysteine residues in the fidelity of DNA synthesis exhibited by the reverse transcriptases of human immunodeficiency viruses type 1 and type 2," *FEBS* 304:289-293, Elsevier Science Publishers B.V. (1992).

Bakhanashvili, M., et al., "Mutational studies of human immunodeficiency virus type 1 reverse transcriptase: the involvement of residues 183 and 184 in the fidelity of DNA synthesis," *FEBS Lett.* 391:257-262, Elsevier Science Publishers B.V. (1996).

Bakhanashvili, M., and Hizi, A., "Fidelity of the RNA-Dependent DNA Synthesis Exhibited by the Reverse Transcriptases of Human Immunodeficiency Virus Types 1 and 2 and of Murine Leukemia Virus: Mispair Extension Frequencies," *Biochem.* 31:9393-9398, American Chemical Society (1992).

Barnes, W.M., "The fidelity of *Taq* polymerase catalyzing PCR is improved by an N-terminal deletion," *Gene* 112:29-35, Elsevier Science Publishers B.V. (1992).

(Continued)

Primary Examiner—Jeffrey Fredman
(74) *Attorney, Agent, or Firm*—Sterne, Kessler, Goldstein & Fox PLLC

(57) ABSTRACT

The present invention is in the fields of molecular and cellular biology. The invention is generally related to reverse transcriptase enzymes and methods for the reverse transcription of nucleic acid molecules, especially messenger RNA molecules. Specifically, the invention relates to reverse transcriptase enzymes which have been mutated or modified to increase thermostability, decrease terminal deoxynucleotidyl transferase activity, and/or increase fidelity, and to methods of producing, amplifying or sequencing nucleic acid molecules (particularly cDNA molecules) using these reverse transcriptase enzymes or compositions. The invention also relates to nucleic acid molecules produced by these methods and to the use of such nucleic acid molecules to produce desired polypeptides. The invention also concerns kits comprising such enzymes or compositions.

26 Claims, 9 Drawing Sheets

OTHER PUBLICATIONS

Basu, S., et al., "Sulphydryl groups in the template-primer-binding domain of murine leukemia virus reverse transcriptase," *Biochem. J. 296*:577-583, The Chemical Society, London (1993).

Bebenek, K., et al., "Reduced Frameshift Fidelity and Processivity of HIV-1 Reverse Transcriptase Mutants Containing Alanine Substitutions in Helix H of the Thumb Subdomain," *J. Biol. Chem. 270*:19516-19523, American Society for Biochemistry and Molecular Biology (1995).

Bebenek, K., et al., "The Fidelity of DNA Synthesis Catalyzed by Derivatives of *Escherichia coli* DNA Polymerase 1," *J. Biol. Chem. 265*:13878-13887, The American Society for Biochemistry and Molecular Biology (1990).

Ben-Artzi, H., et al., "Characterization of the double stranded RNA dependent RNase activity associated with recombinant reverse transcriptases," *Nucleic Acids Res. 20*:5115-5118, Oxford University Press (1992).

Berger, S.L., et al., "Reverse Transcriptase and Its Associated Ribonuclease H: Interplay of Two Enzyme Activities Controls the Yield of Single-Stranded Complementary Deoxyribonucleic Acid," *Biochemistry 22*:2365-2372, The American Chemical Society (1983).

Blain, S.W., and Goff, S.P., "Effects on DNA Synthesis and Translocation Caused by Mutations in the RNase H Domain of Moloney Murine Leukemia Virus Reverse Transcriptase," *J. Virol. 69*:4440-4452, The American Society for Microbiology (1995).

Caliendo, A.M., et al., "Effects of Zidovudine-Selected Human Immunodeficiency Virus Type 1 Reverse Transcriptase Amino Acid Substitutions on Processive DNA Synthesis and Viral Replication," *J. Virol. 70*:2146-2153, The American Society for Microbiology (1996).

Carroll, S.S., et al., "A Mutant of DNA Polymerase I (Klenow Fragment) with Reduced Fidelity," *Biochem. 30*:804-813, American Chemical Society (1991).

Carter, P. and Wells, J.A., "Engineering Enzyme Specificity by 'Substrate-Assisted Catalysis,'" *Science 237*:394-399, American Association for the Advancement of Science (1987).

Chen, Y., and Marion, P.L., "Amino Acids Essential for RNase H Activity of Hepadnaviruses Are Also Required for Efficient Elongation of Minus-Strand Viral DNA," *J. Virol. 70*:6151-6156, The American Society for Microbiology (1996).

Chowdhury, K., et al., "Elucidation of the Role of Arg 110 of Murine Leukemia Virus Reverse Transcriptase in the Catalytic Mechanism: Biochemical Characterization of Its Mutant Enzymes," *Biochemistry 35*:16610-16620, American Chemical Society (1996).

Creighton, S., et al., "Base Mispair Extension Kinetics," *J. Biol. Chem. 267*:2633-2639, American Society for Biochemistry and Molecular Biology (1992).

DeStefano, J.J., et al., "Parameters that influence processive synthesis and site-specific termination by human immunodeficiency virus reverse transcriptase on RNA and DNA templates," *Biochimica et Biophysica Acta 1131*:270-280, Elsevier Science Publishers B.V. (1992).

Diaz, L., and DeStefano, J.J., "Strand transfer is enhanced by mismatched nucleotide at the 3' primer terminus: a possible link between HIV reverse transcriptase fidelity and recombination," *Nucleic Acids Res. 24*:3086-3092, Oxford University Press (1996).

Drosopoulos, W.C., and Prasad, V.R., "Increased Polymerase Fidelity of E89G, a Nucleoside Analog-Resistant Variant of Human Immunodeficiency Virus Type 1 Reverse Transcriptase," *J. Virol. 70*:4834-4838, The American Society for Microbiology (1996).

Drosopoulos, W.C., and Prasad, V.R., "Increased Misincorporation Fidelity Observed for Nucleoside Analog Resistance Mutations M184V and E89G in Human Immunodeficiency Virus Type 1 Reverse Transcriptase Does Not Correlate with the Overall Error Rate Measured In Vitro," *J. Virol. 72*:4224-4230, The American Society for Microbiology (1998).

Eckert, K.A., and Kunkel, T.A., "Fidelity of DNA synthesis catalyzed by human DNA polymerase α and HIV-1 reverse transcriptase: effect of reaction pH," *Nucleic Acids Res. 21*:5212-5220, Oxford University Press (1993).

Eger, B.T., et al., "Mechanism of DNA Replication Fidelity for Three Mutants of DNA Polymerase I: Klenow fragment KF(exo+), KF(polA5), and KF(exo-)," *Biochem. 30*:1441-1448, American Chemical Society (1991).

Feng, J.Y., and Anderson, K.S., "Mechanistic Studies Examining the Efficiency and Fidelity of DNA Synthesis by the 3TC-Resistant Mutant (184V) of HIV-1 Reverse Transcriptase," *Biochemistry 38*:9440-9448, The American Chemical Society (Jul. 1999); Published on the web on Jun. 30, 1999.

Finston, W.I. and Champoux, J.J., "RNA-Primed Initiation of Moloney Murine Leukemia Virus Plus Strands by Reverse Transcriptase In Vitro," *J. Virology 51*:26-33, American Society for Microbiology (1984).

Gao, G., and Goff, S.P., "Replication Defect of Moloney Murine Leukemia Virus with a Mutant Reverse Transcriptase That Can Incorporate Ribonucleotides and Deoxyribonucleotides," *J. Virol. 72*:5905-5911, The American Society for Microbiology (1998).

Gerard, G.F., et al., "cDNA Synthesis by Cloned Moloney Murine Leukemia Virus Reverse Transcriptase Lacking RNase H Activity," *Focus 11*:66-69, Life Technologies, Inc. (1989).

Gerard, G.F., et al., "Influence on Stability in *Escherichia coli* of the Carboxy-Terminal Structure of Cloned Moloney Murine Leukemia Virus Reverse Transcriptase," *DNA 5*:271-279, Mary Ann Liebert, Inc. (1986).

Gerard, G., et al., "cDNA Synthesis by Moloney Murine Leukemia Virus RNase H-Minus Reverse Transcriptase Possessing Full DNA Polymerase Activity," *Focus 14*:91-93, Life Technologies, Inc. (1992).

Gerwin, B.I., et al., "Mutant of β-Tropic Murine Leukemia Virus Synthesizing and Altered Polymerase Molecule," *J. Virology 31*:741-751, The American Society for Microbiology (1979).

Goff, S.P., "Retroviral Reverse Transcriptase: Synthesis, Structure, and Function," *J. Acquired Immune Deficiency Syndrome 3*:817-831, Raven Press (1990).

Goff, S.P. and Lobel, L.I. , "Mutants of murine leukemia viruses and retroviral replication," *Biochimica et Biophysica Acta. 907*:93-123, Elsevier Science Publishers B.V. (1987).

Goobar-Larsson, L., et al., "Disruption of a Salt Bridge between Asp 488 and Lys 465 in HIV-1 Reverse Transcriptase Alters Its Proteolytic Processing and Polymerase Activity," *Virology 196*:731-738, Academic Press (1993).

Götte, M., et al., "The M184V Mutation in the Reverse Transcriptase of Human Immunodeficiency Virus Type 1 Impairs Rescue of Chain-Terminated DNA Synthesis," *J. Virol. 74*:3579-3585, The American Society for Microbiology (Apr. 2000).

Guo, J., et al., "Defects in Primer-Template Binding, Processive DNA Synthesis, and RNase H Activity Associated with Chimeric Reverse Transcriptases Having the Murine Leukemia Virus Polymerase Domain Joined to *Escherichia coli* RNase H," *Biochemistry* 34:5018-5029, The American Chemical Society (1995).

Hamburgh, M.E., et al., "The influence of 3TC-resistance mutations E89G and M184V in the human immunodeficiency virus reverse transcriptase on mispair extension efficiency," *Nucleic Acids Res.* 26:4389-4394, Oxford University Press (1998).

Hite, J.M., et al., "Factors affecting fidelity of DNA synthesis during PCR amplification of $d(C-A)_n \cdot d(G-T)_n$ microsatellite repeats," *Nucleic Acids Res.* 24:2429-2434, Oxford University Press (1996).

Hsu, M., et al., "Higher fidelity of RNA-dependent DNA mispair extension by M184V drug-resistant than wild-type reverse transcriptase of human immunodeficiency virus type 1," *Nucleic Acids Research* 25:4532-4536, Oxford University Press (1997).

Jin, J., et al., "Analysis of the Role of Glutamine 190 in the Catalytic Mechanism of Murine Leukemia Virus Reverse Transcriptase," *J. Biol. Chem.* 274:20861-20868, American Society for Biochemistry and Molecular Biology (Jul. 1999).

Kaushik, N., et al., "Role of Glutamine-151 of Human Immunodeficiency Virus Type-1 Reverse Transcriptase in RNA-Directed DNA Synthesis," *Biochemistry* 36:14430-14438, The American Chemical Society (1997).

Kaushik, N., et al., "Role of Glutamine 151 of Human Immunodeficiency Virus Type-1 Reverse Transcriptase in Substrate Selection As Assessed by Site-Directed Mutagensis," *Biochemistry* 39:2912-2920, The American Chemical Society (Mar. 2000); Published on the web on Feb. 22, 2000.

Kaushik, N., et al., "Tyrosine 222, a Member of the YXDD Motif of MuLV RT, Is Catalytically Essential and Is a Major Component of the Fidelity Center," *Biochemistry* 38:2617-2627, The American Chemical Society (Mar. 1999); Published on the web on Feb. 10, 1999.

Kerr, S.G., and Anderson, K.S., "RNA Dependent DNA Replication Fidelity of HIV-1 Reverse Transcriptase: Evidence of Discrimination between DNA and RNA Substrates," *Biochemistry* 36:14056-14063, The American Chemical Society (1997).

Kim, B., et al., "Fidelity of Mutant HIV-1 Reverse Transcriptases: Interaction with the Single-Stranded Template Influences the Accuracy of DNA Synthesis," *Biochemistry* 37:5831-5839, The American Chemical Society (1998); Published on the web on Apr. 9, 1998.

Kim, B., et al., "New Human Immunodeficiency Virus, Type 1 Reverse Transcriptase (HIV-1 RT) Mutants with Increased Fidelity of DNA Synthesis," *J. Biol. Chem.* 274:27666-27673, American Society for Biochemistry and Molecular Biology (Sep. 1999).

Levin, J.G., et al., "Murine Leukemia Virus Mutant with a Frameshift in the Reverse Transcriptase Coding Region: Implications for *pol* Gene Structure," *J. Virology* 51:470-478, American Society for Microbiology (1984).

Lewis, D.A., et al., "Uniquely Altered DNA Replication Fidelity Conferred by an Amino Acid Change in the Nucleotide Binding Pocket of Human Immunodeficiency Virus Type 1 Reverse Transcriptase," *J. Biol. Chem.* 274:32924-32930, The American Society for Biochemistry and Molecular Biology (Nov. 1999).

Martin-Hernandez, A.M., et al., "Human immunodeficiency virus type 1 reverse transcriptase: role of Tyr115 in deoxynucleotide binding and misinsertion fidelity of DNA synthesis," *EMBO J.* 15:4434-4442, Oxford University Press (1996).

Martin-Hernandez, A.M., et al., "Mispair extension fidelity of human immunodeficiency virus type 1 reverse transcriptases with amino acid substitutions affecting Tyr115," *Nucleic Acids Res.* 25:1383-1389, Oxford University Press (1997).

Messer, L.I., et al., "Functional Analysis of Reverse Transcription by a Frameshift *pol* Mutant of Murine Leukemia Virus," *Virology* 146:146-152, Academic Press, Inc. (1985).

Oude Essink, B.B., et al., "Increased polymerase fidelity of the 3TC-resistant variants of HIV-1 reverse transcriptase," *Nucleic Acids Res.* 25:3212-3217, Oxford University Press (1997).

Pandey, V.N., et al., "Role of Methionine 184 of Human Immunodeficiency Virus Type-1 Reverse Transcriptase in the Polymerase Function and Fidelity of DNA Synthesis," *Biochemistry* 35:2168-2179, The American Chemical Society (1996).

Patel, P.H., et al., "Insights into DNA Polymerization Mechanisms from Structure and Function Analysis of HIV-1 Reverse Transcriptase," *Biochemistry* 34:5351-5363, The American Chemical Society (1995).

Perrino, F.W., et al., "Extension of mismatched 3' termini of DNA is a major determinant of the infidelity of human immunodeficiency virus type 1 reverse transcriptase," *Proc. Natl. Acad. Sci. USA* 86:8343-8347, The National Academy of Sciences of the USA (1989).

Pop, M.P., and Biebricher, C.K., "Kinetic Analysis of Pausing and Fidelity of Human Immunodeficiency Virus Type 1 Reverse Transcription," *Biochemistry* 35:5054-5062, The American Chemical Society (1996).

Prasad, V.R. and Goff, S.P., "Linker insertion mutagenesis of the human immunodeficiency virus reverse transcriptase expressed in bacteria: Definition of the minimal polymerase domain," *Proc. Natl. Acad. Sci. USA* 86:3104-3108, The National Academy of Sciences of the USA (1989).

Quan, Y., et al., "Dominance of the E89G Substitution in HIV-1 Reverse Transcriptase in Regard to Increased Polymerase Processivity and Patterns of Pausing," *J. Biol. Chem.* 273:21918-21925, American Society for Biochemistry and Molecular Biology (1998).

Repaske, R., et al., "Inhibition of RNase H Activity and Viral Replication by Single Mutations in the 3' Region of Moloney Murine Leukemia Virus Reverse Transcriptase," *J. Virology* 63:1460-1464, American Society for Microbiology (1989).

Resnick, R., et al., "Involvement of Retrovirus Reverse Transcriptase-Associated RNase H in the Initiation of Strong-Stop (+) DNA Synthesis and the Generation of the Long Terminal Repeat," *J. Virology* 51:813-821, American Society for Microbiology (1984).

Rezende, L.F., et al., "The Impact of Multidideoxynucleoside Resistance-Conferring Mutations in Human Immunodeficiency Virus Type 1 Reverse Transcriptase on Polymerase Fidelity and Error Specificity," *J. Virol.* 72:2890-2895, The American Society for Microbiology (1998).

Rezende, L.F., et al., "The influence of 3TC resistance mutation M184I on the fidelity and error specificity of human immunodeficiency virus type 1 reverse transcriptase," *Nucleic Acids Res. 26*:3066-3072, Oxford University Press (1998).

Rubinek, T., et al., "The fidelity of 3' misinsertion and mispair extension during DNA synthesis exhibited by two drug-resistant mutants of the reverse transcriptase of human immunodeficiency virus type 1 with Leu74→Val and Glu89→Gly," *Eur. J. Biochem. 247*:238-247, FEBS (1997).

Schwartzberg, P., et al., "Construction and Analysis of Deletion Mutations in the *pol* Gene of Moloney Murine Leukemia Virus: A New Viral Function Required for Productive Infection," *Cell 37*:1043-1052, MIT Press (1984).

Sooknanan, R., et al., "Fidelity of Nucleic Acid Amplification with Avian Myeloblastosis Virus Reverse Transcriptase and T7 RNA Polymerase," *BioTechniques 17*:1077-1080, 1083-1085, Eaton Publishing Co (1994).

Suzuki, M., et al., "Low Fidelity Mutants in the O-Helix of *Thermus aquaticus* DNA Polymerase I," *J. Biol. Chem. 272*:11228-11235, The American Society for Biochemistry and Molecular Biology, Inc. (1997).

Suzuki, M., et al., "Fidelity Mutants in *Thermus aquaticus* DNA Polymerase I," *Ninth International Genome Sequencing and Analysis Conference*, Hilton Head Island, South Carolina, Sep. 13-16, 1997. *Microbial and Comparative Genomics 2*:226, Abstract C-30, Mary Ann Liebert, Inc. (1997).

Taube, R., et al., "The fidelity of misinsertion and mispair extension throughout DNA synthesis exhibited by mutants of the reverse transcriptase of human immunodeficiency virus type 2 resistant to nucleoside analogs," *Eur. J. Biochem. 250*:106-114, FEBS (1997).

Telesnitsky, A. and Goff, S.P., "RNase H domain mutations affect the interaction between Moloney murine leukemia virus reverse transcriptase and its primer-template," *Proc. Natl. Acad. Sci. USA 90*:1276-1280, The National Academy of Sciences of the USA (1993).

Varela-Echavarria, A., et al., "Comparison of Moloney Murine Leukemia Virus Mutation Rate with the Fidelity of Its Reverse Transcriptase *in Vitro*," *J. Biol. Chem. 267*:24681-24688, American Society for Biochemistry and Molecular Biology (1992).

Wainberg, M.A., et al., "Enhanced Fidelity of 3TC-Selected Mutant HIV-1 Reverse Transcriptase," *Science 271*:1282-1285, American Association for the Advancement of Science (1996).

Co-Pending U.S. Appl. No. 09/677,574, filed Oct. 3, 2000.
Co-Pending U.S. Appl. No. 09/808,124, filed Mar. 15, 2001.
Co-Pending U.S. Appl. No. 09/902,741, filed Jul. 12, 2001.

Pfeiffer, J.K., et al., "Structure-Based Moloney Murine Leukemia Virus Reverse Transcriptase Mutants with Altered Intracellular Direct-Repeat Deletion Frequencies," *J. Virol. 74*:9629-9636, American Society for Microbiology (Oct. 2000).

Jan. 4, 2002, Office Action for U.S. Appl. No. 09/808,124, Potter et al., filed Mar. 15, 2001.
May 22, 2002, Office Action for U.S. Appl. No. 09/808,124, Potter et al., filed Mar. 15, 2001.
Dec. 3, 2002, Office Action for U.S. Appl. No. 09/808,124, Potter et al., filed Mar. 15, 2001.
Aug. 1, 2003, Office Action for U.S. Appl. No. 09/808,124, Potter et al., filed Mar. 15, 2001.
Feb. 5, 2004, Office Action for U.S. Appl. No. 09/808,124, Potter et al., filed Mar. 15, 2001.

Arnold, F.H., et al., "How enzymes adapt: lessons from directed evolution," *TRENDS Biochem. Sci. 26*:100-106, Elsevier Science Ltd. (Feb. 2001).

Bailey, J.M., "Interpretation of Nitrocellulose Filter Assays of Protein-Nucleic Acid Binding," *Anal. Biochem. 93*:204-206, Academic Press, Inc. (1979).

Beard, W.A., et al., "Vertical-scanning Mutagenesis of a Critical Tryptophan in the Minor Groove Binding Track of HIV-1 Reverse Transcriptase. Molecular Nature of Polymerase-Nucleic Acid Interaction," *J. Biol. Chem. 273*:30435-30442, The American Society for Biochemistry and Molecular Biology, Inc. (1998).

Bebenek, K., and Kunkel, T.A., "5. The Fidelity of Retroviral Reverse Transcriptases," in *Reverse Transcriptases*, Skalka, A.M. and Goff, S.P., eds., Cold Spring Harbor Laboratory Press, Plainview, New York, pp. 85-102 (1993).

Bebenek, K., et al., "A minor groove binding track in reverse transcriptase," *Nat. Struct. Biol. 4*:194-197, Nature Publishing Co. (1997).

Cadwell, R.C., and Joyce, G.F., "Randomization of Genes by PCR Mutagenesis," *PCR Meth. Appl. 2*:28-33, Cold Spring Harbor Laboratory Press (1992).

Cambillau, C., and Claverie, J.-M., "Structural and Genomic Correlates of Hyperthermostability," *J. Biol. Chem. 275*:32383-32386, The American Society for Biochemistry and Molecular Biology, Inc. (Oct. 2000).

D'Alessio, J.M., and Gerard, G.F., "Second-strand cDNA synthesis with *E. coli* DNA polymerase I and RNase H: the fate of information at the mRNA 5' terminus and the effect of *E. coli* DNA ligase," *Nucl. Acids Res. 16*:1999-2014, IRL Press Ltd. (1988).

DeStefano, J.J., et al., "Polymerization and RNase H Activities of the Reverse Transcriptases from Avian Myeloblastosis, Human Immunodeficiency, and Moloney Murine Leukemia Viruses Are Functionally Uncoupled," *J. Biol. Chem. 266*:7423-7431, The American Society for Biochemistry and Molecular Biology, Inc. (1991).

DeStefano, J.J., et al., "Characterization of an RNase H deficient mutant of human immunodeficiency virus-1 reverse transcriptase having an aspartate to asparagine change at position 498," *Biochim. Biophys. Acta 1219*:380-388, Elsevier Science B.V. (1994).

Ding, J., et al., "Structure and Functional Implications of the Polymerase Active Site Region in a Complex of HIV-1 RT with a Double-stranded DNA Template-primer and an Antibody Fab Fragment at 2.8 Å Resolution," *J. Mol. Biol. 284*:1095-1111, Academic Press, Inc. (1998).

Georgiadis, M.M., et al., "Mechanistic implications from the structure of a catalytic fragment of Moloney murine leukemia virus reverse transcriptase," *Structure 3*:879-892, Current Biology Ltd. (1995).

Gerard, G.F., et al., "Poly(2'-o-methylcytidylate) Oligodeoxyguanylate as a Template for the Ribonucleic Acid Directed Deoxyribonucleic Acid Polymerase in Ribonucleic Acid Tumor Virus Particles and a Specific Probe for the Ribonucleic Acid Directed Enzyme in Transformed Murine Cells," *Biochem. 13*:1632-1641, The American Chemical Society (1974).

Gerard, G.F., and D'Alessio, J.M., "Reverse Transcriptase (EC 2.7.7.49). The Use of Cloned Moloney Murine Leukemia Virus Reverse Transcriptase to Synthesize DNA from RNA," in *Methods in Molecular Biology*, vol. 16: *Enzymes of Molecular Biology*, Burrell, M.M., ed., Humana Press, Totowa, NJ, pp. 73-93 (1993).

Gerard, G.F., et al., "Reverse Transcriptase. The Use of Cloned Moloney Murine Leukemia Virus Reverse Transcriptase to Synthesize DNA from RNA," *Mol. Biotechnol.* 8:61-77, Humana Press (1997).

Harrison, G.P., et al., "Pausing of reverse transcriptase on retroviral RNA templates is influenced by secondary structures both 5' and 3' of the catalytic site," *Nucl. Acids Res.* 26:3433-3442, Oxford University Press (1998).

Houts, G.E., et al., "Reverse Transcriptase from Avian Myeloblastosis Virus," *J. Virol.* 29:517-522, American Society for Microbiology (1979).

Huang, H., et al., "Structure of a Covalently Trapped Catalytic Complex of HIV-1 Reverse Transcriptase: Implications for Drug Resistance," *Science* 282:1669-1675, American Association for the Advancement of Science (1998).

Jacobo-Molina, A., et al., "Crystal structure of human immunodeficiency virus type 1 reverse transcriptase complexed with double-stranded DNA at 3.0 Å resolution shows bent DNA," *Proc. Natl. Acad. Sci.(USA)* 90:6320-6324, National Academy of Sciences of the USA (1993).

Kohlstaedt, L.A., et al., "Crystal Structure at 3.5 Å Resolution of HIV-1 Reverse Transcriptase Complexed with an Inhibitor," *Science* 256:1783-1790, American Association for the Advancement of Science (1992).

Kotewicz, M.L., et al., "Isolation of cloned Moloney murine leukemia virus reverse transcriptase lacking ribonuclease H activity," *Nucl. Acids Res.* 16:265-277, IRL Press Ltd. (1988).

Kneller, D.G., et al., "Improvements in Protein Secondary Structure Prediction by An Enhanced Neural Network," *J. Mol. Biol.* 214:171-182, Academic Press Ltd. (1990).

Krug, M.S., and Berger, S.L., "[33] First-Strand cDNA Synthesis Primed with Oligo (dT)," *Meth. Enzymol.* 152:316-325, Academic Press, Inc. (1987).

Kumar, S., and Nussinov, R., "How do thermophilic proteins deal with heat?" *Cell. Mol. Life Sci.* 58:1216-1233, Birkhauser Verlag (Aug. 2001).

Kunkel, T.A., et al., "[19] Rapid and Efficient Site-Specific Mutagenesis without Phenotypic Selection," *Meth. Enzymol.* 154:367-383, Academic Press, Inc. (1987).

Kunkel, T.A., et al., "[6] Efficient Site-Directed Mutagenesis Using Uracil-Containing DNA," *Meth. Enzymol.* 204:125-139, Academic Press, Inc. (1991).

Le Grice, S.F.J., "9. Human Immunodeficiency Virus Reverse Transcriptase," in *Reverse Transcripase,* Skalka, A.M. and Goff, S.P., eds., Cold Spring Harbor Laboratory Press, Plainview, NY, pp. 163-191 (1993).

Lehmann, M., and Wyss, M., "Engineering proteins for thermostability: the use of sequence alignments versus rational design and directed evolution," *Curr. Opin. Biotechnol.* 12:371-375, Elsevier Science Ltd. (Aug. 2001).

Leung, D.W., et al., "A Method for Random Mutagenesis of a Defined DNA Segment Using a Modified Polymerase Chain Reaction," *Technique* 1:11-15, W.B. Saunders Co. (1989).

McDonell, M.W., et al., "Analysis of Restriction Fragments of T7 DNA and Determination of Molecular Weights by Electrophoresis in Neutral and Alkaline Gels," *J. Mol. Biol.* 110:119-146, Academic Press, Inc. (1977).

Mölling, K., et al., "Association of Viral Reverse Transcriptase with an Enzyme degrading the RNA Moiety of RNA-DNA Hybrids," *Nature New Biology* 234:240-243, Macmillan Journals Ltd. (1971).

Myers, T.W., and Gelfand, D.H., "Reverse Transcription and DNA Amplification by a *Thermus thermophilus* DNA Polymerase," *Biochem* 30:7661-7666, The American Chemical Society (1991).

Polesky, A.H., et al., "Identification of Residues Critical for the Polymerase Activity of the Klenow Fragment of DNA Polymerase I from *Escherichia coli,*" *J. Biol. Chem.* 265:14579-14591, The American Society for Biochemistry and Molecular Biology, Inc. (1990).

Prasad, V.R., "8. Genetic Analysis of Retroviral Reverse Transcriptase Structure and Function," in *Reverse Transcripase,* Skalka, A.M. and Goff, S.P., eds., Cold Spring Harbor Laboratory Press, Plainview, NY, pp. 135-162 (1993).

Rost, B., "[31] PHD: Predicting One-Dimensional Protein Structure by Profile-Based Neural Networks," *Meth. Enzymol.* 266:525-539, Academic Press, Inc. (1996).

Shinnick, T.M., et al., "Nucleotide sequence of Moloney murine leukaemia virus," *Nature* 293:543-548, Macmillan Journals Ltd. (1981).

Skalka, A.M., "10. Endonuclease Activity Associated with Reverse Transcriptase of Avian Sarcoma-Leukosis Viruses," in *Reverse Transcripase,* Skalka, A.M. and Goff, S.P., eds., Cold Spring Harbor Laboratory Press, Plainview, NY, pp. 193-204 (1993).

Stemmer, W.P.C., "Rapid evolution of a protein *in vitro* by DNA shuffling," Nature 370:389-391, Macmillan Journals Ltd. (1994).

Strauss, H.S., et al., "Variables affecting the selectivity and efficiency of retention of DNA fragments by *E. coli* RNA polymerase in the nitrocellulose-filter-binding assay," *Gene* 13:75-87, Elsevier/North-Holland Biomedical Press (1981).

Tosh, C., et al., "One-Tube and One-Buffer System of RT-PCR Amplification of 1D Gene of Foot-and-Mouth Disease Virus Field Isolates," *Acta Virol.* 41:153-155, Slovak Academic Press (1997).

Verma, I., et al., "Studies on Reverse Transcriptase of RNA Tumor Viruses. III. Properties of Purified Moloney Murine Leukemia Virus DNA Polymerase and Associated RNase H," *J. Virol.* 15:843-854, American Society for Microbiology (1975).

Wells, J.A., "Additivity of Mutational Effects in Proteins," *Biochem.* 29:8509-8517, The American Chemical Society (1990).

Wu, W., et al., "Human Immunodeficiency Virus Type 1 Nucleocapsid Protein Reduces Reverse Transcriptase Pausing at a Secondary Structure near the Murine Leukemia Virus Polypurine Tract," *J. Virol.* 70:7132-7142, American Society for Microbiology (1996).

International Search Report for International Patent Application No. PCT/US03/28802, mailed Mar. 18, 2005, ISA/US, Alexandria, VA.

* cited by examiner

```
                                                                    1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val

1258
TCC ATA AAA CAA TAC CCC ATG TCA CAA GAA GCC AGA CTG GGG ATC AAG CCC CAC ATA CAG
Ser Ile Lys Gln Tyr Pro MET Ser Gln Glu Ala Arg Leu Gly Ile Lys Pro His Ile Gln

1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu

1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg
```

FIG 7A

```
                                                                                              1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile

1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe

1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu

1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly

1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala

1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp

1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln

1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu

2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp
```

FIG 7B

```
                                                                                    2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT AAT TCC
Pro Ala Thr Leu Leu Pro Leu Pro Glu Glu Gly Leu Gln His Asn Cys Leu Asp Asn Ser

2533
CGC TTA ATT AAT TAA
Arg Leu Ile Asn
```

FIG 7C

THERMOSTABLE REVERSE TRANSCRIPTASES AND USES THEREOF

CROSS-REFERENCE TO RELATED APPLICATIONS

The present application claims the benefit of U.S. Provisional Appl. No. 60/207,196, filed May 26, 2000, the entire disclosure of which is incorporated herein by reference.

BACKGROUND OF THE INVENTION

1. Field of the Invention

The present invention is in the fields of molecular and cellular biology. The invention is generally related to reverse transcriptase enzymes and methods for the reverse transcription of nucleic acid molecules, especially messenger RNA molecules. Specifically, the invention relates to reverse transcriptase enzymes which have been mutated or modified to increase thermostability, decrease terminal deoxynucleotidyl transferase activity, and/or increase fidelity, and to methods of producing, amplifying or sequencing nucleic acid molecules (particularly cDNA molecules) using these reverse transcriptase enzymes or compositions. The invention also relates to nucleic acid molecules produced by these methods and to the use of such nucleic acid molecules to produce desired polypeptides. The invention also concerns kits or compositions comprising such enzymes.

2. Related Art cDNA and cDNA Libraries

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is typically manifested upon production of the protein which the gene encodes. In order to produce a protein, a complementary copy of one strand of the DNA double helix is produced by RNA polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist myriad mRNA species, each encoding a separate and specific protein. This fact provides a powerful tool to investigators interested in studying genetic expression in a tissue or cell. mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or agarose, to which oligomers of thymidine (T) have been complexed. Since the 3' termini on most eukaryotic mRNA molecules contain a string of adenosine (A) bases, and since A base pairs with T, the mRNA molecules can be rapidly purified from other molecules and substances in the tissue or cell extract. From these purified mRNA molecules, cDNA copies may be made using the enzyme reverse transcriptase (RT), which results in the production of single-stranded cDNA molecules. This reaction is typically referred to as the first strand reaction. The single-stranded cDNAs may then be converted into a complete double-stranded DNA copy (i.e., a double-stranded cDNA) of the original mRNA (and thus of the original double-stranded DNA sequence, encoding this mRNA, contained in the genome of the organism) by the action of a DNA polymerase. The protein-specific double-stranded cDNAs can then be inserted into a plasmid or viral vector, which is then introduced into a host bacterial, yeast, animal or plant cell. The host cells are then grown in culture media, resulting in a population of host cells containing (or in many cases, expressing) the gene of interest.

This entire process, from isolation of mRNA from a source organism or tissue to insertion of the cDNA into a plasmid or vector to growth of host cell populations containing the isolated gene, is termed "cDNA cloning." The set of cDNAs prepared from a given source of mRNAs is called a "cDNA library." The cDNA clones in a cDNA library correspond to the genes transcribed in the source tissue. Analysis of a cDNA library can yield much information on the pattern of gene expression in the organism or tissue from which it was derived.

Retroviral Reverse Transcriptase Enzymes

Three prototypical forms of retroviral reverse transcriptase have been studied thoroughly. Moloney Murine Leukemia Virus (M-MLV) reverse transcriptase contains a single subunit of 78 kDa with RNA-dependent DNA polymerase and RNase H activity. This enzyme has been cloned and expressed in a fully active form in *E. coli* (reviewed in Prasad, V. R., *Reverse Transcriptase*, Cold Spring Harbor, N.Y.: Cold Spring Harbor Laboratory Press, p.135 (1993)). Human Immunodeficiency Virus (HIV) reverse transcriptase is a heterodimer of p66 and p51 subunits in which the smaller subunit is derived from the larger by proteolytic cleavage. The p66 subunit has both a RNA-dependent DNA polymerase and an RNase H domain, while the p51 subunit has only a DNA polymerase domain. Active HIV p66/p51 reverse transcriptase has been cloned and expressed successfully in a number of expression hosts, including *E. coli* (reviewed in Le Grice, S. F. J., *Reverse Transcriptase*, Cold Spring Harbor, N.Y.: Cold Spring Harbor Laboratory press, p. 163 (1993)). Within the HIV p66/p51 heterodimer, the 51-kD subunit is catalytically inactive, and the 66-kD subunit has both DNA polymerase and RNase H activity (Le Grice, S. F. J., et al., *EMBO Journal* 10:3905 (1991); Hostomsky, Z., et al., *J. Virol.* 66:3179 (1992)). Avian Sarcoma-Leukosis Virus (ASLV) reverse transcriptase, which includes but is not limited to Rous Sarcoma Virus (RSV) reverse transcriptase, Avian Myeloblastosis Virus (AMV) reverse transcriptase, Avian Erythroblastosis Virus (AEV) Helper Virus MCAV reverse transcriptase, Avian Myelocytomatosis Virus MC29 Helper Virus MCAV reverse transcriptase, Avian Reticuloendotheliosis Virus (REV-T) Helper Virus REV-A reverse transcriptase, Avian Sarcoma Virus UR2 Helper Virus UR2AV reverse transcriptase, Avian Sarcoma Virus Y73 Helper Virus YAV reverse transcriptase, Rous Associated Virus (RAV) reverse transcriptase, and Myeloblastosis Associated Virus (MAV) reverse transcriptase, is also a heterodimer of two subunits, α (approximately 62 kDa) and β (approximately 94 kDa), in which α is derived from β by proteolytic cleavage (reviewed in Prasad, V. R., *Reverse Transcriptase*, Cold Spring Harbor, N.Y.: Cold Spring Harbor Laboratory Press (1993), p. 135). ASLV reverse transcriptase can exist in two additional catalytically active structural forms, ββ and α (Hizi, A. and Joklik, W. K., *J. Biol. Chem.* 252: 2281 (1977)). Sedimentation analysis suggests αβ and ββ are dimers and that the α form exists in an equilibrium between monomeric and dimeric forms (Grandgenett, D. P., et al., *Proc. Nat. Acad. Sci. USA* 70:230 (1973); Hizi, A. and Joklik, W. K., *J. Biol. Chem.* 252:2281 (1977); and Soltis, D. A. and Skalka, A. M., *Proc. Nat. Acad. Sci. USA* 85:3372 (1988)). The ASLV αβ and ββ reverse transcriptases are the only known examples of retroviral reverse transcriptase that include three different activities in the same protein complex: DNA polymerase, RNase H, and DNA endonuclease (integrase) activities (reviewed in Skalka, A. M., *Reverse Transcriptase*, Cold Spring Harbor, N.Y.: Cold Spring Harbor Laboratory Press (1993), p. 193). The α form lacks the integrase domain and activity.

Various forms of the individual subunits of ASLV reverse transcriptase have been cloned and expressed. These include a 98-kDa precursor polypeptide that is normally processed proteolytically to β and a 4 kDa polypeptide removed from the β carboxy end (Alexander, F., et al., *J. Virol.* 61:534 (1987) and Anderson, D. et al., *Focus* 17:53 (1995)), and the mature β subunit (Weis, J. H. and Salstrom, J. S., U.S. Pat. No. 4,663,290 (1987); and Soltis, D. A. and Skalka, A. M., *Proc. Nat. Acad. Sci. USA* 85:3372 (1988)). (See also Werner S. and Wohrl B. M., *Eur. J. Biochem.* 267:4740–4744 (2000); Werner S. and Wohrl B. M., *J. Virol.* 74:3245–3252 (2000); Werner S. and Wohrl B. M., *J. Biol. Chem.* 274:26329–26336 (1999).) Heterodimeric RSV αβ reverse transcriptase has also been purified from *E. coli* cells expressing a cloned RSV β gene (Chernov, A. P., et al., *Biomed. Sci.* 2:49 (1991)).

Reverse Transcription Efficiency

As noted above, the conversion of mRNA into cDNA by reverse transcriptase-mediated reverse transcription is an essential step in the study of proteins expressed from cloned genes. However, the use of unmodified reverse transcriptase to catalyze reverse transcription is inefficient for a number of reasons. First, reverse transcriptase sometimes degrades an RNA template before the first strand reaction is initiated or completed, primarily due to the intrinsic RNase H activity present in reverse transcriptase. In addition, mis-priming of the mRNA template molecule can lead to the introduction of errors in the cDNA first strand while secondary structure of the mRNA molecule itself may make some mRNAs refractory to first strand synthesis.

Removal of the RNase H activity of reverse transcriptase can eliminate the first problem and improve the efficiency of reverse transcription (Gerard, G. F., et al., *FOCUS* 11(4):60 (1989); Gerard, G. F., et al., *FOCUS* 14(3):91 (1992)). However such reverse transcriptases ("RNase H–" forms) do not address the additional problems of mis-priming and mRNA secondary structure.

Another factor which influences the efficiency of reverse transcription is the ability of RNA to form secondary structures. Such secondary structures can form, for example, when regions of RNA molecules have sufficient complementarity to hybridize and form double stranded RNA. Generally, the formation of RNA secondary structures can be reduced by raising the temperature of solutions which contain the RNA molecules. Thus, in many instances, it is desirable to reverse transcribe RNA at temperatures above 37° C. However, art known reverse transcriptases generally lose activity when incubated at temperatures much above 37° C. (e.g., 50° C.).

SUMMARY OF THE INVENTION

The present invention provides reverse transcriptase enzymes, compositions comprising such enzymes and methods useful in overcoming limitations of reverse transcription discussed above. In general, the invention provides compositions for use in reverse transcription of a nucleic acid molecule comprising one or more (e.g., one, two, three, four, five, ten, fifteen, etc.) polypeptides having reverse transcriptase activity of the invention. Such compositions may further comprise one or more (e.g., one, two, three, four, five, etc.) nucleotides, a suitable buffer, and/or one or more (e.g., one, two, three, four, five, ten, fifteen, etc.) DNA polymerases. The compositions of the invention may also comprise one or more (e.g., one, two, three, four, five, ten, fifteen, etc.) oligonucleotide primers.

The reverse transcriptases of the invention are preferably modified or mutated such that the thermostability of the enzyme is increased or enhanced. In specific embodiments, the reverse transcriptases of the invention may be single chained (single subunit) or multi-chained (multi-subunit) and may be reduced or substantially reduced in RNase H activity. Preferably enzymes of the invention are enzymes selected from the group consisting of Moloney Murine Leukemia Virus (M-MLV) RNase H– reverse transcriptase, Rous Sarcoma Virus (RSV) RNase H– reverse transcriptase, Avian Myeloblastosis Virus (AMV) RNase H– reverse transcriptase, Rous Associated Virus (RAV) RNase H– reverse transcriptase, Myeloblastosis Associated Virus (MAV) RNase H– reverse transcriptase or other ASLV RNase H– reverse transcriptases and Human Immunodeficiency Virus (HIV) RNase H– reverse transcriptase and mutants thereof. In preferred compositions, the reverse transcriptases are present at working concentrations.

In certain aspects, the invention includes reverse transcriptases which have been modified or mutated to increase or enhance thermostability. Examples of such reverse transcriptases include enzymes having one or more modifications or mutations at positions corresponding to amino acids selected from the group consisting of:

(a) leucine 52 of M-MLV reverse transcriptase;
(b) tyrosine 64 of M-MLV reverse transcriptase;
(c) lysine 152 of M-MLV reverse transcriptase;
(d) histidine 204 of M-MLV reverse transcriptase;
(e) methionine 289 of M-MLV reverse transcriptase; and
(f) threonine 306 of M-MLV reverse transcriptase.

In specific embodiments, the invention is directed to M-MLV reverse transcriptases wherein leucine 52 is replaced with proline, tyrosine 64 is replaced with arginine, lysine 152 is replaced with methionine, histidine 204 is replaced with arginine, methionine 289 is replaced with leucine, and/or threonine 306 is replaced with either lysine or arginine. Further included within the scope of the invention are reverse transcriptases, other than M-MLV reverse transcriptase, which contain alterations corresponding to those set out above.

In additional aspects, the invention also include thermostable reverse transcriptases which retain at least about 50%, at least about 60%, at least about 70%, at least about 85%, at least about 95%, at least about 97%, at least about 98%, at least about 99%, or at least about 100% of reverse transcriptase activity after heating to 50° C. for 5 minutes.

As noted above, enzymes of the invention include reverse transcriptases which exhibit reverse transcriptase activity either upon the formation of multimers (e.g., dimers) or as individual protein molecules (i.e., in monomeric form). Examples of reverse transcriptases which exhibit reverse transcriptase activity upon the formation of multimers include AMV, RSV and HIV reverse transcriptases. One example of a reverse transcriptase which exhibits reverse transcriptase activity as separate, individual proteins (i.e., in monomeric form) is M-MLV reverse transcriptase.

Multimeric reverse transcriptases of the invention may form homo-multimers or hetero-multimers. In other words, the subunits of the multimeric protein complex may be identical or different. One example of a hetero-dimeric reverse transcriptase is AMV reverse transcriptase, which is composed of two subunits that differ in primary amino acid sequence. More specifically, as already discussed, AMV reverse transcriptase may be composed of two subunits wherein one of these subunits is generated by proteolytic processing of the other. Thus, dimeric AMV reverse transcriptase may be composed of subunits of differing size which share regions of amino acid sequence identity.

The present invention relates in particular to mutant or modified reverse transcriptases wherein one or more (e.g., one, two, three, four, five, ten, twelve, fifteen, twenty, etc.) amino acid changes have been made which renders the enzyme more thermostable in nucleic acid synthesis, as compared to the unmutated or unmodified reverse transcriptases. Sites for mutation or modification to produce the thermostable reverse transcriptase enzymes of the present invention and/or reverse transcriptases which exhibit other characteristics (e.g., increased fidelity, decreased TdT activity, etc.) are listed for some reverse transcriptases in Table 1. The modifications described in Table 1 preferably produce thermostable reverse transcriptases of the invention. Similar or equivalent sites or corresponding sites in other reverse transcriptases can be mutated or modified to produce additional thermostable reverse transcriptases, as well as reverse transcriptases which exhibit other characteristics (e.g., increased fidelity, decreased TdT activity, etc.).

TABLE 1

| RT | Amino Acids |
|---|---|
| M-MLV | L52, Y64, L135, H143, K152, Q165, G181, |
|  | H204, I218, N249, M289, |
|  | T306, A517, D524, T544, V546, W548, |
|  | E562, H577, D583, L604, |
|  | S606, G608, F625, L626, H629, H631, H638, G641 |
| AMV | V2, L4, W12, P14, H16, T17, W20, I21, Q23, W24, |
|  | L26, P27, G29, |
|  | V32, Q36, L42, Q43, L44, G45, H46, I47, |
|  | P49, S50, L51, S52, C53, |
|  | W54, P59, I61, A64, S65, G66, S67, Y68, L70, |
|  | L71, A76, A79, P83, |
|  | A86, V87, Q88, Q89, G90, A91, WI01, P102, |
|  | L108, Q120, S131, |
|  | V132, N133, N134, Q135, P137, A138, Q142, |
|  | Q148, T151, Y180, |
|  | M181, S190, H191, G193, A196, I201, S202, |
|  | P214, V217, Q218, P221, |
|  | G222, Q224, L226, G227, Y228, G231, T233, |
|  | Y234, A236, P237, |
|  | G239, L240, P244, I246, T248, W250, Q252, |
|  | G257, Q260, W261, |
|  | P264, L266, G267, L272, Y277, Q279, L280, |
|  | G282, 8283, P285, N286, |
|  | A288, N292, L293, M297, I302, V303, L305, |
|  | S306, T308, L311, L320, |
|  | I332, G333, V334, G336, Q337, G338, P345, |
|  | W348, L349, P350, 8351, |
|  | P354, A357, F358, A360, W361, L362, V364, |
|  | L365, T366, T370, A374, |
|  | V377, G381, C392, P400, G402, L405, G412, |
|  | I414, F423, I425, A426, |
|  | P428, L433, H440, P441, V443, G444, P445, |
|  | A451, S453, 8454, T455, |

TABLE 1-continued

| RT | Amino Acids |
|---|---|
|  | H456, G458, V459, V460, W462, W468, I470, |
|  | I473, A474, L476, |
|  | G477, A478, 8479, V480, Q481, Q482, L483, |
|  | A491, W495, P496, |
|  | T497, T498, P499, T500, A507, F508, M512, |
|  | L513, G520, V521, P522, |
|  | S523, T524, A525, A527, F528, L534, S535, |
|  | Q536, S538, V543, 8548, |
|  | H549, 8550, V552, P553, P556, |
|  | T557, N560, A562 |
| RSV | V2, L4, W12, P14, H16, T17, W20, I21, Q23, |
|  | W24, L26, P27, G29, |
|  | V32, Q36, L42, Q43, L44, G45, I146, I47, P49, |
|  | S50, L51, S52, C53, |
|  | W54, F59, I61, A64, S65, G66, S67, Y68, |
|  | L70, L71, A76, A79, P83, |
|  | A86, V87, Q88, Q89, G90, A91, W101, |
|  | P102, L108, Q120, S131, |
|  | V132, N133, N134, Q135, P137, A138, Q142, |
|  | Q148, T151, Y180, |
|  | M181, S190, H191, G193, A196, I201, S202, |
|  | P214, V217, Q218, P221, |
|  | G222, Q224, L226, G227, Y228, G231, |
|  | T233, Y234, A236, P237, |
|  | G239, L240, P244, I246, T248, W250, |
|  | Q252, G257, Q260, W261, |
|  | P264, L266, G267, L272, Y277, Q279, |
|  | L280, G282, 8283, P285, N286, |
|  | A288, N292, L293, M297, I302, V303, |
|  | L305, 8306, T308, L311, L320, |
|  | I332, G333, V334, G336, Q337, G338, |
|  | P345, W348, L349, F350, S351, |
|  | P354, A357, P3S8, A360, W361, L362, |
|  | V364, L365, T366, T370, A374, |
|  | V377, G381, C392, P400, G402, L405, |
|  | G412, I414, P423, 1425, A426, |
|  | P428, L433, H440, P441, V443, G444, |
|  | P445, A451, S453, S454, T455, |
|  | H456, G458, V459, V460, W462, W468, |
|  | I470, I473, A474, L476, |
|  | G477, A478, S479, V480, Q481, Q482, |
|  | L483, A491, W495, P496, |
|  | T497, T498, P499, T500, A507, E508, |
|  | M512, L513, G520, V521, P522, |
|  | S523, T524, A525, A527, F528, L534, |
|  | S535, Q536, S538, V543, S548, |
|  | H549, S550, V552, P553, F556, T557, N560, A562 |
| HIV | I1, P3, L11, P13, G14, M15, Q22, W23, L25, |
|  | T26, T38, G44, I46, S47, |
|  | G50, P51, N53, P54, Y55, F60, I62, S67, |
|  | T68, W70, L73, V89, |
|  | Q90L91, G92, I93, S104, V110, G111, S133, |
|  | I134, N135, N136, P139, |
|  | G140, I141, Q144, N146, Q150,, Y182, |
|  | M183, I194, G195, Q196, |
|  | T,199, Q206, L209, P216, Q221, P224, |
|  | P225, L227, M229, G230, |
|  | Y231, H234, Q241, P242, V244, L245, S250, |
|  | T252, N254, Q257, G261, |
|  | N264, W265, Q268, P271, G272, Q277, |
|  | C279, L281, L282, Q284, |
|  | T285, A287, L288, T289, V291, P293, |
|  | L294, T295, L300, A303, I308, |
|  | L309, P312, H314, Y317, L324, I328, |
|  | Q329, G332, Q333, G334, Y341, |
|  | P344, F345, Y353, M356, G358, A359, |
|  | H360, T361, Q372, T376, |
|  | V380, Q392, W405, Q406, A407, F415, |
|  | V416, N417, T418, P419, |
|  | P420, L424, W425, P432, V434, G435, |
|  | A436, A444, A445, N446, |
|  | T449, L451, N459, G461, Q463, V465, |
|  | V466, P467, L468, T469, N470, |
|  | T471, T472, N473, Q474, Y482, Q486, |
|  | 5488, G489, L490, Q499, |
|  | Y500, G503, I504, S512, S514, |
|  | L516, N518, Q519, Q523, 1525, W534, |

TABLE 1-continued

| RT | Amino Acids |
|---|---|
| | P536, A537, H538, G540, I541, G542, Q546, L550, S552, A553, V554, I555 |

Those skilled in the art will appreciate that a different isolate of virus may encode a reverse transcriptase enzyme having a different amino acid at the positions identified above. Such isolates may be modified to produce the thermostable reverse transcriptases of the present invention.

Thermostable reverse transcriptases of the invention may also have one or more properties: (a) reduced or substantially reduced RNase H activity, (b) reduced or substantially reduced terminal deoxynucleotidyl transferase activity, and/or (c) increased fidelity.

Enzymes of the invention which have reduced or substantially reduced terminal deoxynucleotidyl transferase activity may have one or more modifications or mutations at positions corresponding to amino acids selected from the group consisting of:

(a) tyrosine 133 of M-MLV reverse transcriptase;
(b) threonine 197 of M-MLV reverse transcriptase; and
(c) phenylalanine 309 of M-MLV reverse transcriptase.

In specific embodiments, the invention is directed to M-MLV reverse transcriptases wherein tyrosine 133 is replaced with alanine, threonine 197 is replaced with glutamic acid, and/or phenylalanine 309 is replaced with asparagine. Further included within the scope of the invention are reverse transcriptases, other than M-MLV reverse transcriptase, which contain alterations corresponding to those set out above.

Additionally, enzymes which have exhibit increased fidelity may have one or more modifications or mutations at positions corresponding to amino acids selected from the group consisting of:

(a) tyrosine 64 of M-MLV reverse transcriptase;
(b) arginine 116 of M-MLV reverse transcriptase;
(c) glutamine 190 of M-MLV reverse transcriptase; and
(d) valine 223 of M-MLV reverse transcriptase.

In specific embodiments, reverse transcriptases of the invention may not include M-MLV reverse transcriptases, HIV reverse transcriptases, AMV reverse transcriptases, and/or RSV reverse transcriptases. Thus, for example, in certain embodiments, the invention is directed to reverse transcriptases with increased thermostability that are not a HIV reverse transcriptase. In other embodiments, the invention is directed to reverse transcriptases with increased thermostability that are not a M-MLV reverse transcriptase. In yet other embodiments, the invention is directed to reverse transcriptases with increased thermostability that are not an AMV reverse transcriptase. In still other embodiments, the invention is directed to reverse transcriptases with increased thermostability that are not a RSV reverse transcriptase.

The present invention is also directed to nucleic acid molecules (e.g., vectors) containing a gene or nucleic acid encoding the mutant or modified reverse transcriptases of the present invention and to host cells containing such DNA or other nucleic acid molecules. Any number of hosts may be used to express the gene or nucleic acid molecule of interest, including prokaryotic and eukaryotic cells. In specific embodiments, prokaryotic cells are used to express the reverse transcriptases of the invention. One example of a prokaryotic host suitable for use with the present invention is *Escherichia coli*. Examples of eukaryotic hosts suitable for use with the present invention include fungal cells (e.g., *Saccharomyces cerevisiae* cells, *Pichia pastoris* cells, etc.), plant cells, and animal cells (e.g., *Drosophila melanogaster* cells, *Spodoptera frugiperda* Sf9 and Sf21 cells, Trichoplusa High-Five cells, *C. elegans* cells, *Xenopus laevis* cells, CHO cells, COS cells, VERO cells, BHK cells, etc.).

The invention also relates to a method of producing the reverse transcriptases of the invention, said method comprising:

(a) culturing a host cell comprising a gene or other nucleic acid molecule encoding a reverse transcriptase of the invention (preferably such reverse transcriptase gene or other nucleic acid molecule is contained by a vector within the host cell);
(b) expressing the gene or nucleic acid molecule; and
(c) isolating said reverse transcriptase from the host cell.

The invention is also directed to methods for making one or more (e.g., one, two, three, four, five, ten, twelve, fifteen, etc.) nucleic acid molecules, comprising mixing one or more (e.g., one, two, three, four, five, ten, twelve, fifteen, etc.) nucleic acid templates (preferably one or more RNA templates and most preferably one or more messenger RNA templates) with one or more (e.g., one, two, three, four, five, ten, fifteen, etc.) reverse transcriptases of the invention and incubating the mixture under conditions sufficient to make a first nucleic acid molecule or molecules complementary to all or a portion of the one or more nucleic acid templates. In some embodiments, the mixture is incubated at an elevated temperature. In specific embodiments, the elevated temperature may be from about 40° C. or greater, from about 45° C. or greater, from about 50° C. or greater, from about 51° C. or greater, from about 52° C. or greater, from about 53° C. or greater, from about 54° C. or greater, from about 55° C. or greater, from about 56° C. or greater, from about 57° C. or greater, from about 58° C. or greater, from about 59° C. or greater, from about 60° C. or greater, from about 61° C. or greater, from about 62° C. or greater, from about 63° C. or greater, from about 64° C. or greater, from about 65° C. or greater, from about 66° C. or greater, from about 67° C. or greater, from about 68° C. or greater, from about 69° C. or greater, from about 70° C. or greater, from about 71° C. or greater, from about 72° C. or greater, from about 73° C. or greater, from about 74° C. or greater, from about 75° C. or greater, from about 76° C. or greater, from about 77° C. or greater, or from about 78° C. or greater; or at a temperature range of from about 37° C. to about 75° C., from about 40° C. to about 75° C., from about 45° C. to about 75° C., from about 50° C. to about 75° C., from about 51° C. to about 75° C., from about 52° C. to about 75° C., from about 53° C. to about 75° C., from about 54° C. to about 75° C., from about 55° C. to about 75° C. In other embodiments, the elevated temperature is within the range of about 50° C. to about 70° C., from about 51° C. to about 70° C., from about 52° C. to about 70° C., from about 53° C. to about 70° C., from about 54° C. to about 70° C., from about 55° C. to about 70° C., from about 55° C. to about 65° C., from about 56° C. to about 65° C., from about 56° C. to about 64° C. or about 56° C. to about 62° C., from about other embodiments, the elevated temperature may be within the range of about 45° C. to about 60° C., from about 46° C. to about 60° C., from about 47° C. to about 60° C., from about 48° C. to about 60° C., from about 49° C. to about 60° C., from about 50° C. to about 60° C., from about 51° C. to about 60° C., from about 52° C. to about 60° C., from about 53° C. to about 60° C., or from about 54° C. to about 60° C. In additional specific embodiments, the first nucleic acid molecule is a single-stranded cDNA.

Nucleic acid templates suitable for reverse transcription according to this aspect of the invention include any nucleic acid molecule or population of nucleic acid molecules (preferably RNA and most preferably mRNA), particularly those derived from a cell or tissue. In a specific aspect, a population of mRNA molecules (a number of different mRNA molecules, typically obtained from a particular cell or tissue type) is used to make a cDNA library, in accordance with the invention. Examples of cellular sources of nucleic acid templates include bacterial cells, fungal cells, plant cells and animal cells.

The invention also concerns methods for making one or more (e.g., one, two, three, four, five, ten, twelve, fifteen, etc.) double-stranded nucleic acid molecules. Such methods comprise (a) mixing one or more nucleic acid templates (preferably RNA or mRNA, and more preferably a population of mRNA templates) with one or more (e.g., one, two, three, four, five, ten, fifteen, etc.) reverse transcriptases of the invention; (b) incubating the mixture under conditions sufficient to make a first nucleic acid molecule or molecules complementary to all or a portion of the one or more templates; and (c) incubating the first nucleic acid molecule or molecules under conditions sufficient to make a second nucleic acid molecule or molecules complementary to all or a portion of the first nucleic acid molecule or molecules, thereby forming one or more double-stranded nucleic acid molecules comprising the first and second nucleic acid molecules. In some embodiments, the incubation of step (b) is performed at an elevated temperature. In specific embodiments, the elevated temperature may be from about 40° C. or greater, from about 45° C. or greater, from about 50° C. or greater, from about 51° C. or greater, from about 52° C. or greater, from about 53° C. or greater, from about 54° C. or greater, from about 55° C. or greater, from about 56° C. or greater, from about 57° C. or greater, from about 58° C. or greater, from about 59° C. or greater, from about 60° C. or greater, from about 61° C. or greater, from about 62° C. or greater, from about 63° C. or greater, from about 64° C. or greater, from about 65° C. or greater, from about 66° C. or greater, from about 67° C. or greater, from about 68° C. or greater, from about 69° C. or greater, from about 70° C. or greater, from about 71° C. or greater, from about 72° C. or greater, from about 73° C. or greater, from about 74° C. or greater, from about 75° C. or greater, from about 76° C. or greater, from about 77° C. or greater, or from about 78° C. or greater; or at a temperature range of from about 37° C. to about 75° C., from about 40° C. to about 75° C., from about 45° C. to about 75° C., from about 50° C. to about 75° C., from about 51° C. to about 75° C., from about 52° C. to about 75° C., from about 53° C. to about 75° C., from about 54° C. to about 75° C., or from about 55° C. to about 75° C. In some embodiments, the elevated temperature is within the range of from about 50° C. to about 70° C., from about 51° C. to about 70° C., from about 52° C. to about 70° C., from about 53° C. to about 70° C., from about 54° C. to about 70° C., from about 55° C. to about 70° C., from about 55° C. to about 65° C., from about 56° C. to about 65° C., from about 56° C. to about 64° C., or from about 56° C. to about 62° C. In other embodiments, the elevated temperature may be within the range of from about 45° C. to about 60° C., from about 46° C. to about 60° C., from about 47° C. to about 60° C., from about 48° C. to about 60° C., from about 49° C. to about 60° C., from about 50° C. to about 60° C., from about 51° C. to about 60° C., from about 52° C. to about 60° C., from about 53° C. to about 60° C., or from about 54° C. to about 60° C. Such methods may include the use of one or more (e.g., one, two, three, four, five, ten, twelve, fifteen, etc.) DNA polymerases as part of the process of making the one or more double-stranded nucleic acid molecules. Such DNA polymerases are preferably thermostable DNA polymerases and most preferably the nucleic acid synthesis accomplished with such DNA polymerases is conducted at elevated temperatures, i.e., greater than 37° C. The invention also concerns compositions useful for making such double-stranded nucleic acid molecules. Such compositions comprise one or more (e.g., one, two, three, four, five, ten, twelve, fifteen, twenty, etc.) reverse transcriptases of the invention and optionally one or more DNA polymerases, a suitable buffer, one or more (e.g., one, two, three, four, five, ten, twelve, fifteen, etc.) primers, and/or one or more (e.g., one, two, three, four, five, etc.) nucleotides.

The invention also relates to methods for amplifying a nucleic acid molecule. Such amplification methods comprise mixing the double-stranded nucleic acid molecule or molecules produced as described above with one or more (e.g., one, two, three, four, five, ten, twelve, fifteen, etc.) DNA polymerases (preferably thermostable DNA polymerases) and incubating the mixture under conditions sufficient to amplify the double-stranded nucleic acid molecule. In a first embodiment, the invention concerns a method for amplifying a nucleic acid molecule, the method comprising (a) mixing one or more (e.g., one, two, three, four, five, ten, twelve, fifteen, twenty, etc.) nucleic acid templates (preferably one or more RNA or mRNA templates and more preferably a population of mRNA templates) with one or more reverse transcriptases of the invention and with one or more DNA polymerases and (b) incubating the mixture under conditions sufficient to amplify nucleic acid molecules complementary to all or a portion of the one or more templates. In some embodiments, the incubation of step (b) is performed at an elevated temperature. In specific embodiments, the elevated temperature may be from about 40° C. or greater, 45° C. or greater, 50° C. or greater, 51° C. or greater, about 52° C. or greater, about 53° C. or greater, about 54° C. or greater, about 55° C. or greater, about 56° C. or greater, about 57° C. or greater, about 58° C. or greater, about 59° C. or greater, about 60° C. or greater, about 61° C. or greater, about 62° C. or greater, about 63° C. or greater, about 64° C. or greater, about 65° C. or greater, about 66° C. or greater, about 67° C. or greater, about 68° C. or greater, about 69° C. or greater, about 70° C. or greater, about 71° C. or greater, about 72° C. or greater, about 73° C. or greater, about 74° C. or greater, about 75° C. or greater, about 76° C. or greater, about 77° C. or greater, or about 78° C. or greater; or at a temperature range of from about 37° C. to about 75° C., from about 40° C. to about 75° C., from about 45° C. to about 75° C., from about 50° C. to about 75° C., from about 51° C. to about 75° C., from about 52° C. to about 75° C., from about 53° C. to about 75° C., from about 54° C. to about 75° C., from about 55° C. to about 75° C. In some embodiments, the elevated temperature is within the range of about 50° C. to about 70° C., from about 51° C. to about 70° C., from about 52° C., to about 70° C., from about 53° C. to about 70° C., from about 54° C. to about 70° C., from about 55° C. to about 70° C., from about 55° C. to about 65° C., from about 56° C. to about 65° C., from about 56° C. to about 64° C. or about 56° C. to about 62° C. In other embodiments, the elevated temperature may be within the range of about 45° C. to about 60° C., from about 46° C. to about 60° C., from about 47° C. to about 60° C., from about 48° C. to about 60° C., from about 49° C. to about 60° C., from about 50° C. to about 60° C., from about 51° C. to about 60° C., from about 52° C. to about 60° C., from about 53° C. to about 60° C., or from about 54° C. to about 60° C. Preferably, the reverse transcriptases (1) are reduced or substantially reduced in RNase H activity, (2) are reduced or substantially reduced in TdT activity, and/or (3) exhibit increased fidelity. Preferably, the DNA polymerases comprise a first DNA polymerase having 3' exonuclease activity and a second DNA polymerase having substantially reduced 3' exonuclease activity.

The invention also concerns compositions comprising one or more reverse transcriptases of the invention and one or more DNA polymerases for use in amplification reactions. Such compositions may further comprise one or more nucleotides and/or a buffer suitable for amplification. The compositions of the invention may also comprise one or more oligonucleotide primers.

The invention is also directed to nucleic acid molecules (particularly single- or double-stranded cDNA molecules) or amplified nucleic acid molecules produced according to the above-described methods and to vectors (particularly expression vectors) comprising these nucleic acid molecules or amplified nucleic acid molecules.

The invention is further directed to recombinant host cells comprising the above-described nucleic acid molecules, amplified nucleic acid molecules or vectors.

Examples of such host cells include bacterial cells, yeast cells, plant cells and animal cells (including insect cells and mammalian cells).

The invention is additionally directed to methods of producing polypeptides encoded by the nucleic acid molecules produced by the methods of the invention. Such methods comprise culturing the above-described recombinant host cells and isolating the encoded polypeptides, and to polypeptides produced by such methods.

The invention also concerns methods for sequencing one or more (e.g., one, two, three, four, five, ten, twelve, fifteen, etc.) nucleic acid molecules using the compositions or enzymes of the invention. Such methods comprise (a) mixing one or more nucleic acid molecules (e.g., one or more RNA or DNA molecules) to be sequenced with one or more primers, one or more reverse transcriptases of the invention, one or more nucleotides and one or more terminating agents, such as one or more dideoxynucleoside triphosphates; (b) incubating the mixture under conditions sufficient to synthesize a population of nucleic acid molecules complementary to all or a portion of the one or more (e.g., one, two, three, four, ten, twelve, fifteen, twenty, thirty, fifty, one hundred, two hundred, etc.) nucleic acid molecules to be sequenced; and (c) separating the population of nucleic acid molecules to determine the nucleotide sequence of all or a portion of the one or more nucleic acid molecules to be sequenced. Such methods may also comprise (a) mixing a nucleic acid molecule (e.g., one or more RNA or DNA molecules) to be sequenced with one or more primers, one or more reverse transcriptases of the invention, one or more nucleotides and one or more terminating agents, such as one or more dideoxynucleoside triphosphates; (b) incubating the mixture under conditions sufficient to synthesize a population of nucleic acid molecules complementary to all or a portion of the nucleic acid molecule to be sequenced; and (c) separating members of the population of nucleic acid molecules to determine the nucleotide sequence of all or a portion of the nucleic acid molecule to be sequenced. In some embodiments, such incubation may be performed at elevated temperatures as described herein.

The invention is also directed to kits for use in methods of the invention. Such kits can be used for making, sequencing or amplifying nucleic acid molecules (single- or double-stranded), preferably at the elevated temperatures described herein. The kits of the invention comprise a carrier, such as a box or carton, having in close confinement therein one or more (e.g., one, two, three, four, five, ten, twelve, fifteen, etc.) containers, such as vials, tubes, bottles and the like. In the kits of the invention, a first container contains one or more of the reverse transcriptase enzymes of the present invention. The kits of the invention may also comprise, in the same or different containers, one or more DNA polymerases (preferably thermostable DNA polymerases), one or more (e.g., one, two, three, four, five, ten, twelve, fifteen, etc.) suitable buffers for nucleic acid synthesis, one or more nucleotides and one or more (e.g., one, two, three, four, five, ten, twelve, fifteen, etc.) oligonucleotide primers.

Alternatively, the components of the kit may be divided into separate containers (e.g., one container for each enzyme and/or component). The kits of the invention also may comprise instructions or protocols for carrying out the methods of the invention. In preferred kits of the invention, the reverse transcriptases are reduced or substantially reduced in RNase H activity, and are most preferably selected from the group consisting of M-MLV RNase H– reverse transcriptase, RSV RNase H– reverse transcriptase, AMV RNase H– reverse transcriptase, RAV RNase H– reverse transcriptase, MAV RNase H– reverse transcriptase and HIV RNase H– reverse transcriptase. In other preferred kits of the invention, the reverse transcriptases are reduced or substantially reduced in TdT activity, and/or exhibit increased fidelity, as described elsewhere herein.

In additional preferred kits of the invention, the enzymes (reverse transcriptases and/or DNA polymerases) in the containers are present at working concentrations.

Thus, the invention is further directed to kits for use in reverse transcription, amplification or sequencing of a nucleic acid molecule, the kit comprising one or more thermostable reverse transcriptases.

In specific embodiments, reverse transcriptases of kits of the invention may have one or more modifications or mutations at positions corresponding to amino acids selected from the group consisting of:

(a) leucine 52 of M-MLV reverse transcriptase;

(b) tyrosine 64 of M-MLV reverse transcriptase;

(c) lysine 152 of M-MLV reverse transcriptase;

(d) arginine 204 of M-MLV reverse transcriptase;

(e) methionine 289 of M-MLV reverse transcriptase; and (f) threonine 306 of M-MLV reverse transcriptase.

Reverse transcriptases of the invention include any reverse transcriptase having enhanced thermostability. Such reverse transcriptases include retroviral reverse transcriptases, bacterial reverse transcriptases, retrotransposon reverse transcriptases (e.g., reverse transcriptases of the Ty1 and/or Ty3 retrotransposons), and DNA polymerases having reverse transcriptase activity. Preferred reverse transcriptases of the invention include a single and multi-subunit reverse transcriptase and preferably retroviral reverse transcriptases. In particular, the invention relates to M-MLV-reverse transcriptases and ASLV-reverse transcriptases (such as AMV-RT and RSV-RT). Such reverse transcriptases of the invention preferably have reduced or substantially reduced RNase H activity.

Other embodiments of the present invention will be apparent to one of ordinary skill in light of the following drawings and description of the invention, and of the claims.

BRIEF DESCRIPTION OF THE DRAWINGS/FIGURES

Figure 3:

FIG. 3 represents a scanned phosphoimage of an extension assay using (1) SuperScript™II reverse transcriptase, and (2) F309N. The [$^{32}$P]-labeled 18-mer primer annealed to a 47-mer DNA template (5 nM) was extended by equal units of reverse transcriptase at 37° C. for 30 minutes as seen in the extension reactions with all 4 nucleotides. The extension reactions were analyzed by denaturing 6% gel electrophoresis. P, non-extended primer.

Figure 4:
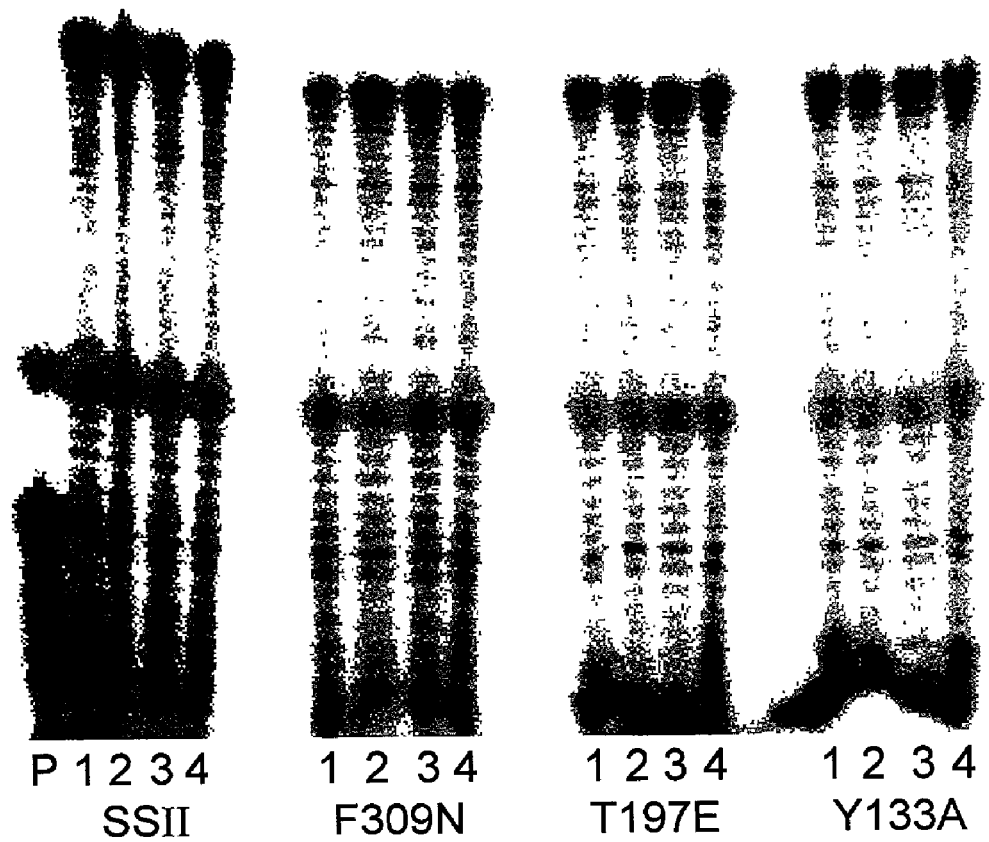

FIG. 4 represents a scanned phosphoimage showing a TdT extension assay of SuperScript™II reverse transcriptase and the mutants F309N, T197E, and Y133A. The [32P]-labeled 18-mer primer annealed to a 47-mer DNA template (5 nM) was extended with decreasing units of reverse transcriptase (lane (1) 646 units, lane (2) 200 units, lane (3) 50 units, and lane (4) 20 units) at 37° C. for 30 minutes with all four nucleotides (see the Methods section below in Example 3). The extension reactions were analyzed by denaturing 6% gel electrophoresis. In this assay, extension past the 47 nucleotide templates is considered non-template directed addition or TdT activity. P, non-extended primer.

Figure 5:
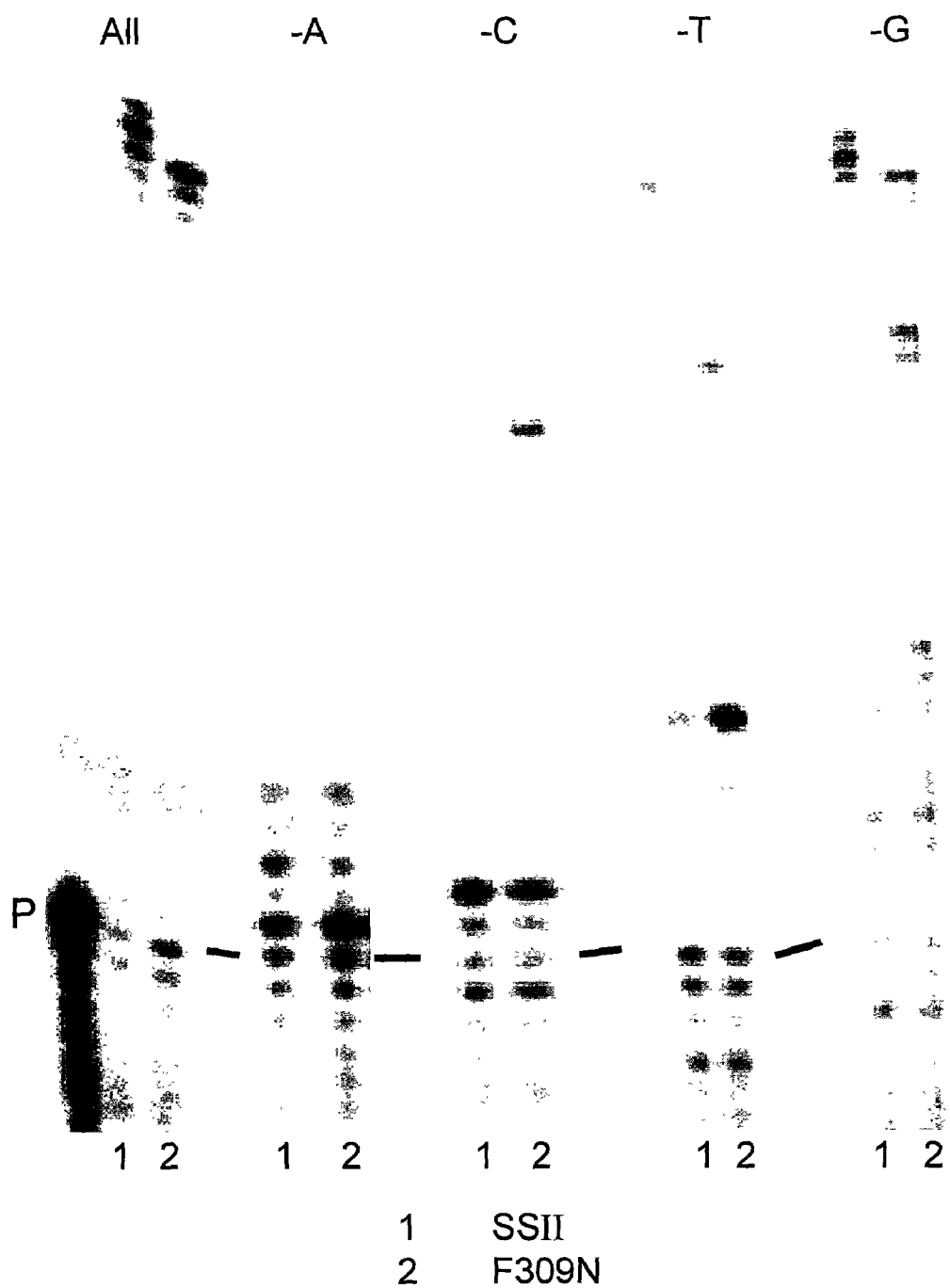

FIG. 5 represents a scanned phosphoimage showing misinsertion assays of SuperScript™II reverse transcriptase (1) and mutant protein F309N reverse transcriptase (2) with DNA template. The [$^{32}$P]-labeled 18-mer primer annealed to a 47-mer DNA template (5 nM) was extended by equal units of reverse transcriptase protein at 37° C. for 30 min. as seen in the extension reactions with all four nucleotides. The extension reactions were also performed in the presence of only 3 complementary dNTPs; minus dCTP, minus dATP, minus TTP, and minus dGTP. The extension reactions were analyzed by denaturing 6% gel electrophoresis. In this assay, the higher efficiency of elongation of terminated primer with only three nucleotides will reflect the lower fidelity of the SuperScript™II reverse transcriptase assayed. P, non-extended primer.

Figure 6:
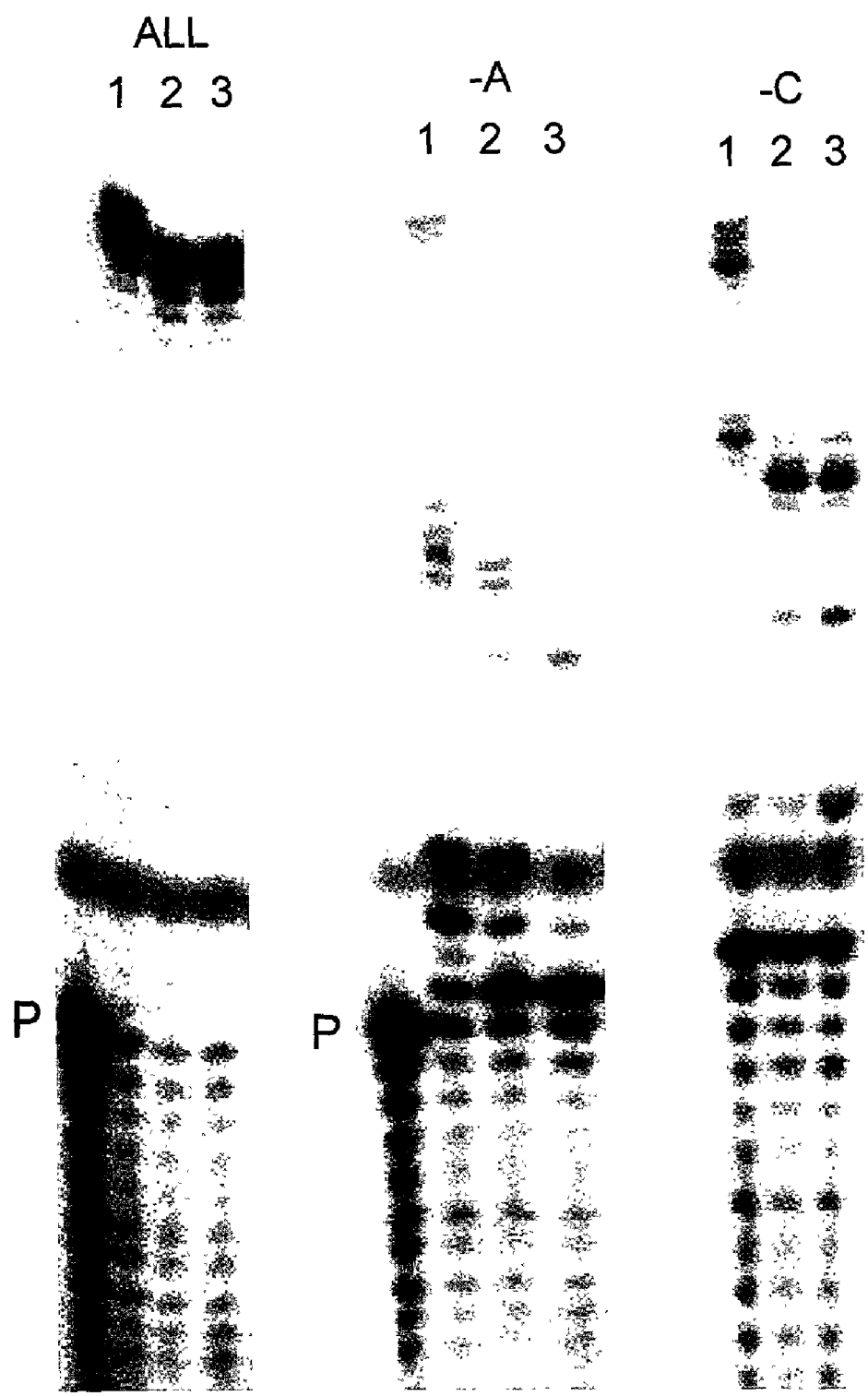

FIG. 6 represents a scanned phosphoimage showing a misinsertion assay of SuperScript™II reverse transcriptase (1) and mutant protein T197A/F309N reverse transcriptase (2) and V223H/F309N (3) with DNA template. The [32p]-labeled 18-mer primer annealed to a 47-mer DNA template (5 nM) was extended by equal units of reverse transcriptase protein at 37° C. for 30 min. as seen in the extension reactions with all four nucleotides. The extension reactions were also performed in the presence of only 3 complementary dNTPs; minus dATP, and minus dCTP. The extension reactions were analyzed by denaturing 6% gel electrophoresis. In this assay, the higher efficiency of elongation of terminated primer with only three nucleotides will reflect the lower fidelity of the SuperScript™II reverse transcriptase assayed. P, non-extended primer.

FIGS. 7A–7C. This figure depicts the DNA sequence (SEQ ID NO: 7), which encodes a wild type M-MLV reverse transcriptase having DNA polymerase activity and substantially no RNase H activity. Also shown is the corresponding amino acid sequence (SEQ ID NO: 8). Position 0 of FIG 7A is the codon ATG, which encodes a methionine residue. The methionine residue is the initiation codon for the recombinant DNA sequence. Thus, position 0 of this sequence does not represent an amino acid residue present in the wild type M-MLV reverse transcriptase having DNA polymerase activity and substantially no RNase H activity.

DETAILED DESCRIPTION OF THE INVENTION

In the description that follows, a number of terms used in recombinant DNA, virology and immunology are utilized. In order to provide a clearer and consistent understanding of the specification and claims, including the scope to be given such terms, the following definitions are provided.

Cloning vector. As used herein "cloning vector" means a nucleic acid molecule such as plasmid, cosmid, phage, phagemid or other nucleic acid molecule which is able to replicate autonomously in a host cell, and which is characterized by one or a small number of restriction endonuclease recognition sites at which such nucleic acid sequences may be cut in a determinable fashion, and into which DNA may be inserted in order to bring about its replication and cloning. The cloning vector may further contain a marker suitable for use in the identification of cells transformed with the cloning vector. Markers, for example, are genes that confer a recognizable phenotype on host cells in which such markers are expressed. Commonly used markers include, but are not limited to, antibiotic resistance genes such as tetracycline resistance or ampicillin resistance.

Expression vector. As used herein "expression vector" means a nucleic acid molecule similar to a cloning vector but which may additionally comprise nucleic acid sequences capable of enhancing and/or controlling the expression of a gene or other nucleic acid molecule which has been cloned into it, after transformation into a host. The additional nucleic acid sequences may comprise promoter sequences, repressor binding sequences and the like. The cloned gene or nucleic acid molecule is usually operably linked to one or more (e.g., one, two, three, four, etc.) of such control sequences such as promoter sequences.

Recombinant host. As used herein "recombinant" means any prokaryotic or eukaryotic or microorganism which contains the desired cloned genes or nucleic acid molecules, for example, in an expression vector, cloning vector or any nucleic acid molecule. The term "recombinant host" is also meant to include those host cells which have been genetically engineered to contain the desired gene or other nucleic acid molecule on the host chromosome or genome.

Host. As used herein "host" means any prokaryotic or eukaryotic organism that is the recipient of a replicable expression vector, cloning vector or any nucleic acid molecule. The nucleic acid molecule may contain, but is not limited to, a structural gene, a promoter and/or an origin of replication.

Promoter. As used herein "promoter" means a nucleic acid sequence generally described as the 5' region of a gene, located proximal to the start codon which is capable of directing the transcription of a gene or other nucleic acid molecule. At the promoter region, transcription of an adjacent gene(s) or nucleic acid(s) is initiated.

Gene. As used herein "gene" means a nucleic acid sequence that contains information necessary for expression of a polypeptide or protein. It includes the promoter and the structural gene as well as other sequences involved in expression of the protein.

Structural gene. As used herein "structural gene" means a DNA or other nucleic acid sequence that is transcribed into messenger RNA that is then translated into a sequence of amino acids characteristic of a specific polypeptide.

Operably linked. As used herein "operably linked" means that a nucleic acid element is positioned so as to influence the initiation of expression of the polypeptide encoded by the structural gene or other nucleic acid molecule.

Expression. As used herein "expression" refers to the process by which a gene or other nucleic acid molecule produces a polypeptide. It includes transcription of the gene or nucleic acid molecule into messenger RNA (mRNA) and the translation of such mRNA into polypeptide(s).

Substantially pure. As used herein "substantially pure" means that the desired material is essentially free from contaminating cellular components which are associated with the desired material in nature. Contaminating cellular components may include, but are not limited to, enzymatic activities such as phosphatases, exonucleases, endonucleases or undesirable DNA polymerase enzymes. Preferably, reverse transcriptases of the invention are substantially pure.

Primer. As used herein "primer" refers to a single-stranded oligonucleotide that is extended by covalent bonding of nucleotide monomers during amplification or polymerization of a DNA molecule.

Template. The term "template" as used herein refers to a double-stranded or single-stranded nucleic acid molecule which is to be amplified, copied or sequenced. In the case of a double-stranded DNA molecule, denaturation of its strands to form single-stranded first and second strands may be performed before these molecules are amplified, copied or sequenced. A primer complementary to a portion of a nucleic acid template is hybridized under appropriate conditions and a nucleic acid polymerase, such as the reverse transcriptase enzymes of the invention, may then add nucleotide monomers to the primer thereby synthesizing a nucleic acid molecule complementary to said template or a portion thereof. The newly synthesized nucleic acid molecule, according to the invention, may be equal or shorter in length than the original template. Mismatch incorporation during the synthesis or extension of the newly synthesized nucleic acid molecule may result in one or a number of mismatched base pairs. Thus, the synthesized nucleic acid molecule need not be exactly complementary to the template.

Incorporating. The term "incorporating" as used herein means becoming a part of a nucleic acid molecule or primer.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA) and deoxyribonucleotides are incorporated into DNA by DNA polymerases. The term nucleotide includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrative examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Hybridization. As used herein, hybridization (hybridizing) refers to the pairing of two complementary single-stranded nucleic acid molecules (RNA and/or DNA) to give a double-stranded molecule. As one skilled in the art will recognize, two nucleic acid molecules may be hybridized, although the base pairing is not completely complementary. Accordingly, mismatched bases do not prevent hybridization of two nucleic acid molecules provided that appropriate conditions, well known in the art, are used.

Thermostable Reverse Transcriptase. For the purposes of this disclosure, a thermostable reverse transcriptase is defined as a reverse transcriptase which retains a greater percentage of its activity after a heat treatment than is retained by a reverse transcriptase that has wild-type thermostability after an identical treatment. Thus, a reverse transcriptase having increased/enhanced thermostability is defined as a polymerase having any increase in thermostability, preferably from about 1.2 to about 10,000 fold, from about 1.5 to about 10,000 fold, from about 2 to about 5,000 fold, or from about 2 to about 2000 fold (preferably greater than about 5 fold, more preferably greater than about 10 fold, still more preferably greater than about 50 fold, still more preferably greater than about 100 fold, still more preferably greater than about 500 fold, and most preferably greater than about 1000 fold) retention of activity after a heat treatment sufficient to cause a reduction in the activity of a reverse transcriptase that is wild-type for thermostability. Preferably, the mutant or modified reverse transcriptase of the invention is compared to the corresponding unmodified or wild-type reverse transcriptase to determine the relative enhancement or increase in thermostability. For example, after a heat treatment at 52° C. for 5 minutes, a thermostable reverse transcriptase may retain approximately 90% of the activity present before the heat treatment, whereas a reverse transcriptase that is wild-type for thermostability may retain 10% of its original activity. Likewise, after a heat treatment at 53° C. for five minutes, a thermostable reverse transcriptase may retain approximately 80% of its original activity, whereas a reverse transcriptase that is wild-type for thermostability may have no measurable activity. Similarly, after a heat treatment at 50° C. for five minutes, a thermostable reverse transcriptase may retain approximately 50%, approximately 55%, approximately 60%, approximately 65%, approximately 70%, approximately 75%, approximately 80%, approximately 85%, approximately 90%, or approximately 95% of its original activity, whereas a reverse transcriptase that is wild-type for thermostability may have no measurable activity or may retain 10%, 15% or 20% of its original activity. In the first instance (i.e., after heat treatment at 52° C. for 5 minutes), the thermostable reverse transcriptase would be said to be 9-fold more thermostable than the wild-type reverse transcriptase. Examples of conditions which may be used to measure thermostability of reverse transcriptases are set out below in Example 2.

The thermostability of a reverse transcriptase can be determined by comparing the residual activity of a sample of the reverse transcriptase that has been subjected to a heat treatment, i.e., incubated at 52° C. for a given period of time, for example, five minutes, to a control sample of the same reverse transcriptase that has been incubated at room temperature for the same length of time as the heat treatment. Typically the residual activity may be measured by following the incorporation of a radiolabed deoxyribonucleotide into an oligodeoxyribonucleotide primer using a complementary oligoribonucleotide template. For example, the ability of the reverse transcriptase to incorporate [$\alpha$-$^{32}$P]-dGTP into an oligo-dG primer using a poly(riboc) template may be assayed to determine the residual activity of the reverse transcriptase.

In another aspect, thermostable reverse transcriptases of the invention are defined as any reverse transcriptase which is inactivated at a higher temperature compared to the corresponding wild-type, unmutated, or unmodified reverse transcriptase. Preferably, the inactivation temperature for the thermostable reverse transcriptases of the invention is from about 2° C. to about 50° C. (e.g., about 2° C., about 4° C., about 5° C., about 8° C., about 10° C., about 12° C., about 14° C., about 16° C., about 18° C., about 20° C., about 24° C., about 26° C., about 28° C., about 30° C., about 33° C., about 35° C., about 38° C., about 40° C., about 42° C., about 44° C., about 46° C., about 48° C., or about 50° C.) higher than the inactivation temperature for the corresponding wild-type, unmutated, or unmodified reverse transcriptase. More preferably, the inactivation temperature for the reverse transcriptases of the invention is from about 5° C. to about 50° C., from about 5° C. to about 40° C., from about 5° C. to about 30° C., or from about 5° C. to about 25° C. greater than the inactivation temperature for the corresponding wild-type, unmutated or unmodified reverse transcriptase, when compared under the same conditions.

The difference in inactivation temperature for the reverse transcriptase of the invention compared to its corresponding wild-type, unmutated or unmodified reverse transcriptase can be determined by treating samples of such reverse transcriptases at different temperatures for a defined time period and then measuring residual reverse transcriptase activity, if any, after the samples have been heat treated. Determination of the difference or delta in the inactivation temperature between the test reverse transcriptase compared to the wild-type, unmutated or unmodified control is determined by comparing the difference in temperature at which each reverse transcriptase is inactivated (i.e., no residual reverse transcriptase activity is measurable in the particular assay used). As will be recognized, any number of reverse transcriptase assays may be used to determine the different or delta of inactivation temperatures for any reverse transcriptases tested.

Terminal extension activity. As used herein, terminal extension activity refers to the ability of a reverse transcriptase (RT) to add additional bases on to the 3' end of a newly synthesized cDNA strand beyond the 5' end of the DNA or mRNA template. Terminal extension activity may add bases specifically (with a nucleotide bias) or randomly.

Terminal extension activity is also known as terminal deoxynucleotidyl transferase (TdT) activity. A reverse transcriptase having reduced, substantially reduced, or eliminated TdT activity is defined as any reverse transcriptase having lower TdT activity than the specific activity of the corresponding wild-type, unmutated, or unmodified enzyme, particularly, less than about 90% of the specific activity of the corresponding wild-type, unmutated, or unmodified enzyme, less than about 85% of the specific activity of the corresponding wild-type, unmutated, or unmodified enzyme, less than about 80% of the specific activity of the corresponding wild-type, unmutated, or unmodified enzyme, less than about 75% of the specific activity of the corresponding wild-type, unmutated, or unmodified enzyme, less than about 50% of the specific activity of the corresponding wild-type, unmutated, or unmodified enzyme, less than about 25% of the specific activity of the corresponding wild-type, unmutated, or unmodified enzyme, less than about 15% of the specific activity of the corresponding wild-type, unmutated, or unmodified enzyme, less than 10% of the specific activity of the corresponding wild-type, unmutated, or unmodified enzyme, less than about 5% of the specific activity of the corresponding wild-type, unmutated, or unmodified enzyme, or less than about 1% of the specific activity of the corresponding wild-type, unmutated, or unmodified enzyme. Eliminated TdT activity is defined as a level of activity that is undetectable by the assay methods set out herein in Example 3.

As noted below in Example 3, reverse transcriptases are known in the art which extend nucleic acid molecules 2–3 nucleotides past the end of templates (e.g., RNA or DNA templates). Further, in any one reaction mixture in which reverse transcription occurs, mixtures of molecules may be present which contain different numbers of nucleotides that extend beyond the end of the template. TdT activity is determined herein in reference to the number or percentage of molecules which contain one or more nucleotides which extend beyond the end of the template. For example, if a wild-type reverse transcriptase adds 1 or more nucleotides past the end of a template to 90% of the molecules generated during reverse transcription and a modified reverse transcriptase adds 1 or more nucleotides past the end of a template to 45% of the molecules under the same or similar conditions, then the modified reverse transcriptase would be said to exhibit a 50% decrease in TdT activity as compared to the wild-type enzyme. Further, an F309N, T306K, H204R mutant of M-MLV SuperScript™II has been generated which exhibits about 0% of the TdT activity exhibited by SuperScript™II when DNA is used as a template and about 10–20% of the TdT activity exhibited by SuperScript™II when RNA is used as a template.

Fidelity. Fidelity refers to the accuracy of polymerization, or the ability of the reverse transcriptase to discriminate correct from incorrect substrates, (e.g., nucleotides) when synthesizing nucleic acid molecules which are complementary to a template. The higher the fidelity of a reverse transcriptase, the less the reverse transcriptase misincorporates nucleotides in the growing strand during nucleic acid synthesis; that is, an increase or enhancement in fidelity results in a more faithful reverse transcriptase having decreased error rate or decreased misincorporation rate.

A reverse transcriptase having increased/enhanced/higher fidelity is defined as a polymerase having any increase in fidelity, preferably about 1.2 to about 10,000 fold, about 1.5 to about 10,000 fold, about 2 to about 5,000 fold, or about 2 to about 2000 fold (preferably greater than about 5 fold, more preferably greater than about 10 fold, still more preferably greater than about 50 fold, still more preferably greater than about 100 fold, still more preferably greater than about 500 fold and most preferably greater than about 100 fold) reduction in the number of misincorporated nucleotides during synthesis of any given nucleic acid molecule of a given length compared to the control reverse transcriptase. Preferably, the mutant or modified reverse transcriptase of the invention is compared to the corresponding unmodified or wild-type reverse transcriptase to determine the relative enhancement or increase in fidelity. For example, a mutated reverse transcriptase may misincorporate one nucleotide in the synthesis of a nucleic acid molecule segment of 1000 bases compared to an unmutated reverse transcriptase misincorporating 10 nucleotides in the same size segment. Such a mutant reverse transcriptase would be said to have an increase of fidelity of 10 fold.

Fidelity can also be measured by the decrease in the incidence of frame shifting, as described below in Example 5. A reverse transcriptase having increased fidelity is defined as a polymerase or reverse transcriptase having any increase in fidelity with respect to frame shifting, as compared to a control reverse transcriptase (e.g., a wild-type reverse transcriptase), for example, a reverse transcriptase having greater than about 1.2 fold increased fidelity with respect to frame shifting, having greater than about 1.5 fold increased fidelity with respect to frame shifting, having greater than about 5 fold increased fidelity with respect to frame shifting, having greater than about 10 fold increased fidelity with respect to frame shifting, having greater than about 20 fold increased fidelity with respect to frame shifting, having greater than about 30 fold increased fidelity with respect to frame shifting, or having greater than about 40 fold increased fidelity with respect to frame shifting.

A reverse transcriptase having increased/enhanced/higher fidelity, with respect to frame shifting, can also be defined as a reverse transcriptase or polymerase having any increase in fidelity, such as from about 1.5 to about 10,000 fold, from about 2 to about 5,000 fold, from about 2 to about 2000 fold, from about 1.5 to about 40 fold, from about 5 to about 40 fold, from about 10 to about 40 fold, from about 20 to about 40 fold, from about 30 to about 40 fold, from about 5 to about 30 fold, from about 10 to about 30 fold, from about 15 to about 30 fold, from about 20 to about 30 fold, from about 5 to about 20 fold, from about 10 to about 20 fold, from about 15 to about 20 fold, from about 10 to about 100 fold, from about 15 to about 100 fold, from about 20 to about 100 fold, from about 30 to about 100 fold, or from about 50 to about 100 fold increased fidelity with respect to frame shifting.

A reverse transcriptase having reduced misincorporation is defined herein as either a mutated or modified reverse transcriptase that has about or less than 90%, has about or less than 85%, has about or less than 75%, has about or less than 70%, has about or less than 60%, or preferably has about or less than 50%, preferably has about or less than 25%, more preferably has about or less than 10%, and most preferably has about or less than 1% of relative misincorporation compared to the corresponding wild-type, unmutated, or unmodified enzyme.

The fidelity or misincorporation rate of a reverse transcriptase can be determined by sequencing or by other methods known in the art (Eckert & Kunkel, 1990, *Nucl. Acids Res.* 18:3739–3744). In one example, the sequence of a DNA molecule synthesized by the unmutated and mutated reverse transcriptases can be compared to the expected (known) sequence. In this way, the number of errors (misincorporation or frame shifts) can be determined for each enzyme and compared. In another example, the unmutated and mutated reverse transcriptases may be used to sequence a DNA molecule having a known sequence. The number of sequencing errors (misincorporation or frame shifts) can be compared to determine the fidelity or misincorporation rate of the enzymes. Other means of determining the fidelity or misincorporation rate include a forward complementation assay using an RNA template as described below and previously in Boyer J. C. et al. *Methods Enzymol.* 275:523 (1996), and are set out in the examples. Other methods of determining the fidelity or misincorporation rate will be recognized by one of skill in the art.

Strand jumping. Strand jumping, as used herein, refers to a type of random mutation caused by an reverse transcriptase "skipping" more than one (e.g., two, five, ten, fifty, one-hundred, etc.) nucleotides on the mRNA template, resulting in a deletion of the corresponding nucleotides in the resulting cDNA.

Hand domain. The hand domain, as used herein, refers to those amino acids which are in the area or areas that control the template, primer, or nucleotide interaction of the reverse transcriptase. This domain is further characterized by a group of three regions of secondary structure in a reverse transcriptase enzyme, the thumb, fingers and palm regions. The thumb region is defined as residing between amino acids 240–315 of HIV reverse transcriptase, or between amino acids 280–355 of M-MLV reverse transcriptase. The fingers region is defined as residing between amino acids 1–85 and 120–154 of HIV reverse transcriptase, or between 1–124 and 161–193 of M-MLV reverse transcriptase. The palm region is defined as residing between amino acids 86–199 and 155–239 of HIV reverse transcriptase, or between amino acids 126–160 and 193–279 of M-MLV reverse transcriptase. These areas are generally defined, and the amino acids defining the N-termini and C-termini are approximate. Corresponding regions may also be defined for other reverse transcriptases. Preferred reverse transcriptases of the invention have one or more modifications or mutations within the hand domain. More particularly, reverse transcriptases of the invention comprise one or more mutations or modifications within one or more regions, including the thumb, finger, and palm regions.

In general, the invention provides compositions for use in reverse transcription of a nucleic acid molecule comprising a reverse transcriptase with one or more (e.g., one, two, three, four, five, ten, twelve, fifteen, twenty, thirty, etc.) mutations or modification which render the reverse transcriptase more thermostable. The invention also provides compositions for use in reverse transcription of a nucleic acid molecule comprising a reverse transcriptase with one or more mutations or modification which render the reverse transcriptase more efficient, that is having higher fidelity, and/or has lower TdT activity. The invention further provides compositions comprising a reverse transcriptase with one or more mutations or modification which render the reverse transcriptase more thermostable and more efficient.

The enzymes in these compositions are preferably present in working concentrations and are also preferably reduced or substantially reduced in RNase H activity. Alternatively, the reverse transcriptases used in the compositions of the invention may have RNase H activity. Preferred reverse transcriptases include retroviral reverse transcriptases such as M-MLV reverse transcriptase, HIV reverse transcriptase, RSV reverse transcriptase, AMV reverse transcriptase, RAV reverse transcriptase, and MAV reverse transcriptase or other ASLV reverse transcriptases or their corresponding RNase H– derivatives. Additional reverse transcriptases which may be used to prepare compositions of the invention include bacterial reverse transcriptases (e.g., *Escherichia coli* reverse transcriptase) (see, e.g., Mao et al., *Biochem. Biophys. Res. Commun.* 227:489–93 (1996)) and reverse transcriptases of *Saccharomyces cerevisiae* (e.g., reverse transcriptases of the Ty1 or Ty3 retrotransposons) (see, e.g., Cristofari et al., *Jour. Biol. Chem.* 274:36643–36648 (1999); Mules et al., *Jour. Virol.* 72:6490–6503 (1998)).

In accordance with the invention, any number of mutations can be made to the reverse transcriptases and, in a preferred aspect, multiple mutations can be made to result in an increased thermostability. Such mutations include point mutations, frame shift mutations, deletions and insertions, with one or more (e.g., one, two, three, four, five, ten, twelve, fifteen, twenty, thirty, etc.) point mutations preferred. Mutations may be introduced into the reverse transcriptases of the present invention using any methodology known to those of skill in the art. Mutations may be introduced randomly by, for example, conducting a PCR reaction in the presence of manganese as a divalent metal ion cofactor. Alternatively, oligonucleotide directed mutagenesis may be used to create the mutant polymerases which allows for all possible classes of base pair changes at any determined site along the encoding DNA molecule. In general, this technique involves annealing an oligonucleotide complementary (except for one or more mismatches) to a single stranded nucleotide sequence coding for the reverse transcriptase of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

The invention is also directed to methods for reverse transcription of one or more (e.g., one, two, three, four, five, ten, twelve, fifteen, twenty, etc.) nucleic acid molecules comprising mixing one or more (e.g., one, two, three, four, five, ten, twelve, fifteen, twenty, etc.) nucleic acid templates, which is preferably RNA or messenger RNA (mRNA) and more preferably a population of mRNA molecules, with one or more reverse transcriptase of the present invention and incubating the mixture under conditions sufficient to make a nucleic acid molecule or molecules complementary to all or a portion of the one or more (e.g., one, two, three, four, five, ten, twelve, fifteen, twenty, thirty, etc.) templates. To make the nucleic acid molecule or molecules complementary to the one or more templates, a primer (e.g., an oligo(dT) primer) and one or more nucleotides are preferably used for nucleic acid synthesis in the 5' to 3' direction. Nucleic acid molecules suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g., human, cow, pig, mouse, sheep, horse, monkey, canine, feline, rat, rabbit, bird, fish, insect, etc.). Such nucleic acid molecules may also be isolated from viruses.

The invention further provides methods for amplifying or sequencing a nucleic acid molecule comprising contacting the nucleic acid molecule with a reverse transcriptase of the present invention. Preferred such methods comprise one or more polymerase chain reactions (PCRs).

Sources of Reverse Transcriptases

Enzymes for use in the compositions, methods and kits of the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., Science 239:487–491 (1988); U.S. Pat. Nos. 4,889,818 and 4,965,188), Tne DNA polymerase (PCT Publication No. WO 96/10640), Tma DNA polymerase (U.S. Pat. No. 5,374,553) and mutants, fragments, variants or derivatives thereof (see, e.g., commonly owned U.S. Pat. Nos. 5,948,614 and 6,015,668, which are incorporated by reference herein in their entireties). Preferably, reverse transcriptases for use in the invention include retroviral reverse transcriptases such as M-MLV reverse transcriptase, AMV reverse transcriptase, RSV reverse transcriptase, RAV reverse transcriptase, MAV reverse transcriptase, and generally ASLV reverse transcriptases. As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. For example, one or more point mutations (e.g., substitution of one or more amino acids with one or more different amino acids) may be used to construct mutant reverse transcriptases of the invention.

The invention further includes reverse transcriptases which are 70%, 75%, 80%, 85%, 90%, 95%, 96%, 97%, 98%, or 99% identical at the amino acid level to a wild-type reverse transcriptase (e.g., M-MLV reverse transcriptase, AMV reverse transcriptase, RSV reverse transcriptase, HIV reverse transcriptase, etc.) and exhibit increased thermostability. Also included within the invention are reverse transcriptases which are 70%, 75%, 80%, 85%, 90%, 95%, 96%, 97%, 98%, or 99% identical at the amino acid level to a reverse transcriptase comprising the amino acid sequence set out below in Table 3 (SEQ ID NO:2) and exhibit increased thermostability and/or more efficient (e.g., having higher fidelity and/or having lower TdT activity). The invention also includes nucleic acid molecules which encode the above described reverse transcriptases.

The invention also includes fragments of reverse transcriptases which comprise at least 200, 250, 300, 350, 400, 450, 500, 550, 600, 650, or 700 amino acid residues and retain one or more activities associated with reverse transcriptases. Such fragments may be obtained by deletion mutation, by recombinant techniques that are routine and well-known in the art, or by enzymatic digestion of the reverse transcriptase(s) of interest using any of a number of well-known proteolytic enzymes. The invention further includes nucleic acid molecules which encode the above described mutant reverse transcriptases and reverse transcriptase fragments.

Reverse transcriptase fragments of the invention also comprise amino acids 1–355, 1–498, 1–500, and 1–550 of M-MLV reverse transcriptase, as well as corresponding fragments of other reverse transcriptases. Reverse transcriptase fragments of the invention further comprise polypeptides which are 70%, 75%, 80%, 85%, 90%, 95%, 96%, 97%, 98%, or 99% identical to one or more of the fragments set out above.

By a protein or protein fragment having an amino acid sequence at least, for example, 70% "identical" to a reference amino acid sequence it is intended that the amino acid sequence of the protein is identical to the reference sequence except that the protein sequence may include up to 30 amino acid alterations per each 100 amino acids of the amino acid sequence of the reference protein. In other words, to obtain a protein having an amino acid sequence at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino (N-) and/or carboxy (C-) terminal positions of the reference amino acid sequence and/or anywhere between those terminal positions, interspersed either individually among residues in the reference sequence and/or in one or more contiguous groups within the reference sequence. As a practical matter, whether a given amino acid sequence is, for example, at least 70% identical to the amino acid sequence of a reference protein can be determined conventionally using known computer programs such as those described above for nucleic acid sequence identity determinations, or using the CLUSTAL W program (Thompson, J. D., et al., *Nucleic Acids Res.* 22:4673–4680 (1994)).

Preferred enzymes for use in the invention include those that are reduced or substantially reduced in RNase H activity. Such enzymes that are reduced or substantially reduced in RNase H activity may be obtained by mutating, for example, the RNase H domain within the reverse transcriptase of interest, for example, by introducing one or more (e.g., one, two, three, four, five, ten, twelve, fifteen, twenty, thirty, etc.) point mutations, one or more (e.g., one, two, three, four, five, ten, twelve, fifteen, twenty, thirty, etc.) deletion mutations, and/or one or more (e.g., one, two, three, four, five, ten, twelve, fifteen, twenty, thirty, etc.) insertion mutations as described above.

By an enzyme "substantially reduced in RNase H activity" is meant that the enzyme has less than about 30%, less than about 25%, less than about 20%, more preferably less than about 15%, less than about 10%, less than about 7.5%, or less than about 5%, and most preferably less than about 5% or less than about 2%, of the RNase H activity of the corresponding wild-type or RNase H$^+$ enzyme, such as wild-type Moloney Murine Leukemia Virus (M-MLV), Avian Myeloblastosis Virus (AMV) or Rous Sarcoma Virus (RSV) reverse transcriptases.

Reverse transcriptases having reduced or substantially reduced RNase H activity have been previously described (see U.S. Pat. Nos. 5,668,005, 6,063,608, and PCT Publication No. WO 98/47912). The RNase H activity of any enzyme may be determined by a variety of assays, such as those described, for example, in U.S. Pat. No. 5,244,797, in Kotewicz, M. L., et al., *Nucl. Acids Res.* 16:265 (1988), in Gerard, G. F., et al., *FOCUS* 14(5):91 (1992), and in U.S. Pat. No. 5,668,005, the disclosures of all of which are fully incorporated herein by reference.

Particularly preferred enzymes for use in the invention include, but are not limited to, M-MLV RNase H– reverse transcriptase, RSV RNase H– reverse transcriptase, AMV RNase H– reverse transcriptase, RAV RNase H– reverse transcriptase, MAV RNase H– reverse transcriptase and HIV RNase H– reverse transcriptase. It will be understood by one of ordinary skill, however, that any enzyme capable of producing a DNA molecule from a ribonucleic acid molecule (i.e., having reverse transcriptase activity) that is reduced or substantially reduced in RNase H activity may be equivalently used in the compositions, methods and kits of the invention.

Enzymes for use in the invention also include those in which terminal deoxynucleotidyl transferase (TdT) activity has been reduced, substantially reduced, or eliminated. Such enzymes that are reduced or substantially reduced in terminal deoxynucleotidyl transferase activity, or in which TdT activity has been eliminated, may be obtained by mutating, for example, amino acid residues within the reverse transcriptase of interest which are in close proximity or in contact with the template-primer, for example, by introducing one or more (e.g., one, two, three, four, five, ten, twelve, fifteen, twenty, thirty, etc.) point mutations, one or more deletion mutations, and/or one or more insertion mutations. Reverse transcriptases which exhibit decreased TdT activity are described in U.S. application Ser. No. 09/808,124, filed Mar. 15, 2001 (the entire disclosure of which is incorporated herein by reference), and include reverse transcriptases with one or more alterations at amino acid positions equivalent or corresponding to Y64, M289, F309, T197 and/or Y133 of M-MLV reverse transcriptase.

In one aspect, amino acid substitutions are made at one or more of the above identified positions (i.e., amino acid positions equivalent or corresponding to Y64, M289, F309, T197 or Y133 of M-MLV reverse transcriptase). Thus, the amino acids at these positions may be substituted with any other amino acid including Ala, Asn, Asp, Cys, Gln, Glu, Gly, His, Ile, Leu, Lys, Met, Phe, Pro, Ser, Thr, Trp, Tyr, and Val. Specific example of reverse transcriptases which exhibit reduced or substantially reduced TdT activity include M-MLV reverse transcriptases (e.g., SuperScript™II) in which (1) the phenylalanine residue at position 309 has been replaced with asparagine, (2) the threonine residue at position 197 has been replaced with either alanine or glutamic acid, and/or (3) the tyrosine residue at position 133 has been replaced with alanine.

Enzymes for use in the invention also include those in which exhibit increased fidelity. Reverse transcriptases which exhibit increased fidelity are described in U.S. application Ser. No. 60/189,454, filed Mar. 15, 2000, and U.S. application Ser. No. 09/808,124, filed Mar. 15, 2001 (the entire disclosures of each of which are incorporated herein by reference), and include reverse transcriptases with one or more alterations at positions equivalent or corresponding to those set out below in Table 2.

TABLE 2

| RT | Amino Acid |
| --- | --- |
| M-MLV | Y64 (e.g., Y64W, Y64R), R116 (e.g., R116M), K152 (e.g., K152R), Q190 (e.g., Q190F), T197 (e.g., T197A, T197E), V223 (e.g., V223H, V223I, V223F), D124, H126, Y133 (e.g., Y133A, Y133H), F309 (e.g., F309N, F309R) |
| AMV | W25, R76, K110, Q149, T156, M182 |
| RSV | W25, R76, K110, Q149, T156, M182 |
| HIV | W24, R78, G112, Q151, A158, M184 |

In some embodiments of the invention, amino acid substitutions are made at one or more of the above identified positions. Thus, the amino acids at these positions may be substituted with any other amino acid including Ala, Asn, Asp, Cys, Gln, Glu, Gly, His, Ile, Leu, Lys, Met, Phe, Pro, Ser, Thr, Trp, Tyr, and Val. Specific example of reverse transcriptases which exhibit increased fidelity include M-MLV reverse transcriptase in which (1) the valine residue at position 223 has been replaced with histidine, phenylalanine or isoleucine, (2) the arginine residue at position 116 has been replaced with methionine, (3) the lysine residue at position 152 has been replaced with arginine, (4) the glutamic acid residue at position 190 has been replaced with phenylalanine, (5) the threonine residue at position 197 has been replaced with alanine or glutamic acid, (6) the phenylalanine residue at position 309 has been replaced with asparagine or arginine, (7) the tyrosine residue at position 133 has been replaced with histidine or alanine, and/or (8) the tyrosine residue at position 64 has been replaced with tryptophan or arginine.

Thus, in specific embodiments, the invention includes reverse transcriptases which exhibit increased thermostability and, optionally, also exhibit one or more of the following characteristics: (1) reduced or substantially reduced RNase H activity, (2) reduced or substantially reduced TdT activity, and/or (3) increased fidelity.

The invention also relates to reverse transcriptase mutants, where the mutations or substitutions have been made in a recognized region of the reverse transcriptase enzyme. Such regions include, but are not limited to, the fingers, palm and thumb regions. Thus, the invention includes reverse transcriptases which exhibit increased thermostability (as well as other properties), as described elsewhere herein, and have one or more (e.g., one, two, three, four, five, ten, fifteen, etc.) mutations or modification in the hand domain and, more specifically, in one or more regions including the fingers, palm and/or thumb regions.

Polypeptides having reverse transcriptase activity for use in the invention may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372–3376 (1988)).

In one aspect of the invention, mutant or modified reverse transcriptases are made by recombinant techniques. A number of cloned reverse transcriptase genes are available or may be obtained using standard recombinant techniques (see U.S. Pat. No. 5,668,005 and PCT Publication No. WO 98/47912).

To clone a gene or other nucleic acid molecule encoding a reverse transcriptase which will be modified in accordance with the invention, isolated DNA which contains the reverse transcriptase gene or open reading frame may be used to construct a recombinant DNA library. Any vector, well known in the art, can be used to clone the reverse transcriptase of interest. However, the vector used must be compatible with the host in which the recombinant vector will be transformed.

Prokaryotic vectors for constructing the plasmid library include plasmids such as those capable of replication in *E. coli* such as, for example, pBR322, ColE1, pSC101, pUC-vectors (pUC18, pUC19, etc.: In: *Molecular Cloning, A Laboratory Manual,* Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). Bacillus plasmids include pC194, pUB110, pE194, pC221, pC217, etc. Such plasmids are disclosed by Glyczan, T. In: *The Molecular Biology Bacilli, Academic Press, York (1982), 307–329.* Suitable Streptomyces plasmids include pIJ101 (Kendall et al., *J. Bacteriol.* 169:4177–4183 (1987)). *Pseudomonas* plasmids are reviewed by John et al., (*Rad. Insec. Dis.* 8:693–704 (1986)), and Igaki, (*Jpn. J. Bacteriol.* 33:729–742 (1978)). Broad-host range plasmids or cosmids, such as pCP13 (Darzins and Chakrabarty, *J. Bacteriol.* 159:9–18 (1984)) can also be used for the present invention. Preferred vectors for cloning the genes and nucleic acid molecules of the present invention are prokaryotic vectors. Preferably, pCP13 and pUC vectors are used to clone the genes of the present invention.

Suitable host for cloning the reverse transcriptase genes and nucleic acid molecules of interest are prokaryotic hosts. One example of a prokaryotic host is *E. coli.* However, the desired reverse transcriptase genes and nucleic acid molecules of the present invention may be cloned in other prokaryotic hosts including, but not limited to, hosts in the genera *Escherichia, Bacillus, Streptomyces, Pseudomonas, Salmonella, Serratia,* and *Proteus.* Bacterial hosts of particular interest include *E. coli* DH10B, which may be obtained from Invitrogen Corp. (Carlsbad, Calif.).

Eukaryotic hosts for cloning and expression of the reverse transcriptase of interest include yeast, fungal, and mammalian cells. Expression of the desired reverse transcriptase in such eukaryotic cells may require the use of eukaryotic regulatory regions which include eukaryotic promoters. Cloning and expressing the reverse transcriptase gene or nucleic acid molecule in eukaryotic cells may be accomplished by well known techniques using well known eukaryotic vector systems.

Once a DNA library has been constructed in a particular vector, an appropriate host is transformed by well known techniques. Transformed cells are plated at a density to produce approximately 200–300 transformed colonies per petri dish. For selection of reverse transcriptase, colonies are then screened for the expression of a thermostable reverse transcriptase as described in the Examples below. Briefly, overnight cultures of individual transformant colonies are assayed directly for thermostable reverse transcriptase activity using a labeled deoxynucleotide and analyzed for the presence of labeled product. If thermostable reverse transcriptase activity is detected, the mutant is sequenced to determine which amino acids maintained reverse transcriptase activity. The gene or nucleic acid molecule encoding a reverse transcriptase of the present invention can be cloned using techniques known to those in the art.

Modifications or Mutations of Polymerases

In accordance with the invention, one or more mutations may be made in any reverse transcriptase in order to increase the thermostability of the enzyme, or confer other properties described herein upon the enzyme, in accordance with the invention. Such mutations include point mutations, frame shift mutations, deletions and insertions. Preferably, one or more point mutations, resulting in one or more amino acid substitutions, are used to produce reverse transcriptases having enhanced or increased thermostability. In a preferred aspect of the invention, one or more mutations at positions equivalent or corresponding to position H204 (e.g., H204R) and/or T306 (e.g., T306K or T306R) of M-MLV reverse transcriptase may be made to produced the desired result in other reverse transcriptases of interest.

In specific embodiments, one or more mutations at positions equivalent or corresponding to position L52, Y64, R116, Y133, K152 Q190, T197, H204, V223, M289, T306 and/or F309 of M-MLV reverse transcriptase may be made to produced a desired result (e.g., increased thermostability, increased fidelity, decreased TdT activity, etc.). Thus, in specific embodiments, using amino acid positions of M-MLV reverse transcriptase as a frame of reference, proteins of the invention include reverse transcriptases (e.g., M-MLV reverse transcriptase, AMV reverse transcriptase, HIV reverse transcriptase, RSV reverse transcriptase, etc.) having one or more of the following alterations: L52P, Y64S, Y64W, Y64R, R116M, Y133A, Y133H, K152R, K152M, Q19° F., T197R, T197E, T197A, T197K, H204R, V223H, V223F, V223I, M289L, T306K, T306R, F309R, and/or F309N, as well as compositions containing these proteins, nucleic acid molecules which encode these proteins, and host cells which contain these nucleic acid molecules.

Mutations in reverse transcriptases which alter thermostability properties of these proteins may be present in conjunction with alterations which either have little or no effect on activities normally associated with reverse transcriptases (e.g., RNase H activity, reverse transcriptase activity, terminal deoxynucleotidyl transferase (TdTase) activity, etc.) or substantially alter one or more activities normally associated with reverse transcriptases. One example of a reverse transcriptase which has such a combination of mutations is a M-MLV reverse transcriptase which has the following alterations: K152M, V223H.

One mutation which has been shown to enhanced the fidelity of SuperScript™II (Invitrogen Corp. (Carlsbad, Calif.) Catalog No. 18064–022) is V223H (see U.S. application Ser. No. 60/189,454, filed Mar. 15, 2000, and U.S. application Ser. No. 09/808,124, filed Mar. 15, 2001, the entire disclosures of each of which are incorporated herein by reference). However, the V223H alteration decreases the thermostability of this enzyme. One mutant was identified, K152M, which suppress the destabilizing effect of enzymes having the V223H mutation. Thus, the invention includes M-MLV reverse transcriptase which contain alterations at positions K152 and V223 and exhibit both increased fidelity and increased thermostability. Specific examples of such reverse transcriptases are those in which K152 is replaced with methionine and V223 is replaced with histidine. Other reverse transcriptases (e.g., AMV reverse transcriptase, HIV reverse transcriptase, RSV reverse transcriptase, etc.) with corresponding alterations are also included within the scope of the invention.

SuperScript™II is an RNase H− reverse transcriptase from M-MLV which has the following substitutions: D524G, E562Q, and D583N (see U.S. Pat. Nos. 5,017,492, 5,244,797, 5,405,776, 5,668,005, and 6,063,608, the entire disclosures of which are incorporated herein by reference).

One or more amino acid substitutions are made at one or more selected positions for any reverse transcriptase of interest. Thus, the amino acids at the selected positions may be substituted with any other amino acid including Ala, Asn, Asp, Cys, Gln, Glu, Gly, His, Ile, Leu, Lys, Met, Phe, Pro, Ser, Thr, Trp, Tyr, and Val. In some preferred embodiments, the selected amino acid will be a non-charged surface residue and will be replaced by a charged residue. In some preferred embodiments, the non-charged surface residue may be replaced by a positively charged amino acid (e.g. lysine or arginine).

The corresponding positions of M-MLV reverse transcriptase identified above may be readily identified for other reverse transcriptases by one with skill in the art. Thus, given the defined region and the assays described in the present application, one with skill in the art can make one or a number of modifications which would result in increased thermostability of any reverse transcriptase of interest. Residues to be modified in accordance with the present invention may include those listed in Table 1 above.

The nucleotide sequences for M-MLV reverse transcriptase (Shinnick et al., 1981, *Nature* 293:543–548; Georgiadis et al., 1995, *Structure* 3:879–892), AMV reverse transcriptase (Joliot et al., 1993, *Virology* 195:812–819), RSV reverse transcriptase (Schwartz et al., 1983, *Cell* 32:853–859), and HIV reverse transcriptase (Wong-Staal et al., 1985, *Nature* 313:277–284) are known.

Preferably, oligonucleotide directed mutagenesis is used to create the mutant reverse transcriptases which allows for all possible classes of base pair changes at any determined site along the encoding DNA molecule.

Enhancing Expression of Reverse Transcriptases

To optimize expression of the reverse transcriptases of the present invention, inducible or constitutive promoters are well known and may be used to express high levels of a reverse transcriptase structural gene in a recombinant host. Similarly, high copy number vectors, well known in the art, may be used to achieve high levels of expression. Vectors having an inducible high copy number may also be useful to enhance expression of the reverse transcriptases of the invention in a recombinant host.

To express the desired structural gene in a prokaryotic cell (such as, *E. coli, B. subtilis, Pseudomonas*, etc.), it is necessary to operably link the desired structural gene to a functional prokaryotic promoter. However, the natural promoter of the reverse transcriptase gene may function in prokaryotic hosts allowing expression of the reverse transcriptase gene. Thus, the natural promoter or other promoters may be used to express the reverse transcriptase gene. Such other promoters that may be used to enhance expression include constitutive or regulatable (i.e., inducible or derepressible) promoters. Examples of constitutive promoters include the int promoter of bacteriophage λ, and the bla promoter of the β-lactamase gene of pBR322. Examples of inducible prokaryotic promoters include the major right and left promoters of bacteriophage λ ($P_R$ and $P_L$), trp, recA, lacZ, lacI, tet, gal, trc, ara BAD (Guzman, et al., 1995, *J. Bacteriol.* 177(14):4121–4130) and tac promoters of *E. coli*. The *B. subtilis* promoters include α-amylase (Ulmanen et al., *J. Bacteriol* 162:176–182 (1985)) and *Bacillus* bacteriophage promoters (Gryczan, T., In: *The Molecular Biology Of Bacilli*, Academic Press, New York (1982)). *Streptomyces* promoters are described by Ward et al., *Mol. Gen. Genet.* 203:468478 (1986)). Prokaryotic promoters are also reviewed by Glick, *J. Ind. Microbiol.* 1:277–282 (1987); Cenatiempto, Y., *Biochimie* 68:505–516 (1986); and Gottesman, *Ann. Rev. Genet.* 18:415–442 (1984). Expression in a prokaryotic cell also requires the presence of a ribosomal binding site upstream of the gene-encoding sequence. Such ribosomal binding sites are disclosed, for example, by Gold et al., *Ann. Rev. Microbiol.* 35:365404 (1981).

To enhance the expression of polymerases of the invention in a eukaryotic cell, well known eukaryotic promoters and hosts may be used. Enhanced expression of the polymerases may be accomplished in a prokaryotic host. One example of a prokaryotic host suitable for use with the present invention is *Escherichia coli*.

Isolation and Purification of Reverse Transcriptases

The enzyme(s) of the present invention is preferably produced by growth in culture of the recombinant host containing and expressing the desired reverse transcriptase gene. However, the reverse transcriptase of the present invention may be isolated from any strain which produces the reverse transcriptase of the present invention. Fragments of the reverse transcriptase are also included in the present invention. Such fragments include proteolytic fragments and fragments having reverse transcriptase activity.

Any nutrient that can be assimilated by a host containing the cloned reverse transcriptase gene may be added to the culture medium. Optimal culture conditions should be selected case by case according to the strain used and the composition of the culture medium. Antibiotics may also be added to the growth media to insure maintenance of vector DNA containing the desired gene to be expressed. Media formulations have been described in DSM or ATCC Catalogs and Sambrook et al., In: *Molecular Cloning, a Laboratory Manual* (2nd ed.), Cold Spring Harbor Laboratory Press, Cold Spring Harbor, N.Y. (1989).

Recombinant host cells producing the reverse transcriptases of this invention can be separated from liquid culture, for example, by centrifugation. In general, the collected microbial cells are dispersed in a suitable buffer, and then broken open by ultrasonic treatment or by other well known procedures to allow extraction of the enzymes by the buffer solution. After removal of cell debris by ultracentrifugation or centrifugation, the reverse transcriptases can be purified by standard protein purification techniques such as extraction, precipitation, chromatography, affinity chromatography, electrophoresis or the like. Assays to detect the presence of the reverse transcriptase during purification are well known in the art and can be used during conventional biochemical purification methods to determine the presence of these enzymes.

In some embodiments, the reverse transcriptases of the present invention may be modified to contain an affinity tag in order to facilitate the purification of the reverse transcriptase. Suitable affinity tags are well known to those skilled in the art and include, but are not limited to, repeated sequences of amino acids such as six histidines, epitopes such as the hemagluttinin epitope and the myc epitope, and other amino acid sequences that permit the simplified purification of the reverse transcriptase.

The reverse transcriptases of the invention preferably have specific activities greater than about 5 units/mg, more preferably greater than about 50 units/mg, still more preferably greater than about 100 units/mg, 250 units/mg, 500 units/mg, 1000 units/mg, 5000 units/mg or 10,000 units/mg, and most preferably greater than about 15,000 units/mg, greater than about 16,000 units/mg, greater than about 17,000 units/mg, greater than about 18,000 units/mg, greater than about 19,000 units/mg and greater than about 20,000 units/mg. In some embodiments, the reverse transcriptases of the present invention may have specific activities greater than about 50,000 units/mg, greater than about 100,000 units/mg, greater than about 150,000 units/mg, greater than about 200,000 units/mg, greater than about 250,000 units/mg and greater than about 300,000 units/mg. Preferred ranges of specific activities for the reverse transcriptases of the invention include a specific activity from about 5 units/mg to about 350,000 units/mg, a specific activity from about 5 units/mg to about 300,000 units/mg, a specific activity of from about 50 units/mg to about 300,000 units/mg, a specific activity from about 100 units/mg to about 300,000 units/mg, a specific activity from about 250 units/mg to about 300,000 units/mg, a specific activity from about 500 units/mg to about 300,000 units/mg, a specific activity from about 1000 units/mg to about 300,000 units/mg, a specific activity from about 5000 units/mg to about 300,000 units/mg, a specific activity from about 10,000 units/mg to about 300,000 units/mg, a specific activity from about 25,000 units/mg to about 300,000 units/mg, a specific activity from about 100 units/mg to about 500 units/mg, a specific activity from about 100 units/mg to about 400 units/mg, and a specific activity from about 200 units/mg to about 500 units/mg. Other preferred ranges of specific activities include a specific activity of from about 200,000 units/mg to about 350,000 units/mg, a specific activity from about 225,000 units/mg to about 300,000 units/mg, and a specific activity from about 250,000 units/mg to about 300,000 units/mg. Preferably, the lower end of the specific activity range may vary from 50, 100, 200, 300, 400, 500, 700, 900, 1,000, 5,000, 10,000, 20,000, 30,000, 35,000, 40,000, 45,000, 50,000, 55,000, 60,000, 65,000, 70,000, 75,000, and 80,000 units/mg, while the upper end of the range may vary from 350,000, 300,000, 250,000, 200,000, 150,000, 140,000, 130,000, 120,000, 110,000, 100,000, and 90,000 units/mg. In some embodiments of the present invention, the specific activity of the thermostable reverse transcriptase prepared in accordance with the present invention may be higher than the specific activity of a non-thermostable reverse transcriptase. In some embodiments, the specific activity of the thermostable reverse transcriptase may be 5%, 10,%, 15%, 20%, 25%, 30%, 40%, 50%, 60%, 70%, 80%, 90%, 100% or more higher than the specific activity of a corresponding non-thermostable reverse transcriptase. In some preferred embodiments, the specific activity of the thermostable reverse transcriptase according to the present invention may be 30% or more higher than the specific activity of a corresponding non-thermostable reverse transcriptase. In accordance with the invention, specific activity is a measurement of the enzymatic activity (in units) of the protein or enzyme relative to the total amount of protein or enzyme used in a reaction. The measurement of a specific activity may be determined by standard techniques well-known to one of ordinary skill in the art.

The reverse transcriptases of the invention may be used to make nucleic acid molecules from one or more templates. Such methods comprise mixing one or more nucleic acid templates (e.g., mRNA, and more preferably a population of mRNA molecules) with one or more of the reverse transcriptases of the invention and incubating the mixture under conditions sufficient to make one or more nucleic acid molecules complementary to all or a portion of the one or more nucleic acid templates.

The invention also relates to methods for the amplification of one or more nucleic acid molecules comprising mixing one or more nucleic acid templates with one of the reverse transcriptases of the invention, and incubating the mixture under conditions sufficient to amplify one or more nucleic acid molecules complementary to all or a portion of the one or more nucleic acid templates. Such amplification methods may further comprise the use of one or more DNA polymerases and may be employed as in standard RT-PCR reactions.

The invention also concerns methods for the sequencing of one or more nucleic acid molecules comprising (a) mixing one or more nucleic acid molecules to be sequenced with one or more primer nucleic acid molecules, one or more reverse transcriptases of the invention, one or more nucleotides and one or more terminating agents; (b) incubating the mixture under conditions sufficient to synthesize a population of nucleic acid molecules complementary to all or a portion of the one or more nucleic acid molecules to be sequenced; and (c) separating the population of nucleic acid molecules to determine the nucleotide sequence of all or a portion of the one or more nucleic acid molecules to be sequenced.

The invention also concerns nucleic acid molecules produced by such methods (which may be full-length cDNA molecules), vectors (particularly expression vectors) comprising these nucleic acid molecules and host cells comprising these vectors and nucleic acid molecules.

Sources of DNA Polymerase

A variety of DNA polymerases are useful in accordance with the present invention. Such polymerases include, but are not limited to, *Thermus thermophilus* (Tth) DNA polymerase, *Thermus aquaticus* (Taq) DNA polymerase, *Thermotoga neapolitana* (Tne) DNA polymerase, *Thermotoga maritima* (Tma) DNA polymerase, *Thermococcus litoralis* (Tli or VENT™) DNA polymerase, *Pyrococcus furiosis* (Pfu) DNA polymerase, *Pyrococcus* species GB-D (DEEPVENT™) DNA polymerase, *Pyrococcus woosii* (Pwo) DNA polymerase, *Bacillus sterothennophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, *Mycobacterium* spp. DNA polymerase (Mtb, Mlep), and mutants, variants and derivatives thereof.

DNA polymerases used in accordance with the invention may be any enzyme that can synthesize a DNA molecule from a nucleic acid template, typically in the 5' to 3' direction. Such polymerases may be mesophilic or thermophilic, but are preferably thermophilic. Mesophilic polymerases include T5 DNA polymerase, T7 DNA polymerase, Klenow fragment DNA polymerase, DNA polymerase III, and the like. Preferred DNA polymerases are thermostable DNA polymerases such as Taq, Tne, Tma, Pfu, VENT™, DEEPVENT™, Tth and mutants, variants and derivatives thereof (U.S. Pat. Nos. 5,436,149; 5,512,462; PCT Publication No. WO 92/06188; PCT Publication No. WO 92/06200; PCT Publication No. WO 96/10640; Barnes, W. M., *Gene* 112:29–35 (1992); Lawyer, F. C., et al., *PCR Meth. application* 2:275–287 (1993); Flaman, J.-M., et al., *Nucl. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3' exonuclease activity) are typically used. See U.S. Pat. Nos. 5,436,149; 5,512,462; Barnes, W. M., *Gene* 112:29–35 (1992); PCT Publication No. WO 98/06736; and commonly owned, co-pending U.S. patent application Ser. No. 08/801,720, filed Feb. 14, 1997, the disclosures of all of which are incorporated herein in their entireties. Examples of DNA polymerases substantially lacking in 3' exonuclease activity include, but are not limited to, Taq, Tne(exo⁻), Tma, Pfu(exo⁻), Pwo and Tth DNA polymerases, and mutants, variants and derivatives thereof. Nonlimiting examples of DNA polymerases having 3' exonuclease activity include Pfu, DEEPVENT™ and Tli/VENT™ and mutants, variants and derivatives thereof.

Formulation of Enzyme Compositions

To form the compositions of the present invention, one or more reverse transcriptases are preferably admixed in a buffered salt solution. One or more DNA polymerases and/or one or more nucleotides, and/or one or more primers may optionally be added to make the compositions of the invention. More preferably, the enzymes are provided at working concentrations in stable buffered salt solutions. The terms "stable" and "stability" as used herein generally mean the retention by a composition, such as an enzyme composition, of at least 70%, preferably at least 80%, and most preferably at least 90%, of the original enzymatic activity (in units) after the enzyme or composition containing the enzyme has been stored for about one week at a temperature of about 4° C., about two to six months at a temperature of about −20° C., and about six months or longer at a temperature of about −80° C. As used herein, the term "working concentration" means the concentration of an enzyme that is at or near the optimal concentration used in a solution to perform a particular function (such as reverse transcription of nucleic acids).

The water used in forming the compositions of the present invention is preferably distilled, deionized and sterile filtered (through a 0.1–0.2 micrometer filter), and is free of contamination by DNase and RNase enzymes. Such water is available commercially, for example from Sigma Chemical Company (Saint Louis, Mo.), or may be made as needed according to methods well known to those skilled in the art.

In addition to the enzyme components, the present compositions preferably comprise one or more buffers and cofactors necessary for synthesis of a nucleic acid molecule such as a cDNA molecule. Particularly preferred buffers for use in forming the present compositions are the acetate, sulfate, hydrochloride, phosphate or free acid forms of Tris-(hydroxymethyl)aminomethane (TRIS®), although alternative buffers of the same approximate ionic strength and pKa as TRIS® may be used with equivalent results. In addition to the buffer salts, cofactor salts such as those of potassium (preferably potassium chloride or potassium acetate) and magnesium (preferably magnesium chloride or magnesium acetate) are included in the compositions. Addition of one or more carbohydrates and/or sugars to the compositions and/or synthesis reaction mixtures may also be advantageous, to support enhanced stability of the compositions and/or reaction mixtures upon storage. Preferred such carbohydrates or sugars for inclusion in the compositions and/or synthesis reaction mixtures of the invention include, but are not limited to, sucrose, trehalose, glycerol, and the like. Furthermore, such carbohydrates and/or sugars may be added to the storage buffers for the enzymes used in the production of the enzyme compositions and kits of the invention. Such carbohydrates and/or sugars are commercially available from a number of sources, including Sigma (St. Louis, Mo.).

It is often preferable to first dissolve the buffer salts, cofactor salts and carbohydrates or sugars at working concentrations in water and to adjust the pH of the solution prior to addition of the enzymes. In this way, the pH-sensitive enzymes will be less subject to acid- or alkaline-mediated inactivation during formulation of the present compositions.

To formulate the buffered salts solution, a buffer salt which is preferably a salt of Tris(hydroxymethyl)aminomethane (TRIS®), and most preferably the hydrochloride salt thereof, is combined with a sufficient quantity of water to yield a solution having a TRIS® concentration of 5–150 millimolar, preferably 10–60 millimolar, and most preferably about 20–60 millimolar. To this solution, a salt of magnesium (preferably either the chloride or acetate salt thereof) may be added to provide a working concentration thereof of 1–10 millimolar, preferably 1.5–8.0 millimolar, and most preferably about 3–7.5 millimolar. A salt of potassium (preferably a chloride or acetate salt of potassium) may also be added to the solution, at a working concentration of 10–100 millimolar and most preferably about 75 millimolar. A reducing agent such as dithiothreitol may be added to the solution, preferably at a final concentration of about 1–100 mM, more preferably a concentration of about 5–50 mM or about 7.5–20 mM, and most preferably at a concentration of about 10 mM. Preferred concentrations of carbohydrates and/or sugars for inclusion in the compositions of the invention range from about 5% (w/v) to about 30% (w/v), about 7.5% (w/v) to about 25% (w/v), about 10% (w/v) to about 25% (w/v), about 10% (w/v) to about 20% (w/v), and preferably about 10% (w/v) to about 15% (w/v). A small amount of a salt of ethylenediaminetetraacetate (EDTA), such as disodium EDTA, may also be added (preferably about 0.1 millimolar), although inclusion of EDTA does not appear to be essential to the function or stability of the compositions of the present invention. After addition of all buffers and salts, this buffered salt solution is mixed well until all salts are dissolved, and the pH is adjusted using methods known in the art to a pH value of 7.4 to 9.2, preferably 8.0 to 9.0, and most preferably about 8.4.

To these buffered salt solutions, the enzymes (reverse transcriptases and/or DNA polymerases) are added to produce the compositions of the present invention. M-MLV reverse transcriptases are preferably added at a working concentration in the solution of about 1,000 to about 50,000 units per milliliter, about 2,000 to about 30,000 units per milliliter, about 2,500 to about 25,000 units per milliliter, about 3,000 to about 22,500 units per milliliter, about 4,000 to about 20,000 units per milliliter, and most preferably at a working concentration of about 5,000 to about 20,000 units per milliliter. AMV reverse transcriptases, RSV reverse transcriptases and HIV reverse transcriptases, including those of the invention described above, are preferably added at a working concentration in the solution of about 100 to about 5000 units per milliliter, about 125 to about 4000 units per milliliter, about 150 to about 3000 units per milliliter, about 200 to about 2500 units per milliliter, about 225 to about 2000 units per milliliter, and most preferably at a working concentration of about 250 to about 1000 units per milliliter. The enzymes in the thermophilic DNA polymerase group (Taq, Tne, Tma, Pfu, VENT, DEEPVENT, Tth and mutants, variants and derivatives thereof) are preferably added at a working concentration in the solution of about 100 to about 1000 units per milliliter, about 125 to about 750 units per milliliter, about 150 to about 700 units per milliliter, about 200 to about 650 units per milliliter, about 225 to about 550 units per milliliter, and most preferably at a working concentration of about 250 to about 500 units per milliliter. The enzymes may be added to the solution in any order, or may be added simultaneously.

The compositions of the invention may further comprise one or more nucleotides, which are preferably deoxynucleoside triphosphates (dNTPs) or dideoxynucleoside triphosphates (ddNTPs). The dNTP components of the present compositions serve as the "building blocks" for newly synthesized nucleic acids, being incorporated therein by the action of the polymerases, and the ddNTPs may be used in sequencing methods according to the invention. Examples of nucleotides suitable for use in the present compositions include, but are not limited to, dUTP, dATP, dTTP, dCTP, dGTP, dITP, 7-deaza-dGTP, α-thio-dATP, α-thio-dTTP, α-thio-dGTP, α-thio-dCTP, ddUTP, ddATP, ddTTP, ddCTP, ddGTP, ddITP, 7-deaza-ddGTP, α-thio-ddATP, α-thio-ddTTP, α-thio-ddGTP, α-thio-ddCTP or derivatives thereof, all of which are available commercially from sources including Invitrogen Corp. (Carlsbad, Calif.), New England BioLabs (Beverly, Mass.) and Sigma Chemical Company (Saint Louis, Mo.). The nucleotides may be unlabeled, or they may be detectably labeled by coupling them by methods known in the art with radioisotopes (e.g., $^3$H, $^{14}$C, 32P or 35S), vitamins (e.g., biotin), fluorescent moieties (e.g., fluorescein, rhodamine, Texas Red, or phycoerythrin), chemiluminescent labels (e.g., using the PHOTO-GENE™ or ACES™ chemiluminescence systems, available commercially from Invitrogen Corp. (Carlsbad, Calif.)), dioxigenin and the like. Labeled nucleotides may also be obtained commercially, for example from Invitrogen Corp. (Carlsbad, Calif.) or Sigma Chemical Company (Saint Louis, Mo.). In the present compositions, the nucleotides are added to give a working concentration of each nucleotide of about 10–4000 micromolar, about 50–2000 micromolar, about 100–1500 micromolar, or about 200–1200 micromolar, and most preferably a concentration of about 1000 micromolar.

To reduce component deterioration, storage of the reagent compositions is preferably at about 4° C. for up to one day, or most preferably at −20° C. for up to one year.

In another aspect, the compositions and reverse transcriptases of the invention may be prepared and stored in dry form in the presence of one or more carbohydrates, sugars, or synthetic polymers. Preferred carbohydrates, sugars or polymers for the preparation of dried compositions or reverse transcriptases include, but are not limited to, sucrose, trehalose, and polyvinylpyrrolidone (PVP) or combinations thereof. See, e.g., U.S. Pat. Nos. 5,098,893, 4,891,319, and 5,556,771, the disclosures of which are entirely incorporated herein by reference. Such dried compositions and enzymes may be stored at various temperatures for extended times without significant deterioration of enzymes or components of the compositions of the invention. Preferably, the dried reverse transcriptases or compositions are stored at 4° C. or at −20° C.

Production/Sources of cDNA Molecules

In accordance with the invention, cDNA molecules (single-stranded or double-stranded) may be prepared from a variety of nucleic acid template molecules. Preferred nucleic acid molecules for use in the present invention include single-stranded or double-stranded DNA and RNA molecules, as well as double-stranded DNA:RNA hybrids. More preferred nucleic acid molecules include messenger RNA (mRNA), transfer RNA (tRNA) and ribosomal RNA (rRNA) molecules, although mRNA molecules are the preferred template according to the invention.

The nucleic acid molecules that are used to prepare cDNA molecules according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi (especially yeasts), plants, protozoans and other parasites, and animals including insects (particularly *Drosophila* spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid molecules (such as mRNA) may be isolated therefrom by methods that are well-known in the art (See, e.g., Maniatis, T., et al., *Cell* 15:687–701 (1978); Okayama, H., and Berg, P., *Mol. Cell. Biol.* 2:161–170 (1982); Gubler, U., and Hoffman, B. J., *Gene* 25:263–269 (1983)). The nucleic acid molecules thus isolated may then be used to prepare cDNA molecules and cDNA libraries in accordance with the present invention.

In the practice of the invention, cDNA molecules or cDNA libraries are produced by mixing one or more nucleic acid molecules obtained as described above, which is preferably one or more mRNA molecules such as a population of mRNA molecules, with a polypeptide having reverse transcriptase activity of the present invention, or with one or more of the compositions of the invention, under conditions favoring the reverse transcription of the nucleic acid molecule by the action of the enzymes or the compositions to form one or more cDNA molecules (single-stranded or double-stranded). Thus, the method of the invention comprises (a) mixing one or more nucleic acid templates (preferably one or more RNA or mRNA templates, such as a population of mRNA molecules) with one or more reverse transcriptases of the invention and (b) incubating the mixture under conditions sufficient to make one or more nucleic acid molecules complementary to all or a portion of the one or more templates. Such methods may include the use of one or more DNA polymerases, one or more nucleotides, one or more primers, one or more buffers, and the like. The invention may be used in conjunction with methods of cDNA synthesis such as those described in the Examples below, or others that are well-known in the art (see, e.g., Gubler, U., and Hoffman, B. J., *Gene* 25:263–269 (1983); Krug, M. S., and Berger, S. L., *Meth. Enzymol.* 152:316–325 (1987); Sambrook, J., et al., *Molecular Cloning: A Laboratory Manual*, 2nd ed., Cold Spring Harbor, N.Y.: Cold Spring Harbor Laboratory Press, pp. 8.60–8.63 (1989); PCT Publication No. WO 99/15702; PCT Publication No. WO 98/47912; and PCT Publication No. WO 98/51699), to produce cDNA molecules or libraries.

Other methods of cDNA synthesis which may advantageously use the present invention will be readily apparent to one of ordinary skill in the art.

Having obtained cDNA molecules or libraries according to the present methods, these cDNAs may be isolated for further analysis or manipulation. Detailed methodologies for purification of cDNAs are taught in the GENETRAPPER™ manual (Invitrogen Corp. (Carlsbad, Calif.)), which is incorporated herein by reference in its entirety, although alternative standard techniques of cDNA isolation that are known in the art (see, e.g., Sambrook, J., et al., *Molecular Cloning: A Laboratory Manual*, 2nd ed., Cold Spring Harbor, N.Y.: Cold Spring Harbor Laboratory Press, pp. 8.60–8.63 (1989)) may also be used.

In other aspects of the invention, the invention may be used in methods for amplifying and sequencing nucleic acid molecules. Nucleic acid amplification methods according to this aspect of the invention may be one- step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with one or more reverse transcriptases of the present invention and with one or more DNA polymerases and (b) incubating the mixture under conditions sufficient to amplify a nucleic acid molecule complementary to all or a portion of the template. Such amplification may be accomplished by the reverse transcriptase activity alone or in combination with the DNA polymerase activity. Two-step RT-PCR reactions may be accomplished in two separate steps. Such a method comprises (a) mixing a nucleic acid template (e.g., mRNA) with a reverse transcriptase of the present invention, (b) incubating the mixture under conditions sufficient to make a nucleic acid molecule (e.g., a DNA molecule) complementary to all or a portion of the template, (c) mixing the nucleic acid molecule with one or more DNA polymerases and (d) incubating the mixture of step (c) under conditions sufficient to amplify the nucleic acid molecule. For amplification of long nucleic acid molecules (i.e., greater than about 3–5 Kb in length), a combination of DNA polymerases may be used, such as one DNA polymerase having 3' exonuclease activity and another DNA polymerase being substantially reduced in 3' exonuclease activity.

Nucleic acid sequencing methods according to this aspect of the invention may comprise both cycle sequencing (sequencing in combination with amplification) and standard sequencing reactions. The sequencing method of the invention thus comprises (a) mixing a nucleic acid molecule to be sequenced with one or more primers, one or more reverse transcriptases of the invention, one or more nucleotides and one or more terminating agents, (b) incubating the mixture under conditions sufficient to synthesize a population of nucleic acid molecules complementary to all or a portion of the molecule to be sequenced, and (c) separating the population to determine the nucleotide sequence of all or a portion of the molecule to be sequenced. According to the invention, one or more DNA polymerases (preferably thermostable DNA polymerases) may be used in combination with or separate from the reverse transcriptases of the invention.

Amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822), as well as more complex PCR-based nucleic acid fingerprinting techniques such as Random Amplified Polymorphic DNA (RAPD) analysis (Williams, J. G. K., et al., *Nucl. Acids Res.* 18(22):6531–6535, 1990), Arbitrarily Primed PCR (AP-PCR; Welsh, J., and McClelland, M., *Nucl. Acids Res.* 18(24):7213–7218, 1990), DNA Amplification Fingerprinting (DAF; Caetano-Anollés et al., *Bio/Technology* 9:553–557, 1991), microsatellite PCR or Directed Amplification of Minisatellite-region DNA (DAMD; Heath, D. D., et al., *Nucl. Acids Res.* 21(24): 5782–5785, 1993), and Amplification Fragment Length Polymorphism (AFLP) analysis (EP 0 534 858; Vos, P., et al., *Nucl. Acids Res.* 23(21):4407–4414, 1995; Lin, J. J., and Kuo, J., *FOCUS* 17(2):66–70, 1995). Nucleic acid sequencing techniques which may employ the present compositions include dideoxy sequencing methods such as those disclosed in U.S. Pat. Nos. 4,962,022 and 5,498,523. In a particularly preferred aspects, the invention may be used in methods of amplifying or sequencing a nucleic acid molecule comprising one or more polymerase chain reactions (PCRs), such as any of the PCR-based methods described above.

Kits

In another embodiment, the present invention may be assembled into kits for use in reverse transcription or amplification of a nucleic acid molecule, or into kits for use in sequencing of a nucleic acid molecule. Kits according to this aspect of the invention comprise a carrier means, such as a box, carton, tube or the like, having in close confinement therein one or more container means, such as vials, tubes, ampules, bottles and the like, wherein a first container means contains one or more polypeptides of the present invention having reverse transcriptase activity. When more than one polypeptide having reverse transcriptase activity is used, they may be in a single container as mixtures of two or more polypeptides, or in separate containers. The kits of the invention may also comprise (in the same or separate containers) one or more DNA polymerases, a suitable buffer, one or more nucleotides and/or one or more primers.

In a specific aspect of the invention, the reverse transcription and amplification kits may comprise one or more components (in mixtures or separately) including one or more polypeptides having reverse transcriptase activity of the invention, one or more nucleotides needed for synthesis of a nucleic acid molecule, and/or one or more primers (e.g., oligo(dT) for reverse transcription). Such reverse transcription and amplification kits may further comprise one or more DNA polymerases. Sequencing kits of the invention may comprise one or more polypeptides having reverse transcriptase activity of the invention, and optionally one or more DNA polymerases, one or more terminating agents (e.g., dideoxynucleoside triphosphate molecules) needed for sequencing of a nucleic acid molecule, one or more nucleotides and/or one or more primers. Preferred polypeptides having reverse transcriptase activity, DNA polymerases, nucleotides, primers and other components suitable for use in the reverse transcription, amplification and sequencing kits of the invention include those described above. The kits encompassed by this aspect of the present invention may further comprise additional reagents and compounds necessary for carrying out standard nucleic acid reverse transcription, amplification or sequencing protocols. Such polypeptides having reverse transcriptase activity of the invention, DNA polymerases, nucleotides, primers, and additional reagents, components or compounds may be contained in one or more containers, and may be contained in such containers in a mixture of two or more of the above-noted components or may be contained in the kits of the invention in separate containers.

Use of Nucleic Acid Molecules

The nucleic acid molecules or cDNA libraries prepared by the methods of the present invention may be further characterized, for example by cloning and sequencing (i.e., determining the nucleotide sequence of the nucleic acid molecule), by the sequencing methods of the invention or by others that are standard in the art (see, e.g., U.S. Pat. Nos. 4,962,022 and 5,498,523, which are directed to methods of DNA sequencing). Alternatively, these nucleic acid molecules may be used for the manufacture of various materials in industrial processes, such as hybridization probes by methods that are well-known in the art. Production of hybridization probes from cDNAs will, for example, provide the ability for those in the medical field to examine a patient's cells or tissues for the presence of a particular genetic marker such as a marker of cancer, of an infectious or genetic disease, or a marker of embryonic development. Furthermore, such hybridization probes can be used to isolate DNA fragments from genomic DNA or cDNA libraries prepared from a different cell, tissue or organism for further characterization.

The nucleic acid molecules of the present invention may also be used to prepare compositions for use in recombinant DNA methodologies. Accordingly, the present invention relates to recombinant vectors which comprise the cDNA or amplified nucleic acid molecules of the present invention, to host cells which are genetically engineered with the recombinant vectors, to methods for the production of a recombinant polypeptide using these vectors and host cells, and to recombinant polypeptides produced using these methods.

Recombinant vectors may be produced according to this aspect of the invention by inserting, using methods that are well-known in the art, one or more of the cDNA molecules or amplified nucleic acid molecules prepared according to the present methods into a vector. The vector used in this aspect of the invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression (and are therefore termed "expression vectors"), which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the cDNA or amplified nucleic acid molecules of the invention should be operatively linked to an appropriate promoter, such as the phage lambda PL promoter, the *E. coli* lac, trp and tac promoters. Other suitable promoters will be known to the skilled artisan.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; pGEX, pTrxfus, pTrc99a, pET-5, pET-9, pKK223-3, pKK233-3, pDR540, pRIT5 available from Pharmacia; and pSPORT1, pSPORT2 and pSV.SPORT1, available from Invitrogen Corp. (Carlsbad, Calif.). Other suitable vectors will be readily apparent to the skilled artisan.

The invention also provides methods of producing a recombinant host cell comprising the cDNA molecules, amplified nucleic acid molecules or recombinant vectors of the invention, as well as host cells produced by such methods. Representative host cells (prokaryotic or eukaryotic) that may be produced according to the invention include, but are not limited to, bacterial cells, yeast cells, plant cells and animal cells. Preferred bacterial host cells include *Escherichia coli* cells (most particularly *E. coli* strains DH10B and Stb12, which are available commercially (Invitrogen Corp. (Carlsbad, Calif.)), *Bacillus subtilis* cells, *Bacillus megaterium* cells, *Streptomyces* spp. cells, *Erwinia* spp. cells, *Klebsiella* spp. cells and *Salmonella typhimurium* cells. Preferred animal host cells include insect cells (most particularly *Spodoptera frugiperda* Sf9 and Sf21 cells and Trichoplusa HigH-Five cells) and mammalian cells (most particularly CHO, COS, VERO, BHK and human cells). Such host cells may be prepared by well-known transformation, electroporation or transfection techniques that will be familiar to one of ordinary skill in the art.

In addition, the invention provides methods for producing a recombinant polypeptide, and polypeptides produced by these methods. According to this aspect of the invention, a recombinant polypeptide may be produced by culturing any of the above recombinant host cells under conditions favoring production of a polypeptide therefrom, and isolation of the polypeptide. Methods for culturing recombinant host cells, and for production and isolation of polypeptides therefrom, are well-known to one of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Preparation of Mutant Reverse Transcriptases

Figure 1:
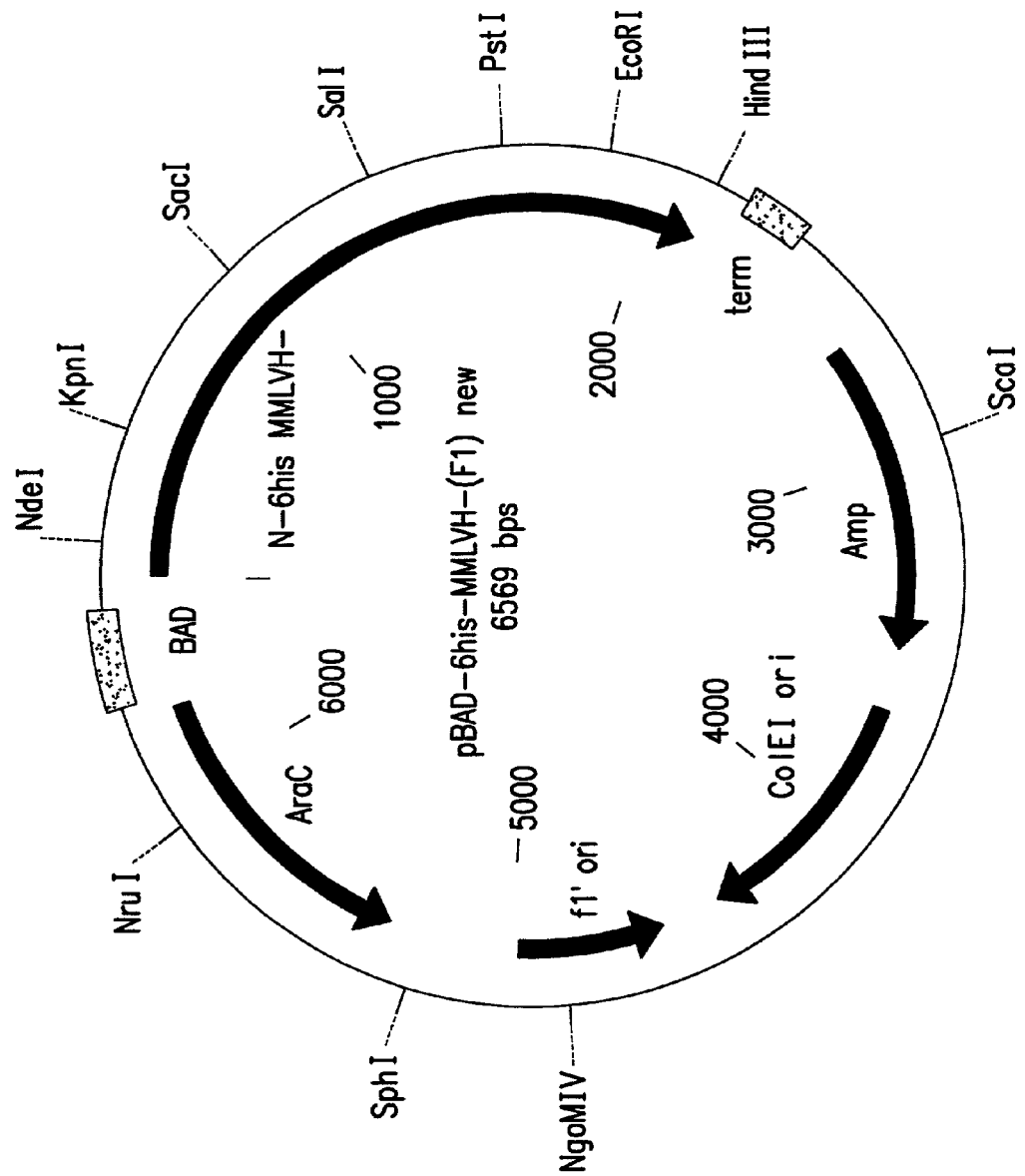
FIG. 1 is a map of plasmid pBAD-6-His-M-MLV H– (F1).

Plasmid pBAD was obtained from Invitrogen and the coding sequence of M-MLV reverse transcriptase was inserted to produce plasmid pBAD-6-His-M-MLV H– (F1). Plasmid pBAD-6-His-M-MLV H-(F1) was used as both a cloning vector and as a target for PCR mutagenesis (FIG. 1). pBAD-6-His-M-MLV H- (F1) replicates in *E. coli* and confers ampicillin resistance to transformed cells. The M-MLV reverse transcriptase gene is expressed from the ara BAD promoter which is induced by the presence of arabinose. The promoter is repressed by the product of the araC gene, which is present on the plasmid. The host used, *E. coli* strain DH10B, is an araD mutant and cannot metabolize arabinose, making arabinose a gratuitous inducer in DH10B cells transformed with pBAD-6-His-M-MLV H-(F1). The plasmid contains a 6 histidine containing leader sequence in frame with the coding sequence of the M-MLV reverse transcriptase gene. With reference to the sequence of this plasmid provided in Table 3 (SEQ ID NOs:1 and 2), nucleotides 1–96 encode the leader sequence and nucleotides 97–99 encode a methionine. Those skilled in the art will appreciate that the wild-type M-MLV reverse transcriptase is derived by proteolysis from a precursor polyprotein and thus the wild-type M-MLV reverse transcriptase does not start with a methionine. Therefore, amino acid number 1 of the M-MLV reverse transcriptase is the threonine following the methionine encoded by nucleotides 97–99.

The sequence of the M-MLV reverse transcriptase gene in pBAD-6-His-M-MLV H- (F1) which was used in these experiments was derived from the sequence of plasmid pRT601. pRT601 is described in U.S. Pat. Nos. 5,668,005 and 5,017,492, which are incorporated herein by reference in their entireties.

TABLE 3

|  |  |  |  |  |  |  |
|---|---|---|---|---|---|---|
| 1 | atgggggtt<br>m g g | ctcatcatca<br>s h h | tcatcatcat<br>h h h h | ggtatggcta<br>g m a | gcatgactgg<br>s m t | tggacagcaa<br>g q q |
| 61 | atgggtcggg<br>m g r | atctgtacga<br>d l y | cgatgacgat<br>d d d d | aagcatatga<br>k h m | ccctaaatat<br>t l n | agaagatgag<br>i e d e |
| 121 | tatcggctac<br>y r l | atgagacctc<br>h e t | aaaagagcca<br>s k e p | gatgtttctc<br>d v s | tagggtccac<br>l g s | atggctgtct<br>t w l s |
| 181 | gattttcctc<br>d f p | aggcctgggc<br>q a w | ggaaaccggg<br>a e t g | ggcatgggac<br>g m g | tggcagttcg<br>l a v | ccaagctcct<br>r q a p |
| 241 | ctgatcatac<br>l i i | ttctgaaagc<br>l l k | aacctctacc<br>a t s t | cccgtgtcca<br>p v s | taaaacaata<br>i k q | ccccatgtca<br>y p m s |
| 301 | caagaagcca<br>q e a | gactggggat<br>r l g | caagcccac<br>i k p h | atacagagac<br>i q r | tgttggacca<br>l l d | gggaatactg<br>q g i l |
| 361 | gtaccctgcc<br>v p c | agtccccctg<br>q s p | gaacacgccc<br>w n t p | ctgctacccg<br>l l p | tcaagaaacc<br>v k k | cgggactaat<br>p g t n |
| 421 | gattacaggc<br>d y r | ctgtccaaga<br>p v q | tctgagagag<br>d l r e | gtcaacaaac<br>v n k | gcgtagaaga<br>r v e | catccacccc<br>d i h p |
| 481 | accgtaccca<br> | accctacaa<br> | cctcttgagt<br> | gggctcccac<br> | cgtcccacca<br> | gtggtacact<br> |

TABLE 3-continued

```
           t  v  p       n  l  l  s       g  l  p       p  s  h       q  w  y  t
 541 gttctagact  taaaagatgc  cttttcctgc  ctgagactcc  acccgacgtc  tcagcctctc
       v  l  d       l  k  d       a  f  f  c       l  r  l       h  p  t       s  q  p  l
 601 ttcgccttg   aatggagaga  cccagagatg  ggaatctctg  gccaactaac  ctggaccaga
       f  a  f       e  w  r       d  p  e  m       g  i  s       g  q  l       t  w  t  r
 661 ctcccacagg  gattcaaaaa  cagtcccacc  ctgtttgatg  aggcactgcg  cagagaccta
       l  p  q       g  f  k       n  s  p  t       l  f  d       e  a  l       r  r  d  l
 721 gcagacttcc  ggatccagca  cccagacttg  atcctgctac  agtacgtaga  tgacttactg
       a  d  f       r  i  q       h  p  d  l       i  l  l       q  y  v       d  d  l  l
 781 ctggccgcca  cttctgagct  cgactgccaa  caaggtactc  gggccctgtt  acaaaccta
       l  a  a       t  s  e       l  d  c  q       q  g  t       r  a  l       l  q  t  l
 841 ggagacctcg  ggtatcgggc  ctcggccaag  aaagcccaaa  tttgccagaa  acaggtcaag
       g  d  l       g  y  r       a  s  a  k       k  a  q       i  c  q       k  q  v  k
 901 tatctggggt  atcttctaaa  agagggtcag  agatggctga  ctgaggccag  aaaagagact
       y  l  g       y  l  l       k  e  g  q       r  w  l       t  e  a       r  k  e  t
 961 gtgatggggc  agcctactcc  gaagacccg   cggcaactaa  gggagttcct  agggacggca
       v  m  g       q  p  t       p  k  t  p       r  q  l       r  e  f       l  g  t  a
1021 ggcttctgtc  gcctctggat  ccctgggttt  gcagaaatgg  cagcccctt   gtaccctctc
       g  f  c       r  l  w       i  p  g  f       a  e  m       a  a  p       l  y  p  l
1081 accaaaacgg  ggactctgtt  taattgggc   ccagaccaac  aaaaggccta  tcaagaaatc
       t  k  t       g  t  l       f  n  w  g       p  d  q       q  k  a       y  q  e  i
1141 aagcaagctc  ttctaactgc  cccagccctg  gggttgccag  atttgactaa  gccctttgaa
       k  q  a       l  l  t       a  p  a  l       g  l  p       d  l  t       k  p  f  e
1201 ctctttgtcg  acgagaagca  gggctacgcc  aaaggtgtcc  taacgcaaaa  actgggacct
       l  f  v       d  e  k       q  g  y  a       k  g  v       l  t  q       k  l  g  p
1261 tggcgtcggc  cggtggccta  cctgtccaaa  aagctagacc  cagtagcagc  tgggtggccc
       w  r  r       p  v  a       y  l  s  k       k  l  d       p  v  a       g  w  p
1321 ccttgcctac  ggatggtagc  agccattgcc  gtactgacaa  aggatgcagg  caagctaacc
       p  c  l       r  m  v       a  a  i  a       v  l  t       k  d  a       g  k  l  t
1381 atgggacagc  cactagtcat  tctggccccc  catgcagtag  aggcactagt  caaacaaccc
       m  g  q       p  l  v       i  l  a  p       h  a  v       e  a  l       v  k  q  p
1441 cccgatcgat  ggcttccaa   cgcccggatg  actcactatc  aggccttgct  tttggacacg
       p  d  r       w  l  s       n  a  r  m       t  h  y       q  a  l       l  l  d  t
1501 gaccgggtcc  agttcggacc  ggtggtagcc  ctgaacccgg  ctacactgct  cccactgcct
       d  r  v       q  f  g       p  v  v  a       l  n  p       a  t  l       l  p  l  p
1561 gaggaagggc  tgcagcacaa  ctgccttgat  atcctggccg  aagcccacgg  aacccgaccc
       e  e  g       l  q  h       n  c  l  d       i  l  a       e  a  h       g  t  r  p
1621 gacctaacgg  accagccgct  cccagacgcc  gaccacacct  ggtacacggg  tggatccagt
       d  l  t       d  q  p       l  p  d  a       d  h  t       w  y  t       g  g  s  s
1681 ctcttgcaag  agggacagcg  taaggcggga  gctgcggtga  ccaccgagac  cgaggtaatc
       l  l  q       e  g  q       r  k  a  g       a  a  v       t  t  e       t  e  v  i
1741 tgggctaaag  ccctgccagc  cgggacatcc  gctcagcggg  ctcagctgat  agcactcacc
       w  a  k       a  l  p       a  g  t  s       a  q  r       a  q  l       i  a  l  t
1801 caggccctaa  ggatggcaga  aggtaagaag  ctaaatgttt  atacgaattc  ccgttatgct
       q  a  l       r  m  a       e  g  k  k       l  n  v       y  t  n       s  r  y  a
1861 tttgctactg  cccatatcca  tggagaaata  tacagaaggc  gtgggttgct  cacatcagaa
       f  a  t       a  h  i       h  g  e  i       y  r  r       r  g  l       l  t  s  e
1921 ggcaaagaga  tcaaaaataa  ggacgagata  ttggccctac  taaaagccct  ctttctgccc
       g  k  e       i  k  n       k  d  e  i       l  a  l       l  k  a       l  f  l  p
1981 aaaagactta  gcataatcca  ttgtccagga  catcaaaagg  gacacagcgc  cgaggctaga
       k  r  l       s  i  i       h  c  p  g       h  q  k       g  h  s       a  e  a  r
```

TABLE 3-continued

```
2041 ggcaaccgga  tggctgacca  agcggcccga  aaggcagcca  tcacagagaa  tccagacacc
        g  n  r    m  a  d    q  a  a  r    k  a  a    i  t  e    n  p  d  t 2101 tctaccctcc  tcatagaaaa  ttcatcaccc  aattcccgct  taattaatta  a
        s  t  l    l  i  e    n  s  s  p    n  s  r    l  i  n    -
```

Table 4 provides a list of the point mutations introduced in the M-MLV reverse transcriptase coding sequence of pRT601 to produce the plasmid used. The numbering of the point mutations corresponds to the nucleotide sequence presented in Table 3.

TABLE 4

| Nucleotide # in Table 3 | change | Nucleotide # in Table 3 | change |
|---|---|---|---|
| 411 | a→c | 993 | a→g |
| 459 | g→a | 1446 | c→t |
| 462 | g→c | 1449 | c→a |
| 543 | g→t | 1670 | a→g |
| 546 | t→a | 1675 | a→t |
| 585 | c→g | 1676 | g→c |
| 588 | c→g | 1783 | g→c |
| 589 | a→t | 1785 | a→g |
| 590 | g→c | 1845 | t→g |
| 639 | a→t | 1846 | g→a |
| 642 | a→c | 1849 | a→t |
| 710 | a→g | 1850 | g→c |
| 801 | a→c | 1950 | c→a |
| 990 | t→g | | |

The mutations which were introduced to make RNAse H– mutants of M-MLV reverse transcriptase are D524G, D583N, and E562Q. The remaining mutations were introduced to insert or remove restriction enzyme sites to facilitate the production of appropriately sized segments for the random PCR mutagenesis. This RNase H– mutant is referred to herein as SuperScript™II or SuperScript™II gene.

Figure 2:
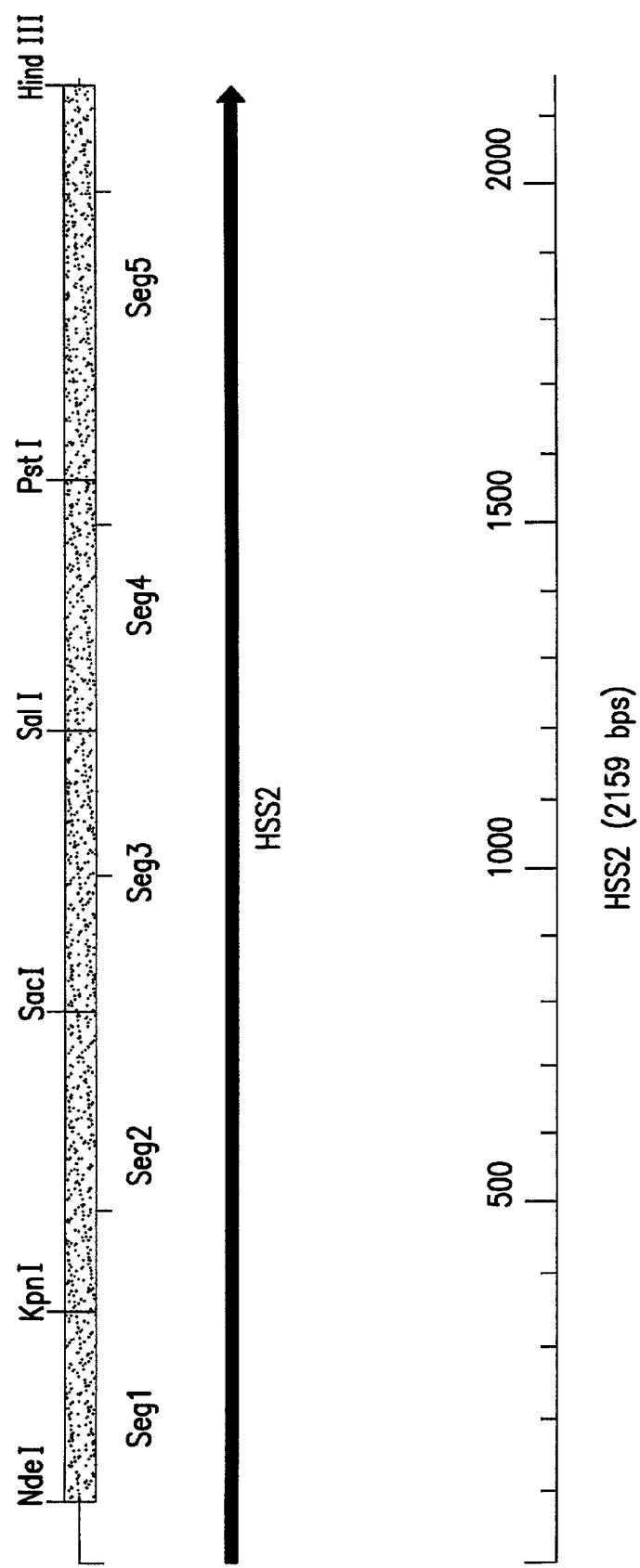
FIG. 2 is a linear representation of the coding sequence of the M-MLV reverse transcriptase showing the locations of the restriction enzyme cleavage sites used to generate the segments of the gene used to generate mutations.

The sequence of the M-MLV reverse transcriptase was engineered to introduce restriction enzyme cleavage sites as shown schematically in FIG. 2 without changing the amino acids encoded by the sequence. The sequence was divided into 5 segments and oligonucleotides were designed so that each segment could be amplified.

Segments were prepared from pBAD-6-His-M-MLV H– (F1) by restriction enzyme digests and the segments were gel purified away from the vector backbone. Each segment was randomly mutagenized by PCR in the presence of manganese. The PCR conditions were standard except that 0.25 mM $MnCl_2$ was present, and the nucleotide triphosphate concentration was limited to 20 µM of each dNTP (50 mM Tris.HCl pH 8.3, 50 mM KCl, 3 MM $MgCl_2$, 20 µM dGTP, 20 µM dCTP, 20 µM dATP, 20 µM dTTP, 1 unit Taq DNA polymerase per 100 µl reaction). The PCR product was extracted with phenol-chloroform, precipitated with ethanol and the mutated segments were cloned into a vector from which the given segment had been removed. Libraries of transformants for each mutated segment were screened for thermostable variants.

Example 2

Screening for Thermostable Reverse Transcriptases

In this example the following solutions were used:

EG—per liter: 20 g bacto-tryptone, 10 g bacto yeast extract, 2 ml glycerol, 0.54 g NaCl, 0.194 g KCl EG-arabinose—150 ml EG plus 1.5 ml of 10 mg/ml ampicillin and 1.5 ml of 20% (w/v) arabinose (if plates are to have arabinose)

20×PEB-I Buffer—18% (w/v) glucose, 500 mM Tris-HCl (pH 8.0), 200 mM EDTA

Kinase Storage Buffer—50% (v/v) glycerol, 20 mM Tris-HCl (pH 8.0), 100 mM KCl, 5 mM βME 100 mg/ml lysozyme—made in Kinase Storage Buffer and stored at −20° C.

2×PLD—5 ml of 20×PEB-I, 1 ml of 1 M DTT, 5 ml of 10% (v/v) Triton X-100, 1 ml of 100 mg/ml lysozyme and 38 ml of water 2×PZD—0.5 ml of 20× PEB-I, 100 III of 1 M DTT, 0.5 ml of 10% (v/v) Triton X-100, 10 µl of zymolase and 3.9 ml of water 10× Poly(C) Reaction Buffer—500 mM Tris-HCl (pH 8.4), 500 mM KCl, 100 mM $MgCl_2$ 1.25× Reaction Mix—1 ml of 10× Poly(C) Reaction Buffer, 100 µL of 1 M DTT, 1 ml of poly(C)/oligo(dG) (30 mM/12 mM in nucleotide), 10 µl of 100 mM dGTP, 5.87 ml of water and 20 µl of [$\alpha^{32}$P] dGTP at 10 µCi/µl Individual transformant colonies were inoculated into single wells of a 96 well culture plate. Each well contained 120 µl of EG-Ap medium (EG medium with 100µg/ml ampicillin) containing 0.2% arabinose. It is preferable to first inoculate a 96 well plate with selective medium without the inducer, to grow that master plate overnight, and then to make a replica of the master plate into a 96-well plate with the inducer and grow that plate overnight. The cultures were grown overnight (e.g., 15–20 hours) at 37° C. without shaking. Overnight cultures were mixed with an equal volume of 2×PLD at room temperature. These extracts were sometimes assayed directly for reverse transcriptase before the heating step. The extracts were heated by placing in a water bath for 5 or 10 minutes at temperatures that ranged from 50° C. to 60° C. Preferably, the cultures were heated for 5 minutes at 52° C. After the heating step, 10 µl of the extract was mixed with 40 µl of 1.25×RT reaction mix. This reaction was placed in a 37° C. water bath for 10 minutes. A small aliquot of the reaction mixture (5µl) was spotted onto a charged nylon membrane (Genescreen+, NEN). The membrane was washed twice with 10% TCA+1% sodium pyrophosphate, rinsed with ethanol, dried, and placed next to a phosphor screen. As an alternative, the membrane may be washed twice with 4% sodium pyrophosphate (pH 8.0), rinsed with ethanol, dried, and then placed next to a phosphor screen. Radioactive product that had been trapped on the filter was detected by analyzing the screen in a Posphorimager, using ImageQuant software (Molecular Devices).

Candidates were selected if they showed more reverse transcriptase activity (radioactivity) after the heat inactivation step. These candidates were screened a second time to confirm the phenotype. Candidates which appeared to be thermostable after the second screen were grown in small cultures and tested a third time for thermostable reverse transcriptase activity. Candidates that were reproducibly heat resistant were sequenced and the mutation in each clone was determined. An oligonucleotide corresponding to the mutagenized site was designed in which the codon for the mutagenized amino acid was randomized (NNK or NNN). These oligonucleotides were used in site-directed mutagenesis to generate a library in which all possible substitutions at the mutagenized site were made. This library was screened for thermostable reverse transcriptase activity, and the most promising clones were sequenced.

Screening of mutants in Segment 2 (see FIG. 2) resulted in the identification of one mutant, H204R. Screening of a library mutagenized at site H204 resulted in several mutants, but the only one that was more thermostable than M-MLV reverse transcriptase was another H204R mutant. H204R mutants of M-MLV reverse transcriptase have enhanced thermostability. Screening of mutants in segment 3 (see FIG. 2) resulted in one mutant, T306K. Randomization of the T306 position produced thermostable mutants which, when sequenced, were T306R. Both T306K and T306R mutants of M-MLV reverse transcriptase have about 1.5 fold enhanced thermostability.

Example 3

TdT Reverse Transcriptase Mutants

In checking fidelity mutants of reverse transcriptase (RT) for misextension in a 3 dNTP assay, it was observed that SuperScript™II reverse transcriptase extended 2–3 bases past the end of the template in the presence of 3 and 4 dNTPs. This non-template directed extension or TdT activity is reduced in many mutants, but in a few such as F309N and T197E it appears that this activity is severely reduced or eliminated. These mutants are probably in close proximity or in contact with the template-primer as determined by homology to HIV reverse transcriptase and its crystal structure with bound template-primer.

Methods

Mutagenesis

For F309N:

Primers were designed corresponding to the mutant position F309 with the silent insertion of a NgoMIV restriction site at amino acid positions 310–311. The primers encoded a random NNK sequence for this position generating a random library of F309 mutants, where N is any of the four bases and K is T or G. The primers along with internal SuperScript™II reverse transcriptase primers at an upstream SstI restriction site and a downstream SalI restriction site were used in a standard PCR reaction (10 ng SuperScript™II reverse transcriptase template, 2 µM of each primer, 48 µl SuperMix (Invitrogen Corp. (Carlsbad, Calif.)) for 20 cycles of 94° C. 15 sec, 55° C. 15 sec, 72° C. 30 sec) to generate two PCR fragments. These were a 240 base pair SstI-NgoMIV fragment and a 200 base pair NgoMIV-SalI fragment. The fragments were isolated and digested and ligated together and then inserted into the original SuperScript™II reverse transcriptase clone cut with SstI and SalI. The resulting ligation product was transformed in Max Efficiency DH10B (Invitrogen Corp. (Carlsbad, Calif.)) competent cells to create the library of mutants at site F309. This library was then plated overnight for selection.

For T197E and Y133A:

The mutants T197E and Y133A were made by oligo-directed mutagenesis as described in Kunkel, T. A. et al. *Methods Enzymol.* 204:125 (1991). Briefly, the SuperScript™II reverse transcriptase gene was inserted into pBADhisA (Invitrogen Corporation) vector and named pBAD-SSII. This plasmid was transformed into DH11S cells and the cells were infected with M13K07 helper phage from which single strand DNA was isolated. Oligos were designed corresponding to each mutation: T197E and Y133A. Each oligo (100 µM) was kinased with T4 polynucleotide kinase (Invitrogen Corp. (Carlsbad, Calif.)) using the Forward Reaction Buffer (Invitrogen Corp. (Carlsbad, Calif.)). The oligo was annealed to single stranded pBAD-SSII DNA. Native T7 DNA polymerase (USB) and T4 DNA ligase (Invitrogen Corp. (Carlsbad, Calif.)) were added with synthesis buffer (0.4 mM dNTPs, 17.5 mM Tris-HCl, pH 7.5, 5 mM $MgCl_2$, 2.5 mM DTT, and 1 mM ATP) to the annealed reaction on ice. The reactions were incubated at 37° C. for 30 minutes and terminated by adding 1 µl of 0.5 M EDTA. The reactions were transformed and plated with DH10B cells. Colonies were picked and mutants were determined by restriction enzyme analysis and sequenced for confirmation using an ABI 377 instrument and ABI Big Dye Terminator Cycle Sequencing Ready Reaction kit.

Selecting Colonies Containing Active Reverse Transcriptase.

Individual transformant colonies were inoculated into single wells of a 96 well culture plate. Each well contained 120 µl of media (EG-Ap) containing 0.2% arabinose. It is preferable to first inoculate a 96 well plate with selective medium without the inducer, to grow that master plate overnight, and then to make a replica of the master plate into a 96-well plate with the inducer and grow that plate overnight. The cultures were grown overnight at 37° C. without shaking. Overnight cultures were mixed with an equal volume of 2× PLD (1.8% glucose, 50 mM Tris-HCl, pH 8.0, 20 mM EDTA, 20 mM DTT, 1% Triton X-100, 2 mg/mL lysozyme) at room temperature. These extracts were assayed directly for reverse transcriptase activity by mixing 10 µl of the extract with 40 µl of 1.25×RT reaction mix (62.5 mM Tris-HCl, pH 8.4, 62.5 mM KCl, 12.5 mM $MgCl_2$, 12.5 mM DTT, 1.25 mM dGTP, polyC/oligo dG (3.75 mM/1.5 mM in nucleotide), [32P] dGTP). This reaction was placed in a 37° C. water bath for 10 minutes. A small aliquot of the reaction mixture (5 µl) was spotted onto a charged nylon membrane (Genescreen+, NEN). The membrane was washed twice with 10% TCA +1% sodium pyrophosphate, rinsed with ethanol, dried, and placed next to a phosphor screen. Radioactive product that had been trapped on the filter was detected by analyzing the screen in a Phosphorimager, using ImageQuant software (Molecular Devices). Candidates were selected if they showed reverse transcriptase activity (radioactivity). These candidates were screened a second time to confirm the phenotype. The confirmed candidates were then sequenced to determine which amino acids maintained detectable reverse transcriptase activity.

Purification of Reverse Transcriptase Mutants.

The cell pellet containing induced reverse transcriptase was suspended in a ratio of 2 mL Lysis buffer (40 mM Tris-HCl, pH 8.0, 0.1 M KCl, 1 mM PMSF)/1 gram of cell pellet. The suspension was sonicated on ice and then centrifuged at 27,000 g for 30 minutes. The cell-free extract was filtered through a 0.45 μ syringe filter. The cell-free extract was applied to a 5 mL Ni$^{2+}$ HI-TRAP column (Pharmacia) pre-equilibrated with 5 volumes 5 mM imidazole in buffer A (40 mM Tris HCl, pH 8.0, 10% glycerol, 0.01% Triton X-100, 0.1 M KCl) at 1 mL/min. The column was washed with 10 volumes 5 mM imidazole in buffer A. The reverse transcriptase was eluted by washing with 20 volumes of a gradient of 5 mM to 1M imidazole in buffer A. The eluate containing reverse transcriptase protein was applied to a 1 mL Mono-S column (Pharmacia) pre-equilibrated with 10 column volumes 50 mM KCl in buffer B (40 mM Tris-HCl, pH 8.0, 10% glycerol, 0.01% Triton X-100, 0.1 mM EDTA, 1 mM DTT) at a flow rate of 1.0 mL/min. The column was washed with 10 volumes of 50 mM KCl in buffer B. Reverse transcriptase was eluted with 20 volumes of a gradient from 50 mM to 1 M KCl in buffer B. The individual fractions were analyzed for RT activity. The fraction containing peak RT activity was dialyzed against storage buffer (40 mM Tris-HCl, pH 8.0, 50% glycerol, 0.01% Triton X-100, 0.1 mM EDTA, 1 mM DTT, 0.1 M KCl). The purified reverse transcriptases were more than 95% pure, as judged by SDS-PAGE. The protein concentrations were determined by using the Biorad colorimetric kit.

3 dNTP Assay Method.

Procedures were modified from those of Preston, B. D., et al. *Science* 242:1168 (1988). The DNA template-primer was prepared by annealing a 47-mer template (5'-GAGTTA-CAGTGTTTTTGTTCCAGTCTGTAGCAGT-GTGTGAATGGAAG-3') (SEQ ID NO:3) to an 18-mer primer (5'-CTTCCATTCACACACTGC-3') (SEQ ID NO:4) [$^{32}$P]-labeled at the 5'-end with T4 polynucleotide kinase (template:primer, 3:1). Assay mixture (10 μl) contained 5 nM template-primer, 50–200 nM reverse transcriptase as specified in figure legends, 3 or 4 dNTPs (250 μM each), 50 mM Tris-HCl (pH 8.3), 75 mM KCl, 3 mM MgCl$_2$, 10 mM DTT. Reactions were incubated at 37° C. for 30 minutes and terminated by the addition of 5 μl of 40 mM EDTA, 99% formamide. Reaction products were denatured by incubating at 95° C. for 5 minutes and analyzed by electrophoresis on urea 6% polyacrylamide gels.

To determine if any TdT activity was occurring in the control reaction of the 3 dNTP assay, which uses all 4 dNTPs, the control reaction was repeated with varying amounts of enzyme, >600 units to 20 units, at 37° C. for 30 minutes. For SuperScript™II, T197E, and Y133A, 200, 100, 50, and 20 units were used. For F309N, 646, 200, 50, and 20 units were used.

Results

We carried out a misinsertion assay of F309N (H204R, T306K) SuperScript™II reverse transcriptase, hereafter referred to as F309N, with DNA template. This assay was employed to compare the misincorporation capability of the mutant to SuperScript™II. The assay is a primer extension assay using synthetic DNA template-primer and biased dNTP pools containing only three of four dNTPs. The reactions are displayed on a gel in FIG. 3. While conducting this procedure to screen for mutants with lower misensertion/misextension rates it was observed that SuperScript™II reverse transcriptase extended 2–3 nucleotides past the template end and that some mutations reduced or appeared to eliminate this non-template directed extension or TdT activity. As shown in FIG. 4, in the presence of all 4 dNTPs, SuperScript™II reverse transcriptase and the mutant F309N were able to extend the primer approximately equally, with SuperScript™II reverse transcriptase adding 2 nucleotides past the template, and F309N adding none beyond the end of the template. To further evaluate this non-templated directed extension the control reaction for the 3 dNTP misextension assay containing all 4 dNTPs was carried out with SuperScript™II, F309N, T197E, and Y133A reverse transcriptase for 30 minutes with varying amounts of enzyme. The three mutants had shown very reduced levels of TdT activity in prior screens. Since it had been observed that 5 minutes with 20 units of enzyme was more than enough time for the primer extension to be completed, a 30 minute incubation and 200 to 646 units of reverse transcriptase were both in large excess over what was necessary for the reaction to be completed. As seen in FIG. 4, all the reverse transcriptase reactions at the lowest amount tested had similar extension products to the reactions at the highest unit concentrations demonstrating that the reaction had gone to completion. SuperScript™II reverse transcriptase added 2 nucleotides past the end of the template, F309N and T197E did not extend past the end of the template, and Y133A appears to have a small amount of product that is 1 nucleotide past the end of the template.

Example 4

Dual Thermostable and TdT Mutants

The F309 amino acid position in M-MLV reverse transcriptase (RT) aligns with the W266 position in HIV reverse transcriptase. This position is at the base of the thumb domain and is considered part of the minor groove binding tract which interacts with the minor groove of the template-primer. The mutations H204R and T306K have been shown to increase the thermostability of the enzyme. The F309N mutation in an H204R/T306K clone displays 2.3× lower mutation frequency in a lacZ forward assay (Table 5) on RNA template and shorter extension products in a 3 dNTP extension assay than SuperScript™II reverse transcriptase or H204R/T306K in SuperScript™II reverse transcriptase. Both findings support the claim of an enzyme with higher fidelity (Table 6).

TABLE 5

Mutation Frequency of M-MLV Reverse Transcriptase High Fidelity Mutants

| Construct | total plaques | mutant plaques | MF(×10$^{-4}$) |
| --- | --- | --- | --- |
| SSII | 15689 | 87 | 39 |
| SSII(H204R, T306K) | 14410 | 83 | 41 |
| SSII(H204R, T306K, F309N) | 11623 | 39 | 17 |
| SSII(H204R, T306K, F309N, V223H) | 11415 | 39 | 14 |

Table 5. The mutation frequency of SuperScript™II reverse transcriptase and point mutants. Mutation frequency (MF) was determined by dividing the number of mutant plaques (light blue or white) by the total number of plaques. The background mutant frequency of the starting DNA was 17×10$^{-4}$ for the first 3 constructs and 20×10$^{-4}$ for the last construct.

TABLE 6

Error Rates of M-MLV Reverse Transcriptase High Fidelity Mutants

|  | M-MLV | SuperScript™II | F309N | V223H/F309N |
|---|---|---|---|---|
| Overall ER (oER) | 1/17,000 | 1/15,000 | 1/34,000 | 1/41,000 |
| Mismatch % of total | 46 | 35 | 68 | 72 |
| ER (mER) | 1/37,000 | 1/42,000 | 1/50,000 | 1/58,000 |
| Frameshift % of total | 46 | 60 | 21 | 22 |
| ER (rER) | 1/37,000 | 1/25,000 | 1/162,000 | 1/188,000 |
| Strand Jump % of total | 8 | 5 | 11 | 6 |
| ER (jER) | 1/213,000 | 1/297,000 | 1/324,000 | 1/690,000 |

Mutagenesis. Using a standard site directed mutagenesis protocol, as described in Example 3, a primer containing the V223H mutation was annealed to single strand DNA of SuperScript™II with the following mutations: H204R, T306K, F309N. The colonies were sequenced to confirm the new combination of V223H, H204R, T306K, and F309N.

Selecting Colonies Containing Active Reverse Transcriptase. Colony selection was performed as in Example 3.

Purification of RT mutants. Purification was performed as in Example 3.

Sequencing of plaques. The plaques from the lacZ forward assay were transferred from the soft agar plate to Whatmann 3MM paper and allowed to dry for at least 1 hour. The plaque was then punched out and the plaque/paper disk was added directly to a sequencing reaction mix containing 4–8 μl ABI PRISM Dye Terminator Cycle Sequencing Ready Reaction (Perkin Elmer), 1 μl primer (GAA-GATCGCACTCCAGCCAGC) (SEQ ID NO:5), and distilled water to 20 μl total volume. The ABI cycle sequencing protocol was used for 96° C. 10 seconds, 50° C. 5 seconds, 60° C. 4 minutes for 25 cycles. The paper disks were removed and the reactions were precipitated, then resuspended in loading dye and run on an ABI 377 sequencing machine.

The sequences were compared to wild type lacZ alpha sequence and then classified as frameshift (either 1 nucleotide insertion or deletion), mismatch, or strand jump (an insertion or deletion between repeated sequences). The overall error rate for each class was determined by dividing the mutation frequency by the number of detectable sites (i.e., sites the alteration of which results in a phenotypic change) (116) multiplied by 0.5 (to exclude the original single strand contribution) and then multiplied by the percentage of mutants observed to be in each class. ER=MF/(detectable sites*0.5)*(% in each class).

3dNTP assay method. 3dNTP assays were performed as in Example 3.

Results

We carried out a misinsertion assay of F309N (H204R T306K) SuperScript™II reverse transcriptase, hereafter referred to as F309N, and V223H F309N (H204R T306K), hereafter referred to as V223H/F309N with DNA template. This assay was employed to compare the misincorporation capability of the mutant to SuperScript™II. The assay is a primer extension assay using synthetic DNA template-primer and biased dNTP pools containing only three of the four dNTPs. The reactions are displayed on a gel in FIG. 5 and FIG. 6. In this assay, higher efficiency of primer extension denotes lower fidelity. As shown in FIGS. 5 and 6, in the presence of all 4 dNTPs, SuperScript™II reverse transcriptase and the mutants F309N and V223H/F309N were able to extend the primer approximately equally, with some variance in the addition of non-template directed nucleotides at the end of the primer. However when incubated with biased pools of nucleotides, SuperScript™II reverse transcriptase was able to catalyze substantial extension past template nucleotides for which a complementary dNTP was missing, indicating use of incorrect nucleotides and lower fidelity. In FIG. 5, the F309N (2) mutant showed shorter extension products than SuperScript™II reverse transcriptase in each of the biased pools of three dNTPs, indicating less ability to incorporate incorrect nucleotides and thus higher fidelity. In FIG. 6, the V223H/F309N mutant was extended with just the dATP and dCTP pools. In each case V223H/F309N also had lower extension products than SuperScript™II. This corresponds with the results of the lacZα assay where the F309N and V223H/F309N mutants had a lower mutation frequency than SuperScript™II reverse transcriptase ($17 \times 10^{-4}$ and $14 \times 10^{-4}$ to $39 \times 10^{-4}$). The reverse transcriptase with just the H204R T306K mutations without F309N has a mutation frequency similar to SuperScript™II reverse transcriptase ($41 \times 10^{-4}$ to $39 \times 10^{-4}$), suggesting that these mutations do not influence fidelity. This data shows a correlation between the misinsertion assay on DNA and the lacZα assay on RNA wherein higher fidelity mutants had both shorter extension products with biased pools of dNTPs and lower mutation frequencies in the lacZα assay.

Example 5

Error Rate Determination

To determine Error Rates, mutant plaques from the lacZ forward assay were sequenced using known methods. The mutations were then classified into one of the following categories: mismatches for misinsertion events, frameshifts for single insertion or deletion events, or jumps for large insertions or deletions caused by jumping between similar sequences. An overall Error Rate was then determined for nucleic acid encoding the lacZ alpha peptide using the following equation:

$ER$ (error rate)=$MF$ (mutation frequency)/(number of detectable sites×0.5), where the number of detectable sites is 116.

Not all bases mutated in lacZ forward assays result in a detectable phenotypic change. To determine specific error rates for mismatch, frameshift and jumps, the mutation frequency was modified by multiplying by the percent of the total of each mutant category, and then used to determine the specific error rate. The following is a sequence map of the lacZα peptide in M13mp19 from SuperScript™II reverse transcriptase and the high fidelity SuperScript™II H203R T306K F309N reverse transcriptase assays. Underlining indicates deletions; "^" indicates insertions of the base A, T, C, or G shown above; A, T, C, or G shown above the complete sequence indicates mismatches.

Map of Mutations Introduced by SuperScript ™II

```
                                              T  C
         T                      T            TC  C
AGCGCAACGC AATTAATGTG AGTTAGCTCA CTCATTAGGC ACCCCAGGCT TTACACTTTA
              1                     1            4

CG                            C      CC
TGCTTCCGGC TCGTATGTTG TGTGGAATTG TGAGCGGATA ACAATTTCAC ACAGGAAACA
    1
   C
   CC                     CG         C
GCTATG ACC ATG ATT ACG^CCA AGC TTG CAT GCC TGC AGG TCG ACT CTA GAG GAT CCC CGG
                                                 1

T                             AAAA
                                  T A                            AAA
                       T          T A                             A
                T      T          T A                   T         A     C
GTA CCG AGC TCG AAT TCA CTG GCC GTC GTT^TTA CAA CGT CGT GAC TGG GAA AAC CCT GGC
                                    7                       1   1       1

TTTTT
                                            TTTTT
                                    C       TTTTT
                                    C       TTT
                                    A  T T
         TC  C           C       T  TC  T C T T     C      G     T
GTT ACC CAA CTT AAT CGC CTT GCA GCA CAT CCC^CCT^TTC^GCC AGC TGG CGT
                                        1   4

AAT AGC G     (SEQ ID NO:6)
```

TABLE 7

| | | | |
|---|---|---|---|
| Insertions | 40 | 38% | 60% frameshift (insertion or deletion) |
| Deletions | 23 | 22% | |
| Mismatches | 36 | 35% | 35% mismatch |
| Jumps | 5 | 5% | 5% Jumps |

TABLE 8

| | | |
|---|---|---|
| Overall Error Rate (oER) | 1/15,000 | $(39 \times 10^{-4})/(116 \times 0.5)$ |
| Mismatch Error Rate (mER) | 1/42,500 | $(0.35 \times 39 \times 10^{-4})/(116 \times 0.5)$ |
| Frameshift Error Rate (fER) | 1/25,000 | $(0.60 \times 39 \times 10^{-4})/(116 \times 0.5)$ |
| Jumps Error Rate (jER) | 1/297,000 | $(0.05 \times 39 \times 10^{-4})/(116 \times 0.5)$ |

All publications, Patents and Patent applications mentioned in this specification are indicative of the level of skill of those skilled in the art to which this invention pertains, and are herein incorporated by reference to the same extent as if each individual publication, Patent or Patent application was specifically and individually indicated to be incorporate by reference.

What is claimed is:

1. A mutant M-MLV reverse transcriptase comprising a polymerase domain having RNA-dependent DNA polymerase activity and a substitution in the amino acid sequence of the wild type M-MLV polymerase domain within (SEQ ID NO 8), wherein amino acid number 1 of SEQ ID NO: 8 is the threonine following the initial methionine, corresponding to a substitution selected from the group consisting of:
   (a) a substitution of leucine 52 of wild type M-MLV reverse transcriptase for a different amino acid;
   (b) a substitution of histidine 204 of wild type M-MLV reverse transcriptase for a different amino acid;
   (c) a substitution of methionine 289 of wild type M-MLV reverse transcriptase for a different amino acid; and
   (d) a substitution of threonine 306 of wild type M-MLV reverse transcriptase for a different amino acid.

2. The mutant reverse transcriptase of claim 1, wherein leucine 52 is replaced with proline.

3. The mutant reverse transcriptase of claim 1, wherein histidine 204 is replaced with arginine.

4. The mutant reverse transcriptase of claim 1, wherein methionine 289 is replaced with leucine.

5. The mutant reverse transcriptase of claim 1, wherein threonine 306 is replaced with either lysine or arginine.

6. The mutant reverse transcriptase of claim 1, wherein the mutant reverse transcriptase has a substitution of amino acids histidine 204 and threonine 306.

7. The mutant reverse transcriptase of claim 6, wherein histidine 204 is replaced with arginine and threonine 306 is replaced with either lysine or arginine.

8. The mutant reverse transcriptase of claim 1, which retains at least 50% of reverse transcriptase activity after heating to 50° C. for 5 minutes.

9. The mutant reverse transcriptase of claim 1, which retains at least 70% of reverse transcriptase activity after heating to 50° C. for 5 minutes.

10. The mutant reverse transcriptase of claim 1, which retains at least 85% of reverse transcriptase activity after heating to 50° C. for 5 minutes.

11. The mutant reverse transcriptase of claim 1, which retains at least 95% of reverse transcriptase activity after heating to 50° C. for 5 minutes.

12. The mutant reverse transcriptase of claim 1, wherein the mutant retroviral reverse transcriptase has one or more properties selected from the group consisting of:
  (a) reduced or substantially reduced RNase H activity in comparison to a corresponding wild-type reverse transcriptase;
  (b) reduced or substantially reduced terminal deoxynucleotidyl transferase activity in comparison to a corresponding wild-type reverse transcriptase; and
  (c) increased fidelity in comparison to a corresponding wild-type reverse transcriptase.

13. The mutant reverse transcriptase of claim 12, wherein the mutant retroviral reverse transcriptase has reduced or substantially reduced RNase H activity in comparison to a corresponding wild-type reverse transcriptase.

14. The mutant reverse transcriptase of claim 12, wherein the mutant retroviral reverse transcriptase has reduced or substantially reduced terminal deoxynucleotidyl transferase activity in comparison to a corresponding wild-type reverse transcriptase.

15. The mutant reverse transcriptase of claim 14, wherein the mutant reverse transcriptase has one or more modifications or mutations at positions corresponding to amino acids selected from the group consisting of:
  (a) tyrosine 133 of wild type M-MLV reverse transcriptase;
  (b) threonine 197 of wild type M-MLV reverse transcriptase; and
  (c) phenylalanine 309 of wild type M-MLV reverse transcriptase.

16. The mutant reverse transcriptase of claim 15, wherein tyrosine 133 is replaced with alanine.

17. The mutant reverse transcriptase of claim 15, wherein threonine 197 is replaced with glutamic acid.

18. The mutant reverse transcriptase of claim 15, wherein phenylalanine 309 is replaced with asparagine.

19. The mutant reverse transcriptase of claim 12, wherein the mutant retroviral reverse transcriptase has increased fidelity in comparison to a corresponding wild-type reverse transcriptase.

20. The mutant reverse transcriptase of claim 19, wherein the mutant reverse transcriptase has one or more modifications or mutations at positions corresponding to amino acids selected from the group consisting of:
  (a) tyrosine 64 of wild type M-MLV reverse transcriptase;
  (b) arginine 116 of wild type M-MLV reverse transcriptase; and
  (c) glutamine 190 of wild type M-MLV reverse transcriptase; and
  (d) valine 223 of wild type M-MLV reverse transcriptase.

21. The mutant reverse transcriptase of claim 1, wherein aspartic acid 524 is replaced with glycine, glutamic acid 562 is replaced with glutamine, and aspartic acid 583 is replaced with asparagine.

22. A kit for use in reverse transcription, amplification or sequencing of a nucleic acid molecule, the kit comprising one or more mutant reverse transcriptases of claim 1.

23. The kit of claim 22, the kit further comprising one or more components selected from the group consisting of one or more nucleotides, one or more DNA polymerases, a suitable buffer, one or more primers and one or more terminating agents.

24. The kit of claim 23, wherein the terminating agent is a dideoxynucleotide.

25. The mutant retroviral reverse transcriptase of claim 1, which comprises a substitution of histidine 204.

26. The kit of claim 22, wherein the mutant retroviral reverse transcriptase comprises a substitution of histidine 204.

* * * * *

SEQUENCE LISTING

<160> NUMBER OF SEQ ID NOS: 8

<210> SEQ ID NO 1
<211> LENGTH: 2151
<212> TYPE: DNA
<213> ORGANISM: Moloney-Murine Leukemia Virus
<220> FEATURE:
<221> NAME/KEY: CDS
<222> LOCATION: (1)..(2151)

<400> SEQUENCE: 1

```
atg ggg ggt tct cat cat cat cat cat cat ggt atg gct agc atg act      48
Met Gly Gly Ser His His His His His His Gly Met Ala Ser Met Thr
 1               5                  10                  15 ggt gga cag caa atg ggt cgg gat ctg tac gac gat gac gat aag cat      96
Gly Gly Gln Gln Met Gly Arg Asp Leu Tyr Asp Asp Asp Asp Lys His
                20                  25                  30
```

-continued

| | |
|---|---|
| atg acc cta aat ata gaa gat gag tat cgg cta cat gag acc tca aaa<br>Met Thr Leu Asn Ile Glu Asp Glu Tyr Arg Leu His Glu Thr Ser Lys<br>35 40 45 | 144 |
| gag cca gat gtt tct cta ggg tcc aca tgg ctg tct gat ttt cct cag<br>Glu Pro Asp Val Ser Leu Gly Ser Thr Trp Leu Ser Asp Phe Pro Gln<br>50 55 60 | 192 |
| gcc tgg gcg gaa acc ggg ggc atg gga ctg gca gtt cgc caa gct cct<br>Ala Trp Ala Glu Thr Gly Gly Met Gly Leu Ala Val Arg Gln Ala Pro<br>65 70 75 80 | 240 |
| ctg atc ata ctt ctg aaa gca acc tct acc ccc gtg tcc ata aaa caa<br>Leu Ile Ile Leu Leu Lys Ala Thr Ser Thr Pro Val Ser Ile Lys Gln<br>85 90 95 | 288 |
| tac ccc atg tca caa gaa gcc aga ctg ggg atc aag ccc cac ata cag<br>Tyr Pro Met Ser Gln Glu Ala Arg Leu Gly Ile Lys Pro His Ile Gln<br>100 105 110 | 336 |
| aga ctg ttg gac cag gga ata ctg gta ccc tgc cag tcc ccc tgg aac<br>Arg Leu Leu Asp Gln Gly Ile Leu Val Pro Cys Gln Ser Pro Trp Asn<br>115 120 125 | 384 |
| acg ccc ctg cta ccc gtc aag aaa ccc ggg act aat gat tac agg cct<br>Thr Pro Leu Leu Pro Val Lys Lys Pro Gly Thr Asn Asp Tyr Arg Pro<br>130 135 140 | 432 |
| gtc caa gat ctg aga gag gtc aac aaa cgc gta gaa gac atc cac ccc<br>Val Gln Asp Leu Arg Glu Val Asn Lys Arg Val Glu Asp Ile His Pro<br>145 150 155 160 | 480 |
| acc gta ccc aac ccc tac aac ctc ttg agt ggg ctc cca ccg tcc cac<br>Thr Val Pro Asn Pro Tyr Asn Leu Leu Ser Gly Leu Pro Pro Ser His<br>165 170 175 | 528 |
| cag tgg tac act gtt cta gac tta aaa gat gcc ttt ttc tgc ctg aga<br>Gln Trp Tyr Thr Val Leu Asp Leu Lys Asp Ala Phe Phe Cys Leu Arg<br>180 185 190 | 576 |
| ctc cac ccg acg tct cag cct ctc ttc gcc ttt gaa tgg aga gac cca<br>Leu His Pro Thr Ser Gln Pro Leu Phe Ala Phe Glu Trp Arg Asp Pro<br>195 200 205 | 624 |
| gag atg gga atc tct ggc caa cta acc tgg acc aga ctc cca cag gga<br>Glu Met Gly Ile Ser Gly Gln Leu Thr Trp Thr Arg Leu Pro Gln Gly<br>210 215 220 | 672 |
| ttc aaa aac agt ccc acc ctg ttt gat gag gca ctg cgc aga gac cta<br>Phe Lys Asn Ser Pro Thr Leu Phe Asp Glu Ala Leu Arg Arg Asp Leu<br>225 230 235 240 | 720 |
| gca gac ttc cgg atc cag cac cca gac ttg atc ctg cta cag tac gta<br>Ala Asp Phe Arg Ile Gln His Pro Asp Leu Ile Leu Leu Gln Tyr Val<br>245 250 255 | 768 |
| gat gac tta ctg ctg gcc gcc act tct gag ctc gac tgc caa caa ggt<br>Asp Asp Leu Leu Leu Ala Ala Thr Ser Glu Leu Asp Cys Gln Gln Gly<br>260 265 270 | 816 |
| act cgg gcc ctg tta caa acc cta gga gac ctc ggg tat cgg gcc tcg<br>Thr Arg Ala Leu Leu Gln Thr Leu Gly Asp Leu Gly Tyr Arg Ala Ser<br>275 280 285 | 864 |
| gcc aag aaa gcc caa att tgc cag aaa cag gtc aag tat ctg ggg tat<br>Ala Lys Lys Ala Gln Ile Cys Gln Lys Gln Val Lys Tyr Leu Gly Tyr<br>290 295 300 | 912 |
| ctt cta aaa gag ggt cag aga tgg ctg act gag gcc aga aaa gag act<br>Leu Leu Lys Glu Gly Gln Arg Trp Leu Thr Glu Ala Arg Lys Glu Thr<br>305 310 315 320 | 960 |
| gtg atg ggg cag cct act ccg aag acc ccg cgg caa cta agg gag ttc<br>Val Met Gly Gln Pro Thr Pro Lys Thr Pro Arg Gln Leu Arg Glu Phe<br>325 330 335 | 1008 |
| cta ggg acg gca ggc ttc tgt cgc ctc tgg atc cct ggg ttt gca gaa<br>Leu Gly Thr Ala Gly Phe Cys Arg Leu Trp Ile Pro Gly Phe Ala Glu<br> | 1056 |

-continued

```
                340                 345                 350
atg gca gcc ccc ttg tac cct ctc acc aaa acg ggg act ctg ttt aat    1104
Met Ala Ala Pro Leu Tyr Pro Leu Thr Lys Thr Gly Thr Leu Phe Asn
            355                 360                 365 tgg ggc cca gac caa caa aag gcc tat caa gaa atc aag caa gct ctt    1152
Trp Gly Pro Asp Gln Gln Lys Ala Tyr Gln Glu Ile Lys Gln Ala Leu
        370                 375                 380 cta act gcc cca gcc ctg ggg ttg cca gat ttg act aag ccc ttt gaa    1200
Leu Thr Ala Pro Ala Leu Gly Leu Pro Asp Leu Thr Lys Pro Phe Glu
385                 390                 395                 400 ctc ttt gtc gac gag aag cag ggc tac gcc aaa ggt gtc cta acg caa    1248
Leu Phe Val Asp Glu Lys Gln Gly Tyr Ala Lys Gly Val Leu Thr Gln
                405                 410                 415 aaa ctg gga cct tgg cgt cgg ccg gtg gcc tac ctg tcc aaa aag cta    1296
Lys Leu Gly Pro Trp Arg Arg Pro Val Ala Tyr Leu Ser Lys Lys Leu
            420                 425                 430 gac cca gta gca gct ggg tgg ccc cct tgc cta cgg atg gta gca gcc    1344
Asp Pro Val Ala Ala Gly Trp Pro Pro Cys Leu Arg Met Val Ala Ala
        435                 440                 445 att gcc gta ctg aca aag gat gca ggc aag cta acc atg gga cag cca    1392
Ile Ala Val Leu Thr Lys Asp Ala Gly Lys Leu Thr Met Gly Gln Pro
    450                 455                 460 cta gtc att ctg gcc ccc cat gca gta gag gca cta gtc aaa caa ccc    1440
Leu Val Ile Leu Ala Pro His Ala Val Glu Ala Leu Val Lys Gln Pro
465                 470                 475                 480 ccc gat cga tgg ctt tcc aac gcc cgg atg act cac tat cag gcc ttg    1488
Pro Asp Arg Trp Leu Ser Asn Ala Arg Met Thr His Tyr Gln Ala Leu
                485                 490                 495 ctt ttg gac acg gac cgg gtc cag ttc gga ccg gtg gta gcc ctg aac    1536
Leu Leu Asp Thr Asp Arg Val Gln Phe Gly Pro Val Val Ala Leu Asn
            500                 505                 510 ccg gct aca ctg ctc cca ctg cct gag gaa ggg ctg cag cac aac tgc    1584
Pro Ala Thr Leu Leu Pro Leu Pro Glu Glu Gly Leu Gln His Asn Cys
        515                 520                 525 ctt gat atc ctg gcc gaa gcc cac gga acc cga ccc gac cta acg gac    1632
Leu Asp Ile Leu Ala Glu Ala His Gly Thr Arg Pro Asp Leu Thr Asp
    530                 535                 540 cag ccg ctc cca gac gcc gac cac acc tgg tac acg ggt gga tcc agt    1680
Gln Pro Leu Pro Asp Ala Asp His Thr Trp Tyr Thr Gly Gly Ser Ser
545                 550                 555                 560 ctc ttg caa gag gga cag cgt aag gcg gga gct gcg gtg acc acc gag    1728
Leu Leu Gln Glu Gly Gln Arg Lys Ala Gly Ala Ala Val Thr Thr Glu
                565                 570                 575 acc gag gta atc tgg gct aaa gcc ctg cca gcc ggg aca tcc gct cag    1776
Thr Glu Val Ile Trp Ala Lys Ala Leu Pro Ala Gly Thr Ser Ala Gln
            580                 585                 590 cgg gct cag ctg ata gca ctc acc cag gcc cta agg atg gca gaa ggt    1824
Arg Ala Gln Leu Ile Ala Leu Thr Gln Ala Leu Arg Met Ala Glu Gly
        595                 600                 605 aag aag cta aat gtt tat acg aat tcc cgt tat gct ttt gct act gcc    1872
Lys Lys Leu Asn Val Tyr Thr Asn Ser Arg Tyr Ala Phe Ala Thr Ala
    610                 615                 620 cat atc cat gga gaa ata tac aga agg cgt ggg ttg ctc aca tca gaa    1920
His Ile His Gly Glu Ile Tyr Arg Arg Arg Gly Leu Leu Thr Ser Glu
625                 630                 635                 640 ggc aaa gag atc aaa aat aag gac gag ata ttg gcc cta cta aaa gcc    1968
Gly Lys Glu Ile Lys Asn Lys Asp Glu Ile Leu Ala Leu Leu Lys Ala
                645                 650                 655 ctc ttt ctg ccc aaa aga ctt agc ata atc cat tgt cca gga cat caa    2016
```

```
Leu Phe Leu Pro Lys Arg Leu Ser Ile Ile His Cys Pro Gly His Gln
            660                 665                 670 aag gga cac agc gcc gag gct aga ggc aac cgg atg gct gac caa gcg    2064
Lys Gly His Ser Ala Glu Ala Arg Gly Asn Arg Met Ala Asp Gln Ala
            675                 680                 685 gcc cga aag gca gcc atc aca gag aat cca gac acc tct acc ctc ctc    2112
Ala Arg Lys Ala Ala Ile Thr Glu Asn Pro Asp Thr Ser Thr Leu Leu
        690                 695                 700 ata gaa aat tca tca ccc aat tcc cgc tta att aat taa                 2151
Ile Glu Asn Ser Ser Pro Asn Ser Arg Leu Ile Asn
705                 710                 715

<210> SEQ ID NO 2
<211> LENGTH: 716
<212> TYPE: PRT
<213> ORGANISM: Moloney-Murine Leukemia Virus

<400> SEQUENCE: 2

Met Gly Gly Ser His His His His His Gly Met Ala Ser Met Thr
1               5                   10                  15

Gly Gly Gln Gln Met Gly Arg Asp Leu Tyr Asp Asp Asp Lys His
            20                  25                  30

Met Thr Leu Asn Ile Glu Asp Glu Tyr Arg Leu His Glu Thr Ser Lys
        35                  40                  45

Glu Pro Asp Val Ser Leu Gly Ser Thr Trp Leu Ser Asp Phe Pro Gln
    50                  55                  60

Ala Trp Ala Glu Thr Gly Gly Met Gly Leu Ala Val Arg Gln Ala Pro
65                  70                  75                  80

Leu Ile Ile Leu Leu Lys Ala Thr Ser Thr Pro Val Ser Ile Lys Gln
                85                  90                  95

Tyr Pro Met Ser Gln Glu Ala Arg Leu Gly Ile Lys Pro His Ile Gln
            100                 105                 110

Arg Leu Leu Asp Gln Gly Ile Leu Val Pro Cys Gln Ser Pro Trp Asn
        115                 120                 125

Thr Pro Leu Leu Pro Val Lys Lys Pro Gly Thr Asn Asp Tyr Arg Pro
    130                 135                 140

Val Gln Asp Leu Arg Glu Val Asn Lys Arg Val Glu Asp Ile His Pro
145                 150                 155                 160

Thr Val Pro Asn Pro Tyr Asn Leu Leu Ser Gly Leu Pro Pro Ser His
                165                 170                 175

Gln Trp Tyr Thr Val Leu Asp Leu Lys Asp Ala Phe Phe Cys Leu Arg
            180                 185                 190

Leu His Pro Thr Ser Gln Pro Leu Phe Ala Phe Glu Trp Arg Asp Pro
        195                 200                 205

Glu Met Gly Ile Ser Gly Gln Leu Thr Trp Thr Arg Leu Pro Gln Gly
    210                 215                 220

Phe Lys Asn Ser Pro Thr Leu Phe Asp Glu Ala Leu Arg Arg Asp Leu
225                 230                 235                 240

Ala Asp Phe Arg Ile Gln His Pro Asp Leu Ile Leu Leu Gln Tyr Val
                245                 250                 255

Asp Asp Leu Leu Leu Ala Ala Thr Ser Glu Leu Asp Cys Gln Gln Gly
            260                 265                 270

Thr Arg Ala Leu Leu Gln Thr Leu Gly Asp Leu Gly Tyr Arg Ala Ser
        275                 280                 285

Ala Lys Lys Ala Gln Ile Cys Gln Lys Gln Val Lys Tyr Leu Gly Tyr
    290                 295                 300
```

-continued

```
Leu Leu Lys Glu Gly Gln Arg Trp Leu Thr Glu Ala Arg Lys Glu Thr
305                 310                 315                 320

Val Met Gly Gln Pro Thr Pro Lys Thr Pro Arg Gln Leu Arg Glu Phe
                325                 330                 335

Leu Gly Thr Ala Gly Phe Cys Arg Leu Trp Ile Pro Gly Phe Ala Glu
                340                 345                 350

Met Ala Ala Pro Leu Tyr Pro Leu Thr Lys Thr Gly Thr Leu Phe Asn
                355                 360                 365

Trp Gly Pro Asp Gln Gln Lys Ala Tyr Gln Glu Ile Lys Gln Ala Leu
            370                 375                 380

Leu Thr Ala Pro Ala Leu Gly Leu Pro Asp Leu Thr Lys Pro Phe Glu
385                 390                 395                 400

Leu Phe Val Asp Glu Lys Gln Gly Tyr Ala Lys Gly Val Leu Thr Gln
                405                 410                 415

Lys Leu Gly Pro Trp Arg Arg Pro Val Ala Tyr Leu Ser Lys Lys Leu
                420                 425                 430

Asp Pro Val Ala Ala Gly Trp Pro Pro Cys Leu Arg Met Val Ala Ala
            435                 440                 445

Ile Ala Val Leu Thr Lys Asp Ala Gly Lys Leu Thr Met Gly Gln Pro
            450                 455                 460

Leu Val Ile Leu Ala Pro His Ala Val Glu Ala Leu Val Lys Gln Pro
465                 470                 475                 480

Pro Asp Arg Trp Leu Ser Asn Ala Arg Met Thr His Tyr Gln Ala Leu
                485                 490                 495

Leu Leu Asp Thr Asp Arg Val Gln Phe Gly Pro Val Val Ala Leu Asn
            500                 505                 510

Pro Ala Thr Leu Leu Pro Leu Pro Glu Glu Gly Leu Gln His Asn Cys
            515                 520                 525

Leu Asp Ile Leu Ala Glu Ala His Gly Thr Arg Pro Asp Leu Thr Asp
            530                 535                 540

Gln Pro Leu Pro Asp Ala Asp His Thr Trp Tyr Thr Gly Gly Ser Ser
545                 550                 555                 560

Leu Leu Gln Glu Gly Gln Arg Lys Ala Gly Ala Ala Val Thr Thr Glu
                565                 570                 575

Thr Glu Val Ile Trp Ala Lys Ala Leu Pro Ala Gly Thr Ser Ala Gln
                580                 585                 590

Arg Ala Gln Leu Ile Ala Leu Thr Gln Ala Leu Arg Met Ala Glu Gly
            595                 600                 605

Lys Lys Leu Asn Val Tyr Thr Asn Ser Arg Tyr Ala Phe Ala Thr Ala
610                 615                 620

His Ile His Gly Glu Ile Tyr Arg Arg Arg Gly Leu Leu Thr Ser Glu
625                 630                 635                 640

Gly Lys Glu Ile Lys Asn Lys Asp Glu Ile Leu Ala Leu Leu Lys Ala
                645                 650                 655

Leu Phe Leu Pro Lys Arg Leu Ser Ile Ile His Cys Pro Gly His Gln
                660                 665                 670

Lys Gly His Ser Ala Glu Ala Arg Gly Asn Arg Met Ala Asp Gln Ala
            675                 680                 685

Ala Arg Lys Ala Ala Ile Thr Glu Asn Pro Asp Thr Ser Thr Leu Leu
            690                 695                 700

Ile Glu Asn Ser Ser Pro Asn Ser Arg Leu Ile Asn
705                 710                 715
```

<210> SEQ ID NO 3
<211> LENGTH: 47
<212> TYPE: DNA
<213> ORGANISM: Artificial
<220> FEATURE:
<223> OTHER INFORMATION: Oligonucleotide template

<400> SEQUENCE: 3
gagttacagt gttttgttc cagtctgtag cagtgtgtga atggaag          47

<210> SEQ ID NO 4
<211> LENGTH: 18
<212> TYPE: DNA
<213> ORGANISM: Artificial
<220> FEATURE:
<223> OTHER INFORMATION: Oligonucleotide primer

<400> SEQUENCE: 4
cttccattca cacactgc                                          18

<210> SEQ ID NO 5
<211> LENGTH: 21
<212> TYPE: DNA
<213> ORGANISM: Artificial
<220> FEATURE:
<223> OTHER INFORMATION: Oligonucleotide primer

<400> SEQUENCE: 5
gaagatcgca ctccagccag c                                      21

<210> SEQ ID NO 6
<211> LENGTH: 298
<212> TYPE: DNA
<213> ORGANISM: Escherichia coli

<400> SEQUENCE: 6
agcgcaacgc aattaatgtg agttagctca ctcattaggc accccaggct ttacacttta    60
tgcttccggc tcgtatgttg tgtggaattg tgagcggata caatttcac acaggaaaca    120 gctatgacca tgattacgcc aagcttgcat gcctgcaggt cgactctaga ggatccccgg   180
gtaccgagct cgaattcact ggccgtcgtt ttacaacgtc gtgactggga aaaccctggc   240
gttacccaac ttaatcgcct tgcagcacat ccccctttcg ccagctggcg taatagcg     298

<210> SEQ ID NO 7
<211> LENGTH: 1515
<212> TYPE: DNA
<213> ORGANISM: Moloney-Murine Leukemia Virus
<220> FEATURE:
<221> NAME/KEY: CDS
<222> LOCATION: (1)..(1515)

<400> SEQUENCE: 7

```
atg acc cta aat ata gaa gat gag cat cgg cta cat gag acc tca aaa      48
Met Thr Leu Asn Ile Glu Asp Glu His Arg Leu His Glu Thr Ser Lys
1               5                  10                  15 gag cca gat gtt tct cta ggg tcc aca tgg ctg tct gat ttt cct cag      96
Glu Pro Asp Val Ser Leu Gly Ser Thr Trp Leu Ser Asp Phe Pro Gln
            20                  25                  30 gcc tgg gcg gaa acc ggg ggc atg gga ctg gca gtt cgc caa gct cct     144
Ala Trp Ala Glu Thr Gly Gly Met Gly Leu Ala Val Arg Gln Ala Pro
        35                  40                  45 ctg atc ata cct ctg aaa gca acc tct acc ccc gtg tcc ata aaa caa     192
Leu Ile Ile Pro Leu Lys Ala Thr Ser Thr Pro Val Ser Ile Lys Gln
```

```
                50                      55                      60
tac ccc atg tca caa gaa gcc aga ctg ggg atc aag ccc cac ata cag        240
Tyr Pro Met Ser Gln Glu Ala Arg Leu Gly Ile Lys Pro His Ile Gln
 65                  70                      75                  80 aga ctg ttg gac cag gga ata ctg gta ccc tgc cag tcc ccc tgg aac        288
Arg Leu Leu Asp Gln Gly Ile Leu Val Pro Cys Gln Ser Pro Trp Asn
                     85                      90                  95 acg ccc ctg cta ccc gtt aag aaa cca ggg act aat gat tat agg cct        336
Thr Pro Leu Leu Pro Val Lys Lys Pro Gly Thr Asn Asp Tyr Arg Pro
                 100                     105                 110 gtc cag gat ctg aga gaa gtc aac aag cgg gtg gaa gac atc cac ccc        384
Val Gln Asp Leu Arg Glu Val Asn Lys Arg Val Glu Asp Ile His Pro
             115                     120                 125 acc gtg ccc aac cct tac aac ctc ttg agc ggg ctc cca ccg tcc cac        432
Thr Val Pro Asn Pro Tyr Asn Leu Leu Ser Gly Leu Pro Pro Ser His
         130                     135                 140 cag tgg tac act gtg ctt gat tta aag gat gcc ttt ttc tgc ctg aga        480
Gln Trp Tyr Thr Val Leu Asp Leu Lys Asp Ala Phe Phe Cys Leu Arg
145                     150                     155                 160 ctc cac ccc acc agt cag cct ctc ttc gcc ttt gag tgg aga gat cca        528
Leu His Pro Thr Ser Gln Pro Leu Phe Ala Phe Glu Trp Arg Asp Pro
                     165                     170                 175 gag atg gga atc tca gga caa ttg acc tgg acc aga ctc cca cag ggt        576
Glu Met Gly Ile Ser Gly Gln Leu Thr Trp Thr Arg Leu Pro Gln Gly
                 180                     185                 190 ttc aaa aac agt ccc acc ctg ttt gat gag gca ctg cac aga gac cta        624
Phe Lys Asn Ser Pro Thr Leu Phe Asp Glu Ala Leu His Arg Asp Leu
             195                     200                 205 gca gac ttc cgg atc cag cac cca gac ttg atc ctg cta cag tac gtg        672
Ala Asp Phe Arg Ile Gln His Pro Asp Leu Ile Leu Leu Gln Tyr Val
         210                     215                 220 gat gac tta ctg ctg gcc gcc act tct gag cta gac tgc caa caa ggt        720
Asp Asp Leu Leu Leu Ala Ala Thr Ser Glu Leu Asp Cys Gln Gln Gly
225                     230                     235                 240 act cgg gcc ctg tta caa acc cta ggg aac ctc ggg tat cgg gcc tcg        768
Thr Arg Ala Leu Leu Gln Thr Leu Gly Asn Leu Gly Tyr Arg Ala Ser
                     245                     250                 255 gcc aag aaa gcc caa att tgc cag aaa cag gtc aag tat ctg ggg tat        816
Ala Lys Lys Ala Gln Ile Cys Gln Lys Gln Val Lys Tyr Leu Gly Tyr
                 260                     265                 270 ctt cta aaa gag ggt cag aga tgg ctg act gag gcc aga aaa gag act        864
Leu Leu Lys Glu Gly Gln Arg Trp Leu Thr Glu Ala Arg Lys Glu Thr
             275                     280                 285 gtg atg ggg cag cct act ccg aag acc cct cga caa cta agg gag ttc        912
Val Met Gly Gln Pro Thr Pro Lys Thr Pro Arg Gln Leu Arg Glu Phe
         290                     295                 300 cta ggg acg gca ggc ttc tgt cgc ctc tgg atc cct ggg ttt gca gaa        960
Leu Gly Thr Ala Gly Phe Cys Arg Leu Trp Ile Pro Gly Phe Ala Glu
305                     310                     315                 320 atg gca gcc ccc ttg tac cct ctc acc aaa acg ggg act ctg ttt aat       1008
Met Ala Ala Pro Leu Tyr Pro Leu Thr Lys Thr Gly Thr Leu Phe Asn
                     325                     330                 335 tgg ggc cca gac caa caa aag gcc tat caa gaa atc aag caa gct ctt       1056
Trp Gly Pro Asp Gln Gln Lys Ala Tyr Gln Glu Ile Lys Gln Ala Leu
                 340                     345                 350 cta act gcc cca gcc ctg ggg ttg cca gat ttg act aag ccc ttt gaa       1104
Leu Thr Ala Pro Ala Leu Gly Leu Pro Asp Leu Thr Lys Pro Phe Glu
             355                     360                 365 ctc ttt gtc gac gag aag cag ggc tac gcc aaa ggt gtc cta acg caa       1152
```

```
Leu Phe Val Asp Glu Lys Gln Gly Tyr Ala Lys Gly Val Leu Thr Gln
    370                 375                 380 aaa ctg gga cct tgg cgt cgg ccg gtg gcc tac ctg tcc aaa aag cta      1200
Lys Leu Gly Pro Trp Arg Arg Pro Val Ala Tyr Leu Ser Lys Lys Leu
385                 390                 395                 400 gac cca gta gca gct ggg tgg ccc cct tgc cta cgg atg gta gca gcc      1248
Asp Pro Val Ala Ala Gly Trp Pro Pro Cys Leu Arg Met Val Ala Ala
                405                 410                 415 att gcc gta ctg aca aag gat gca ggc aag cta acc atg gga cag cca      1296
Ile Ala Val Leu Thr Lys Asp Ala Gly Lys Leu Thr Met Gly Gln Pro
            420                 425                 430 cta gtc att ctg gcc ccc cat gca gta gag gca cta gtc aaa caa ccc      1344
Leu Val Ile Leu Ala Pro His Ala Val Glu Ala Leu Val Lys Gln Pro
        435                 440                 445 ccc gac cgc tgg ctt tcc aac gcc cgg atg act cac tat cag gcc ttg      1392
Pro Asp Arg Trp Leu Ser Asn Ala Arg Met Thr His Tyr Gln Ala Leu
    450                 455                 460 ctt ttg gac acg gac cgg gtc cag ttc gga ccg gtg gta gcc ctg aac      1440
Leu Leu Asp Thr Asp Arg Val Gln Phe Gly Pro Val Val Ala Leu Asn
465                 470                 475                 480 ccg gct acg ctg ctc cca ctg cct gag gaa ggg ctg caa cac aac tgc      1488
Pro Ala Thr Leu Leu Pro Leu Pro Glu Glu Gly Leu Gln His Asn Cys
                485                 490                 495 ctt gat aat tcc cgc tta att aat taa                                  1515
Leu Asp Asn Ser Arg Leu Ile Asn
            500

<210> SEQ ID NO 8
<211> LENGTH: 504
<212> TYPE: PRT
<213> ORGANISM: Moloney-Murine Leukemia Virus

<400> SEQUENCE: 8

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190
```

-continued

```
Phe Lys Asn Ser Pro Thr Leu Phe Asp Glu Ala Leu His Arg Asp Leu
        195             200             205

Ala Asp Phe Arg Ile Gln His Pro Asp Leu Ile Leu Leu Gln Tyr Val
        210             215             220

Asp Asp Leu Leu Leu Ala Ala Thr Ser Glu Leu Asp Cys Gln Gln Gly
225             230             235             240

Thr Arg Ala Leu Leu Gln Thr Leu Gly Asn Leu Gly Tyr Arg Ala Ser
            245             250             255

Ala Lys Lys Ala Gln Ile Cys Gln Lys Gln Val Lys Tyr Leu Gly Tyr
            260             265             270

Leu Leu Lys Glu Gly Gln Arg Trp Leu Thr Glu Ala Arg Lys Glu Thr
        275             280             285

Val Met Gly Gln Pro Thr Pro Lys Thr Pro Arg Gln Leu Arg Glu Phe
        290             295             300

Leu Gly Thr Ala Gly Phe Cys Arg Leu Trp Ile Pro Gly Phe Ala Glu
305             310             315             320

Met Ala Ala Pro Leu Tyr Pro Leu Thr Lys Thr Gly Thr Leu Phe Asn
            325             330             335

Trp Gly Pro Asp Gln Gln Lys Ala Tyr Gln Glu Ile Lys Gln Ala Leu
            340             345             350

Leu Thr Ala Pro Ala Leu Gly Leu Pro Asp Leu Thr Lys Pro Phe Glu
        355             360             365

Leu Phe Val Asp Glu Lys Gln Gly Tyr Ala Lys Gly Val Leu Thr Gln
        370             375             380

Lys Leu Gly Pro Trp Arg Arg Pro Val Ala Tyr Leu Ser Lys Lys Leu
385             390             395             400

Asp Pro Val Ala Ala Gly Trp Pro Pro Cys Leu Arg Met Val Ala Ala
            405             410             415

Ile Ala Val Leu Thr Lys Asp Ala Gly Lys Leu Thr Met Gly Gln Pro
            420             425             430

Leu Val Ile Leu Ala Pro His Ala Val Glu Ala Leu Val Lys Gln Pro
        435             440             445

Pro Asp Arg Trp Leu Ser Asn Ala Arg Met Thr His Tyr Gln Ala Leu
        450             455             460

Leu Leu Asp Thr Asp Arg Val Gln Phe Gly Pro Val Val Ala Leu Asn
465             470             475             480

Pro Ala Thr Leu Leu Pro Leu Pro Glu Glu Gly Leu Gln His Asn Cys
            485             490             495

Leu Asp Asn Ser Arg Leu Ile Asn
            500
```